United States Patent
Kozhemyakin et al.

(10) Patent No.: US 6,251,857 B1
(45) Date of Patent: *Jun. 26, 2001

(54) CYTOKINE AND HEMOPOIETIC FACTOR ENDOGENOUS PRODUCTION ENHANCER AND METHODS OF USE THEREOF

(75) Inventors: Leonid A. Kozhemyakin; Mark B. Balazovski, both of St. Petersburg (RU)

(73) Assignee: Novelos Therapeutics, Inc., Newton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/766,557

(22) Filed: Dec. 11, 1996

Related U.S. Application Data

(63) Continuation-in-part of application No. 08/733,886, filed on Oct. 18, 1996.

(30) Foreign Application Priority Data

Dec. 14, 1995 (RU) .................................. 95120403

(51) Int. Cl.[7] .......................... A61K 38/06; A61K 38/08; C07K 5/023; C07K 5/037

(52) U.S. Cl. ................................. 514/6; 514/17; 514/18; 530/332

(58) Field of Search .................................. 514/18, 21, 6, 514/17; 530/331, 332

(56) References Cited

U.S. PATENT DOCUMENTS

| | | | |
|---|---|---|---|
| 4,761,399 | 8/1988 | Piletto et al. | 514/19 |
| 4,871,528 | 10/1989 | Tognella et al. | 424/649 |
| 4,927,808 | 5/1990 | Kitahara et al. | 514/19 |
| 4,968,671 | 11/1990 | Asano et al. | 514/18 |
| 5,223,488 | * 6/1993 | Ogata et al. | 514/18 |
| 5,248,697 | 9/1993 | Wilmore | 514/563 |
| 5,916,878 | 6/1999 | Kolobov et al. | 514/19 |

FOREIGN PATENT DOCUMENTS

| | | |
|---|---|---|
| 616 803 A2 | 2/1994 | (EP) . |
| 4-9336 | * 1/1992 | (JP) . |
| WO92/21368 | 10/1992 | (WO) . |
| WO94/00141 | 6/1994 | (WO) . |
| WO96/40205 | 12/1996 | (WO) . |

OTHER PUBLICATIONS

Araie, M., et al. (1988) *Invest. Ophthalmol. Vis. Sci.* 29(12): 1884–87.*

Krieter, H., et al. (1994) *Cardiosci.* 5(2): 115–26.*

International Search Report from International application No. PCT/RU 96/00226 filed Aug. 8, 1996.

Hansson M., Soderstrom T. The colony stimulating factors, Med Oncol Tumor Pharmacother, 1993, 10(1–2), pp. 5–12.

(List continued on next page.)

Primary Examiner—Jeffrey E. Russel
(74) Attorney, Agent, or Firm—Wolf, Greenfield & Sacks, P.C.

(57) ABSTRACT

A method of stimulating endogenous production of cytokines and hemopoietic factors by introducing to a mammalian body in need of stimulation of cytokines or hemopoietic factors or both, an effective amount of oxidized glutathione and/or its therapeutically beneficial salts, and/or its therapeutically beneficial derivatives, for a period of time to stimulate said endogenous production to obtain a therapeutic effect. Oxidized glutathione with or without extenders are used in drug forms.

60 Claims, 7 Drawing Sheets

S-thioethylamine·glutathione disulfide

OTHER PUBLICATIONS

Dillman R.O. The clinical experience with interleukin–2 in cancer therapy, Cancer Biother, 1994 Fal. (3), pp. 183–209.

Hieber U., Heim M E. Tumor necrosis factor the treatment of malignancies, Oncology, Mar.–Apr. 1994 51(2) pp. 142–53.

Neidhart J.A. Hematopoietic cytokines, Current use in cancer therapy, Cancer, Dec. 1, 1993 72(11 Suppl)., pp. 3381–6.

Murray H.W. Interferon–gamma and host antimicrobial defense: current and future clinical applications. Am J Med. Nov. 1994 97(5), pp. 459–67.

Cirelli R. Tyring S.K. Interferons in human papillomavirus infections. Antiviral Res. Jul. 1994 24(2–3), pp. 191–204.

Sher A. Coffman R.L. Regulation of immunity to parasites by T–cells and T–cell derived cytokines. Annu. Rev. Immunolo., 1992, 10, pp. 385–409.

Offenstadt G., Guidet B., Staikowsky F. Cytokines and severe infections. Pathol Biol (Paris), Oct. 1993 41 (8Pt 2), pp. 820–31.

Nelson S. Role of granulocyte colony–stimulating factor in the immune response to acute bacterial infection in the nonneutropenic host: an overview, Clin Infect Dis. Feb. 1994 18 Suppl 2P S197–204.

Nemunaitis J Use of hematopoietic growth factors in marrow transplantation Curr Opin Oncol Mar. 1994 6(2), pp. 139–45.

Forman A.D. Neurologic complications of cytokine therapy, Oncology (Huntingt), Apr. 1994 8(4), pp. 105–10: discussion 113, 116–7.

Mittelman M., Lessin L. S. Clinical application of recombinant erythropoietin in myelodysplasia, Hematol Clin North Am. Oct. 1994 8(5), pp. 993–1009.

Hack C.E., Ogilvie A.C., Eisele B., Eerenberg A.J., Wagstaff J., Thijs L.G. C1–inihibitor substitution therapy in septic shock and in the vascular leak syndrome induced by high doses of interleukin–2, Intensive Care Med. 1993, 19 Suppl 1P S19–28.

Saito M. OK–432, a killed streptococcal preparation, in the treatment of animal and human cancer and its mechanisms of action, Form on immunomodulators, Ed. Guenounou M. John Libbey Eurotext, paris, 1995, pp. 1–11.

Barot–Ciorbaru R., Bona C. Immunomodulators from *Nocardia opaca*. Form on immunomodulators, Ed. Guenounou M. John Libbey Eurotext, Paris, 1995, pp. 1–11.

Meister A. Anderson M.E. Glutathione. Annu. Rev. Biochem., 1983, 52:711–60.

Beutler E. Nutritional and metabolic aspects of glutathione, Review. Annu. Rev. Nutr., 1989, 9:287.

Textbook of biochemistry: with clinical correlations. Ed. Devlin T.M. 3rd ed. 1992, Wiley–Liss, Inc., NY, p. 525.

Ehrer J.P, Lund L.G. Cellular reducing equivalents and oxidative stress. Free Radic Biol Med. 1994 Jul. pp. 65–75.

Michiels C., Raes M., Toussaint O., Remacle J. Importance of Se–glutathione peroxidase, catalase, and Cu/ Zn–SOD for cell survival against oxidative stress. Free Radic Biol Med. 1994 Sep. 17(3), pp. 235,48.

Cohen G. Enzymatic/nonenzymatic sources of oxyradicals and regulation of antioxidant defenses, Ann NY Acad Sci. Nov. 17, 1994, 738, pp. 8–14.

Beckett G.J., Hayes J.D. Glutathione S–transferase: biomedical applications, Advan. Clin. Chem. 1993 vol. 30, pp. 281–380.

Droge W., Schultze–Osthoff K., Mihm S., Galter D., Schenk H., Eck H.P., Roth S., Gmunder H. Functions of glutathione and glutathione disulfide in immunology and immunopathology, FASEB J. 1994 Nov. 8(14) pp. 1131–8.

Giugliano D., Ceriello A., Paoliso G. Diabetes mellitus, hypertension, and cardiovascular disease: which role oxidative stress? Metabolism, 1995 Mar. 44(3), pp. 363–8.

Keusch G.T. Antioxidants in infection. J Nutr Sci Vitaminol (Tokyo), 1993, 39 Suppl P S 23–33.

Sokolovsky M., wILCHEK m., Patchornik A. On the synthesis of cystein peptides, J. Amer. Chem. Soc. 1964, Mar. 86(6), pp. 1202–1206.

Bloy C. mORALES m., Guenounou M. RU41740 (Biostim), an immunomodulating agent from bacterial origin, Guenounou M.John Libbery Eurotext, Paris, 1995, pp. 1–11.

* cited by examiner

Glutathione oxidized

S-thioethylamine·glutathione disulfide bis-[DL-6,8, thioctic acid]·glutathione disulfide

[β-alanyl-L-hystidyl]·glutathione disulfide

[9-β-D-ribofuranosyladenyl]·glutathione disulfide

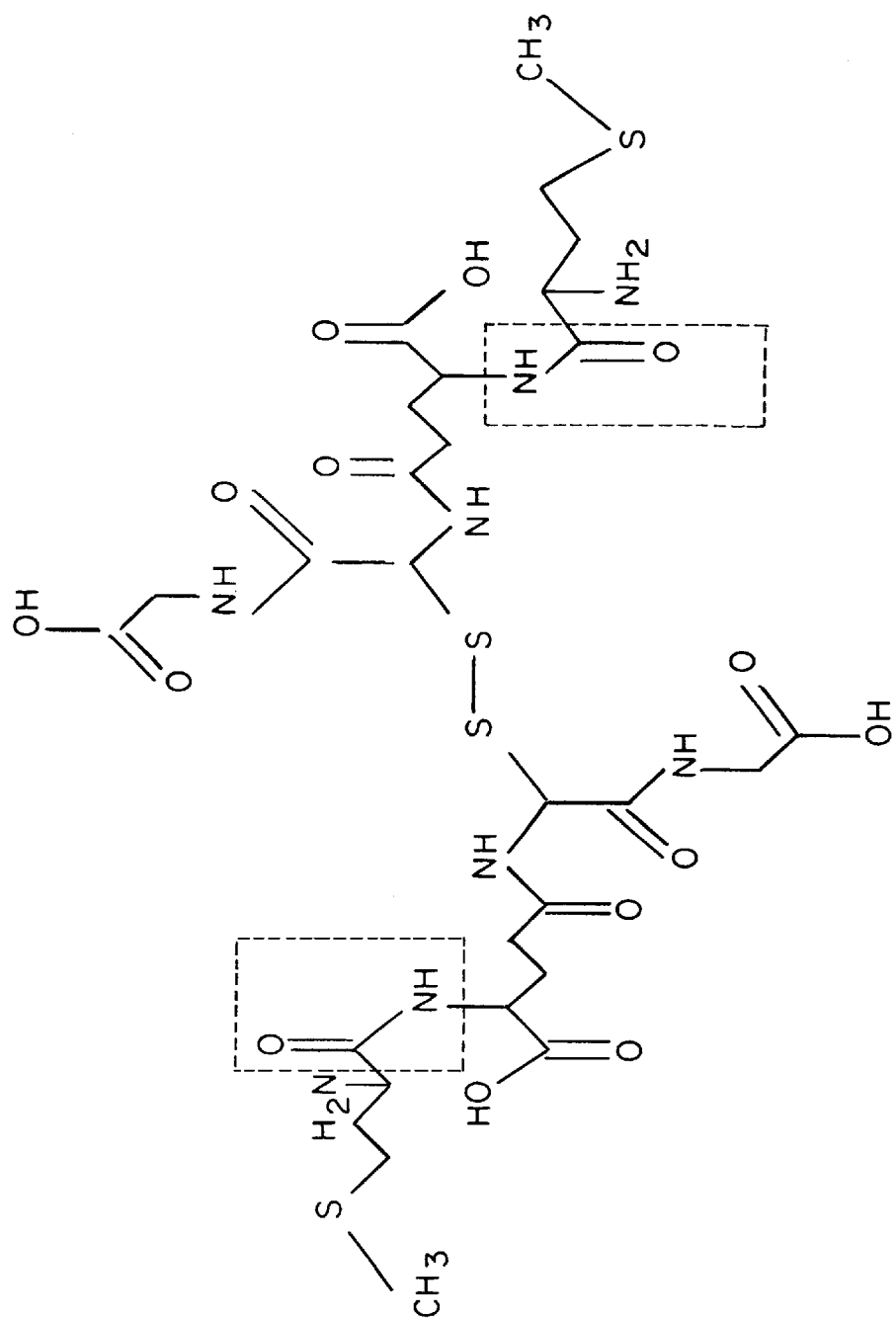
Fig. 7  bis-[L-2-amino-4-[methylthio]butanoic acid]·glutathione disulfide

CYTOKINE AND HEMOPOIETIC FACTOR ENDOGENOUS PRODUCTION ENHANCER AND METHODS OF USE THEREOF

RELATED APPLICATIONS

This application is a continuation-in-part of our U.S. application Ser. No. 733,886, filed Oct. 18, 1996.

FIELD OF THE INVENTION

The present invention relates to medicine and more particularly to pharmacology and therapy, and is intended to be used for preventing and treating various diseases by way of increasing endogenous production of cytokines and hemopoietic factors.

BACKGROUND OF THE INVENTION

It has been known that a number of endogenously produced mammalian humoral factors, i.e. cytokines and hemopoietic factors possess important biological activities that are considerably helpful in treating various human diseases[1,2]. Many of these factors are being tested in man, those with proven efficiency being commercially available as medicinal agents.

The following cytokines and hemopoietic factors are being most extensively researched in oncology: interleukin 2 (IL-2)[3,4], tumor necrosis factor alpha (TNF-α)[5], erythropoietin, macrophage-granulocyte and granulocyte colony-stimulating factors (GM-CSF and G-CSF, respectively[6,7]). No less actively is being studied the use of cytokines and hemopoietic factors for the treatment of infectious disease: interferons (IFN-γ and IFN-β)[8,9,10], colony-stimulating factors[11,12], and the like[13]. Colony-stimulating factors and erythropoietin are broadly used in hematology[14,15].

However, the medicinal use of these exogenously administered agents has its limitations associated with the lack of acceptable drug formulations or their exorbitant cost, a short half-life of these substances in biological media, difficulties in dose finding as well as numerous toxic and allergic effects[16,17], since even the recombinant products are more or less immunogenic to the human organism because of the processing fluctuations in the course of the artificial synthesis.

In this regard, in view of achieving a more invariable and significant therapeutic effect free of adverse reactions, it is preferable to induce the endogenous production of the autologous cytokines and hemopoietic factors immediately within the organism of a subject. The remedial effect due to such intrinsic stimulation is free of all the disadvantages associated with exogenously introduced cytokines and hemopoietic factors.

A number of compounds are currently being evaluated that stimulate endogenous production of cytokines and hemopoietic factors in both experimental and clinical settings. There are universally known cases, including successful ones, of using microbial products for cancer therapy which in recent decades has been shown to be mediated via stimulation of the tumor necrosis factor endogenous production[18]. The products capable of evoking concomitant production of various cytokines and hemopoietic factors have presently come to be known as multi-cytokine inducers. Among these are a killed streptococcal preparation, *Nocardia Opaca,* and other bacterial products[19,20,21]. However, virtually all the substances possessing such capability are either killed microorganisms or microbial products or compounds having irregular composition, which results in their limited medicinal utility or even renders their therapeutic use impracticable. Thus, the problem of finding a medically and pharmaceutically acceptable inducer of the cytokine and hemopoietic factor endogenous production has not heretofore been resolved.

Oxidized glutathione (also known as glutathione disulfide and GSSG) will often be referred to as GSSG in this application.

GSSG is known as a dimmer of tripeptide glutathione (γ-glutamyl-cysteinyl-glycine) where two molecules of the tripeptide with the above structure are linked via a covalent disulfide bond between the cystamine residues. Therefore, both the tripeptide glutathione (glutathione, reduced glutathione, GSH; hereinafter referred to as GSH) and its dimmer GSSG are natural metabolites present in animal tissues and biological fluids. At the same time, the natural blood level of GSSG is not sufficient for inducing the cytokine endogenous production in both normal and pathological conditions.

GSH is known to be one of the most important intermediates in the amino acid metabolism and a factor maintaining the intracellular homeostasis[22,23]. The reducing properties of GSH and its function as a donor of reduction equivalents, which is due to the sulfhydryl moiety of the cystamine residue, are of key importance. This characteristic of GSH is responsible for the substance playing a crucial part in one of the most important intracellular antioxidant systems, consisting of GSH as such and two enzymes of its reversible conversion into GSSG: glutathione peroxidase and glutathione reductase[24,25]. The permanent functioning of said system is essential for inactivating or reducing endogenously generated oxidants as well as active metabolites of foreign substances[26,27].

GSH is also known to participate in detoxification reactions involving a group of enzymes collectively known as glutathione S-transferase[28]. These enzymes are capable of conjugating the GSH molecule with various xenobiotics by forming a bond between the latter and glutathione via the thiol moiety of the cystamine residue of the tripeptide. The subsequent degradation of the conjugate is catalyzed by the γ-glutamyl cycle enzymes, and may vary considerably depending upon the nature of the xenobiotic.

Under natural conditions, GSSG does not accumulate in amounts sufficient for inducing cytokine and hemopoietic factor production, due to a constant reduction of GSSG to GSH. The GSSG reduction to GSH also actively progresses in the intestines and liver upon GSSG oral administration, and as any product made of amino acids, the substance is proteolytically degradable in the gastrointestinal tract.

GSSG is known to be used as a components of a nutritional supplement utilized as an adjunct diet in treating patients[29]. However, being a peptide substance, most of the orally administered GSSG is digested in the gastrointestinal tract with the remainder being reduced in the intestinal and hepatic cells to GSH and not entering the circulation. Therefore, the delivery of GSSG into the organism through the gastrointestinal tract may eliminate the possibility of the realization of its activity as a stimulator of endogenous production of cytokines and hemopoietic factors.

An elevation of the GSH endogenous levels for medicinal utility is known to be suggested for boosting immunity[30] and treating toxemias, poisonings, diabetes, mellitus, cardiovascular, infectious and other disorders[31,32,33]. Possible functions of GSH and GSSG appear in the literature.

Exogenous GSH or its direct (γ-glutamyl-cystamine, n-acetyl-cystamine, and n-acetyl-cystamine-glycine) or indirect (2-oxothiazolidine-4-carboxylate) biochemical precursors, or their salts and esters, are reportedly used as medicinal agents and dietary supplements in treating various diseases[34,35,36,37,38].

GSH is also claimed to be useful as a chemoprotective agent that prevents neurotoxicity in cancer chemotherapy[39] as well as in combination with antineoplastics in order to augment their effect[40].

No reference, however, is currently available to GSSG as a medicine in its own right (sole substance) used to induce the endogenous production of cytokines and hemopoietic factors. The substance is known neither to have medicinal effects in human and animal diseases nor to be applied as a pharmaceutical agent for treating illnesses.

SUMMARY OF THE INVENTION

It is an object of the present invention to provide an active substance, and advantageous combinations of said substance and/or its derivatives with extenders and/or enhancers or modulators of its activity which are capable of inducing endogenous cytokine and hemopoietic factor production to an individual or a subject in need thereof.

"Subject in need thereof" as used in this application is intended to mean a mammal, e.g., man, domestic animals and livestock including cats, dogs, cattle and horses, having one or more manifestations of a disease in which stimulation of endogenous cytokine or hemopoietic factor (or both) production would be considered beneficial by those skilled in the art. "Therapeutic agent" as used in this application is meant to include any drug form of GSSG-containing material or GSSG alone, which has a therapeutic effect on neoplastic, infectious, hematologic, immunologic or other diseases. Therapeutic effect, as will be further defined, indicates any effect in man and other mammals which is beneficial, including curative, preventative, allowing maintenance at a beneficial level, or is in any way advantageous in connection with the body of man and other mammals.

In accordance with the present invention, it is GSSG that upon parenteral administration induces the endogenous cytokine and/or hematopoietic factor production in an individual or subject in need thereof, in both health and disease.

Having performed studies in search for a medically and pharmaceutically acceptable inducer of the cytokine and hemopoietic factor endogenous production, the applicants discovered a new property of a previously known substance, oxidized glutathione (oxidized glutathione, glutathione disulfide, GSSG; hereinafter often referred to as GSSG).

Being administered parenterally or acting on isolated cells, the substance is capable of inducing production of several cytokines and hemopoietic factors in mammals (animals and humans) in both health and disease.

The inducer or stimulator of the endogenous cytokine and hemopoietic factor production is oxidized glutathione (GSSG) which is a dimer of reduced glutathione having the structure γ-glutamyl-cysteinyl-glycine, where the two molecules of the tripeptide are linked via a covalent disulfide bond between the cystamine residues.

According to the invention, a method is provided for stimulating endogenous production of cytokine and hemopoietic factors by introducing to a mammalian body in need of stimulation of cytokine or hemopoietic factor or both, an effective amount of oxidized glutathione for a sufficient period of time to stimulate said endogenous production to obtain a therapeutic effect.

Preferably, the glutathione is introduced parenterally or topically. In a preferred form, the method is carried out by introducing the oxidized glutathione (GSSG) or its derivatives with an extender of half life and/or enhancers or modulators to enhance the desired effect of stimulating endogenous production of cytokines and hemopoietic factors and producing a therapeutic effect in a body.

Preferably, the GSSG derivative is selected from the group of compounds representing a molecule of GSSG chemically modified by binding covalently as for example: with cysteamine-(2-mercaptoethylamine), lipoic acid (6,8-thioctic acid), carnosine (b-alanyl-hystidine), adenosine (9-β-D-ribofaranosyladenine), methionine (2-amino-4-[methylthio]butanoic acid); and both the D and L forms of the amino acids set forth in this paragraph can be used.

Particularly desirable derivatives are GSSG covalently bound either to cysteamine (S-thioethylamine-glutathione disulfide), or to lipoic acid (bis-[6,8-thiooktanil]•glutathione disulfide), or to carnosine ([b-alanyl-hystidil]•glutathione disulfide), or to adenosine ([9-β-D-ribofuranosyladenyl] •glutathione disulfide), or to methionine (bis-[2-amino-4-[methylthio]butanoyl]•glutathione disulfide), or mixtures thereof and including the D and/or L forms of amino acids herein.

Preferably, the extender is selected from the group consisting of pharmaceutically acceptable pro-oxidant compounds, (hydrogen peroxide, ascorbic acid) compounds capable of forming both weak ionic and coordinating links which stabilize molecule of GSSG (dimethyl sulfoxide), or materials which are competitors of NADP-H-dependent reduction of GSSG into GSH catalyzed by glutathione reductase, compounds capable of producing reversible inhibition of reduction of NADP+ into NADP-H catalyzed by glucose-6-phosphate-dehydrogenase or by other NADP-H-dependent enzymes, or mixtures thereof.

Particularly desirable extenders are hydrogen peroxide, inosine, ascorbic acid, dimethyl sulfoxide, or cystamine or mixtures thereof.

Preferably, the enhancer/modulator is selected from the group consisting of methyl moiety donators (such as choline-chloride{[2-hydroxyethyl]trimethylammonium chloride} or S-adenosyl-methionine), representatives of intracellular redox-oxidative pairs (such as lipoic/dehydrolipoic, folic/dehydrofolic, ascorbic/dehydroascorbic acids). An enhancer or modulator or enhancer/modulator as used herein is meant to be a material which increases or changes beneficially in terms of curative outcomes the therapeutic effect of GSSG or its derivatives, but is not an extender of half life of the GSSG.

Particularly desirable enhancers or modulators are choline-chloride, S-adenosyl-methionine, lipoic (6,8-thioctic) and folic (pteroylglutamic) acids.

In the preferred form, GSSG is introduced to the body at a dose of from 0.01 to 0.5 mg of GSSG base per kg of body weight for GSSG base and its salts, and from 0.01 to 1.0 mg for GSSG derivatives, at least one time during each 24 hour period, although it can be continuously injected or otherwise introduced to the body to have a 24 hour total dosage of from 0.01 to 0.5 mg per kg of body weight for GSSG base and its salts, and from 0.01 to 1.0 mg for GSSG derivatives each 24 hour period. Preferably, administration and introduction to the body is carried out until a desired stimulating effect increasing production of cytokines and hemopoietic factors and providing a therapeutic effect is obtained.

According to the invention, a therapeutic agent for treating neoplastic, infectious, hematologic, immunologic and other diseases is provided, comprising an effective amount of oxidized glutathione, along with a pharmaceutically acceptable excipient. Preferably, the oxidized glutathione for parenteral use is in a pharmaceutically acceptable solvent as, for example, an aqueous solution including water, glucose solution, isotonic solutions of sodium chloride, buffered salt solutions. Preferably, a pharmaceutically acceptable extender capable of enhancing and prolonging therapeutic effect as by increasing the half life of oxidized glutathione; or a pharmaceutically acceptable enhancer or modulator of GSSG activity by mechanisms other than increasing the GSSG half life, is used along with the GSSG.

The applicants have for the first time shown that an immediate action of exogenous GSSG or its salts on mammalian (human and laboratory animal) cells capable of producing cytokines and hemopoietic factors, exerts stimulation on the synthesis of these molecules and their increased level in the blood serum (in vivo conditions) or culture media (ex vivo or in vitro conditions). The method suggested can bring about the effect of stimulating production of cytokines and hemopoietic factors, and this effect is elicited by the administration of GSSG into the organism or entering into the cultural media, as well as by the administration of GSSG in combination with pharmacologically active formulations mediating either the prolongation of glutathione's retaining the oxidized form or enhancing or beneficially modulating its activity. The studies performed by the applicants have revealed GSSG and its formulations to possess a therapeutic effect in various experimental and clinical pathological conditions.

The revealed GSSG-induced stimulation of the endogenous cytokine and hemopoietic factor production in the body results in antitumor, anti-infective, hemopoietic, immunomodulatory and other pharmacological effects resulting, in turn, to a greater or lesser extent therapeutic or preventive effect in various diseases.

BRIEF DESCRIPTION OF THE DRAWINGS

The above and other objects, features and advantages of the present invention will be better understood from the following specification when read in connection with the accompanying drawing in which:

FIGS. 3, 4, 5, 6 and 7 are drawings of compounds where GSSG is covalently bound to: to cysteamine (S-thioethylamine-glutathione disulfide, FIG. 3); lipoic acid (bis-[6,8-thioktanyl]•glutathione disulfide, FIG. 4); carnosine ([b-alanyl-hystidyl]•glutathione disulfide, FIG. 5), or to adenosine ([9-β-D-ribofuranosyladenyl]•glutathione disulfide, FIG. 6); methionine (bis-[2-amino-4-[methylthio]butanoyl]•glutathione disulfide, FIG. 7)

DESCRIPTION OF PREFERRED EMBODIMENTS

In accordance with the present invention, the medicinal agent suggested for treating neoplastic, infectious, hematologic, and other diseases, in which stimulation of the endogenous cytokine and hemopoietic factor production is appropriate, has an effective amount of GSSG and/or its pharmaceutically acceptable salts, and/or its pharmaceutically acceptable derivatives as its active principle. It is also advantageous to prepare a drug form of the medicinal agent as an injectable solution containing 0.01 to 2.0% of GSSG base for GSSG itself and its salts, or 0.01 to 4.0% for GSSG derivatives.

Figure 2:
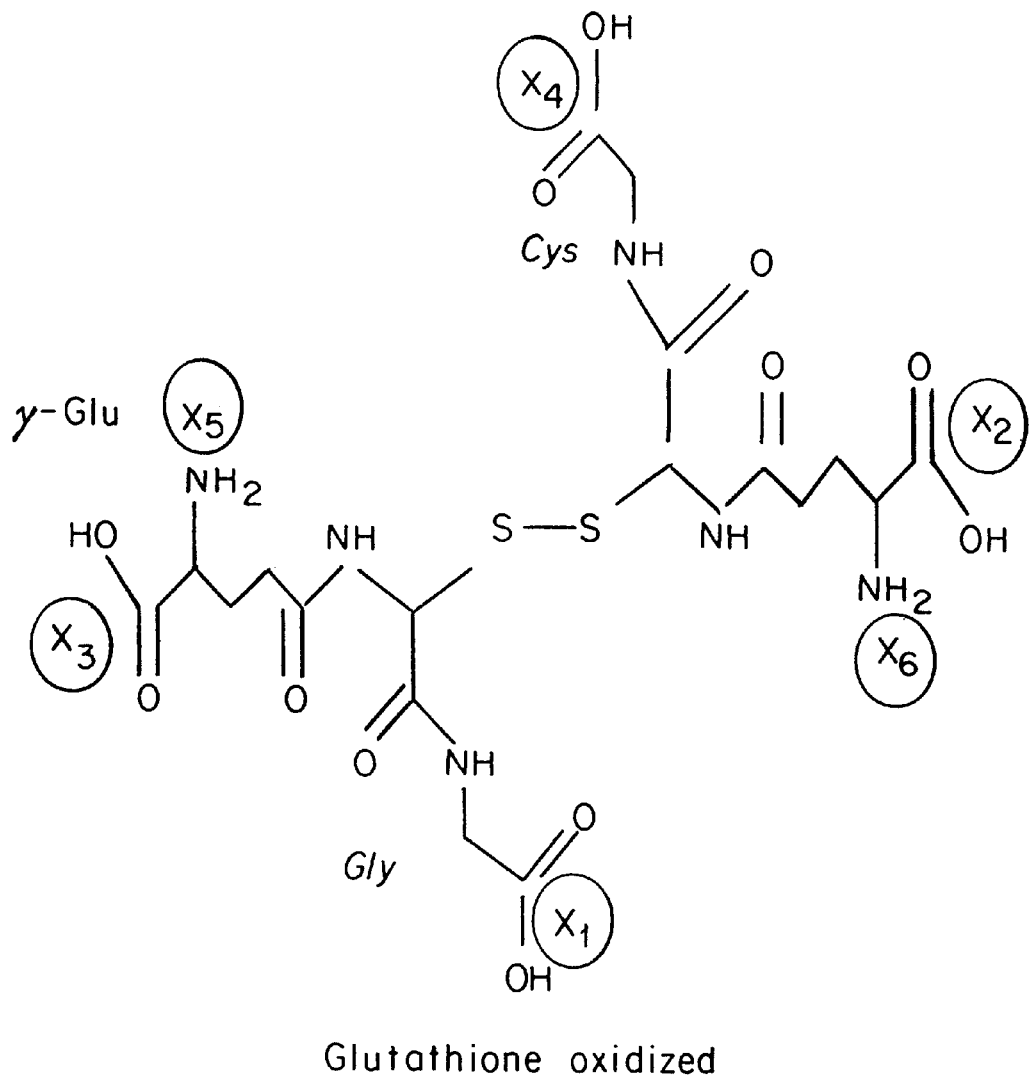
FIG. 2 is a drawing of GSSG structure with notification of sites for chemical modifications when GSSG salts and derivatives are reproduced.

The GSSG used as a therapeutic or medicinal agent in accordance with the present invention is shown in FIG. 2. GSSG and/or its pharmaceutically acceptable salts, and/or its pharmaceutically acceptable derivatives is preferably used in a carrier or solution as, for example, isotonic solution of sodium chloride, glucose solution, other buffer and salt solutions. Any aqueous based or solvent based carrier or solvent can be used as long as the overall solution or dispersion is compatible with the body and pharmaceutically acceptable i.e., it does not cause any unwanted side effects in the body or unwanted interaction with GSSG and/or its pharmaceutically acceptable salts, and/or its pharmaceutically acceptable derivatives.

In the structural formula of FIG. 2, points $X_1$, $X_2$, $X_3$, $X_4$, $X_5$, and $X_6$ are noted as sites for chemical modification of the GSSG. Generally, the GSSG and/or its pharmaceutically acceptable salts, and/or its pharmaceutically acceptable derivatives is used in the form shown in solution or can be any of its physiologically and pharmaceutically acceptable soluble salts. The disodium and dilithium salts where $X_1$, $X_4$, are either sodium ions or lithium ions or a mixture, are preferred for best solubility of the drug. $X_1$, $X_2$, $X_3$, and $X_4$ can each be hydrogen if other substitutes are not used. Other salts of GSSG can be used, so long as they are pharmaceutically acceptable, i.e., do not adversely affect the body, for example, $X_1$, $X_2$, $X_3$, and $X_4$ can all be (or one or more of them can be) potassium, calcium, zinc, molybdenum, vanadium, fluoride, mixtures thereof or any other pharmaceutically acceptable substitutes. Water soluble salts are preferred for use in this invention.

Figure 3:
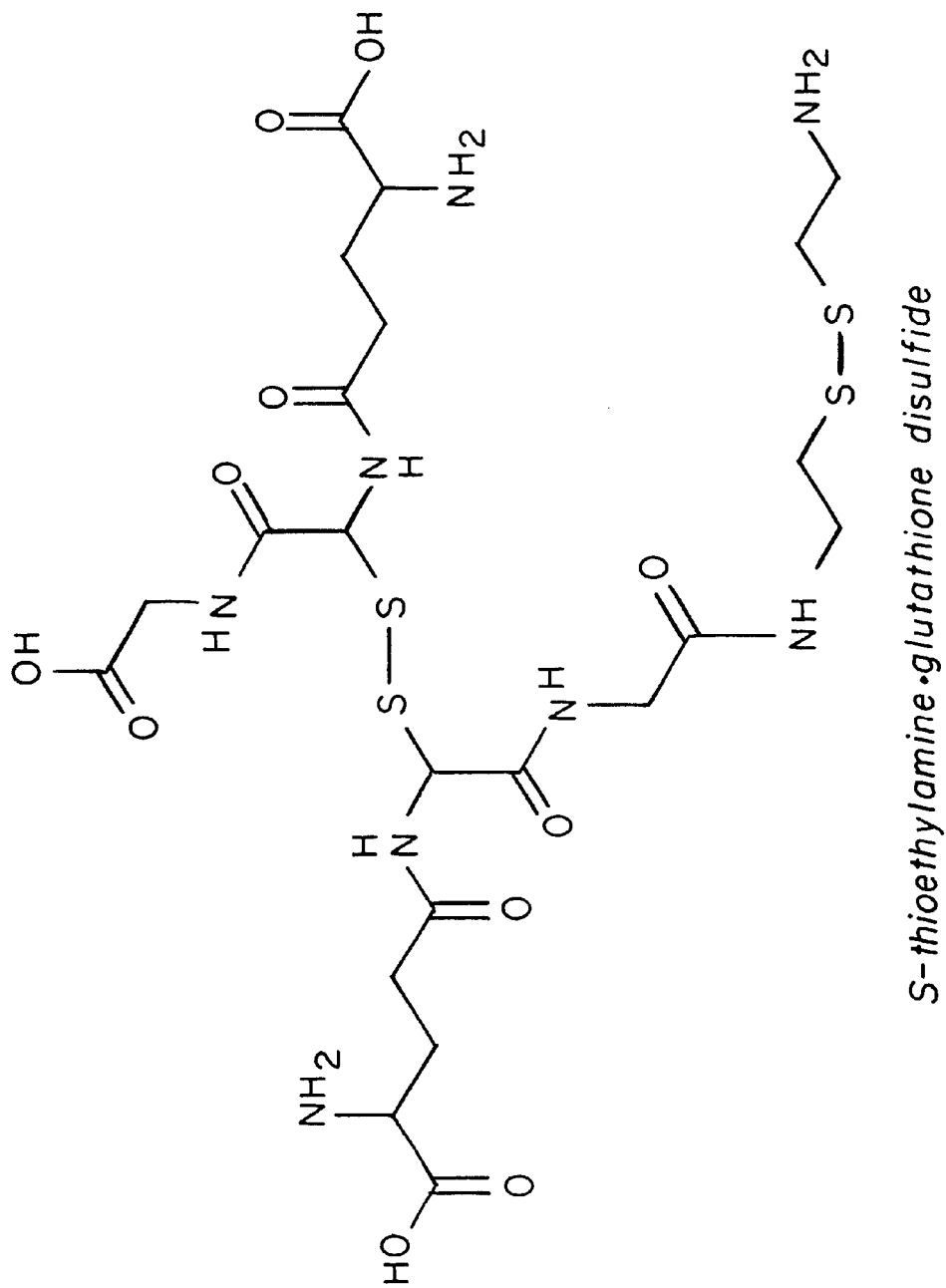
Figure 4:
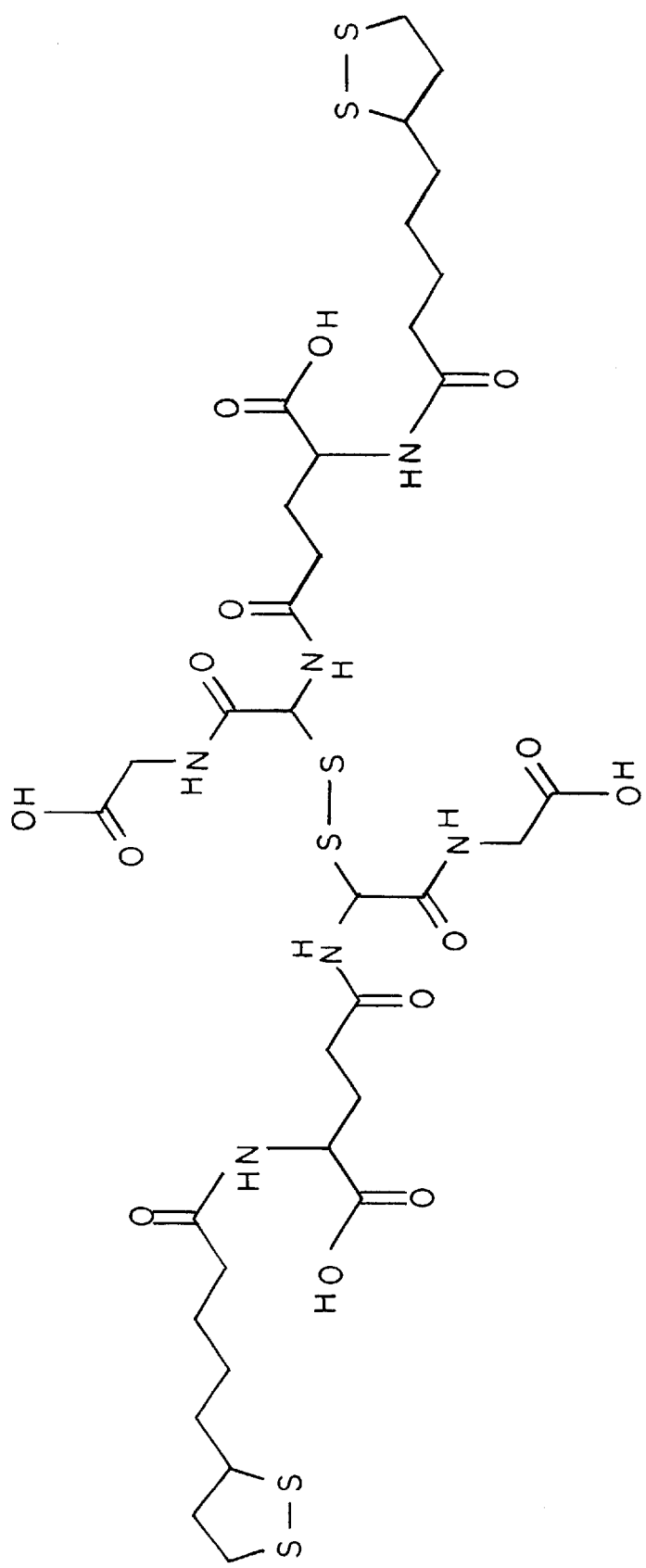
Figure 5:
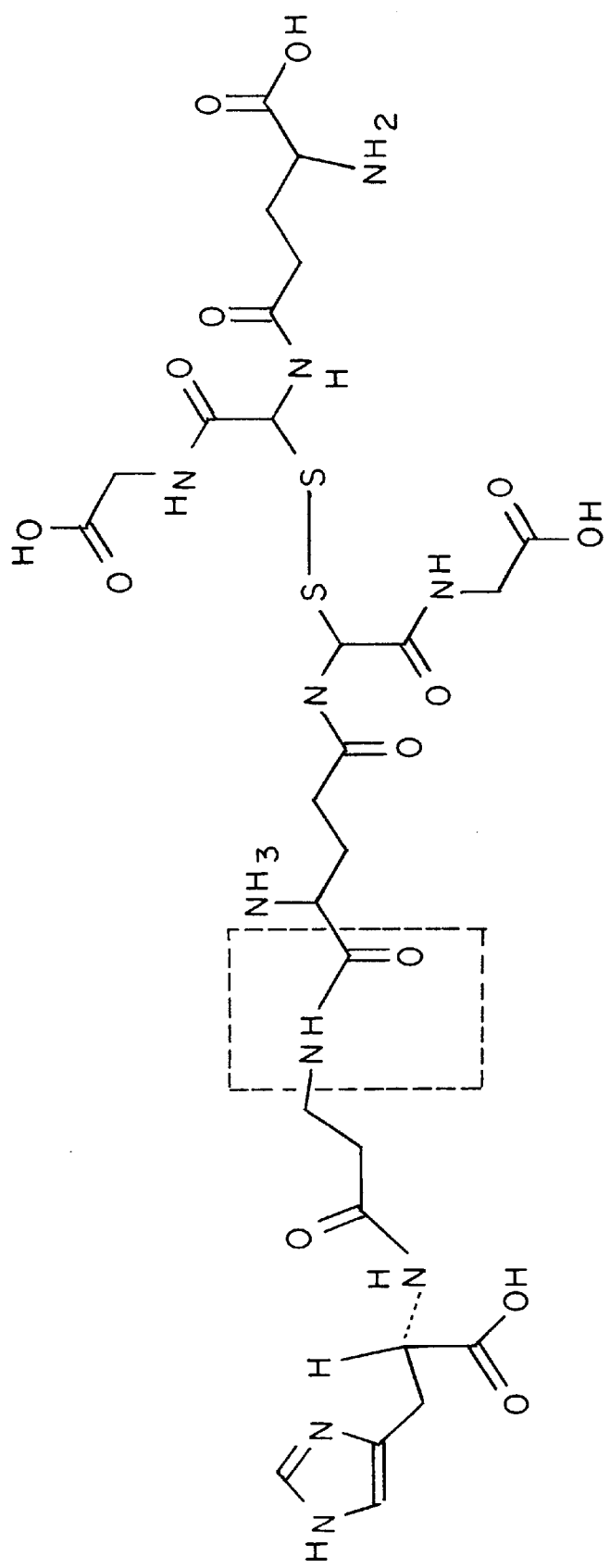
Figure 6:
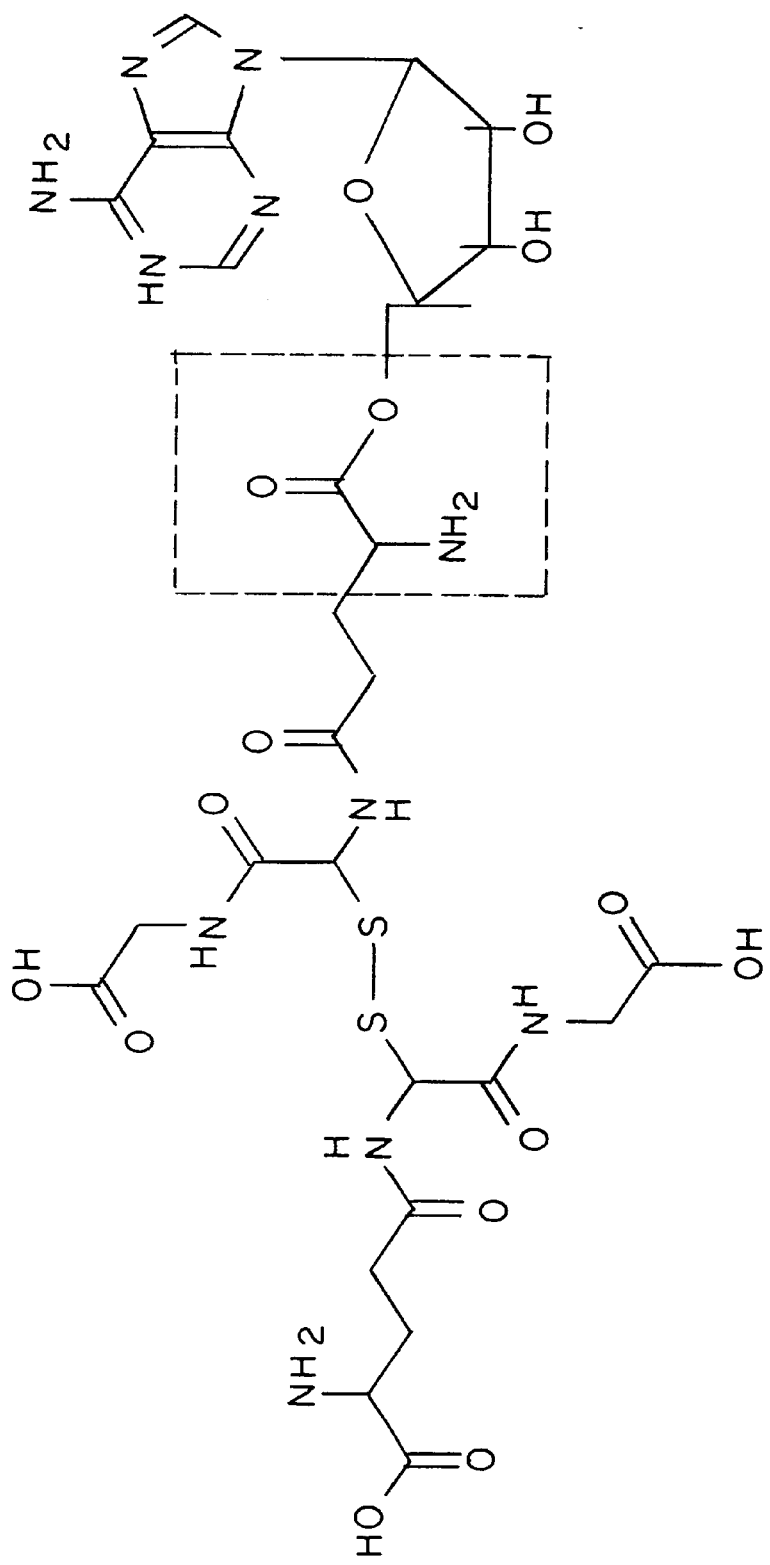

In the structural formula of FIG. 3, points $X_1$ as shown, (or $X_1$, and $X_2$) is noted as a site for covalent binding with cysteamine molecule(s) (2-mercaptoethylamine). In the structural formula of FIG. 4, points $X_5$ as shown or $X_5$, and $X_6$ are noted as sites for covalent binding with molecules of lipoic acid (6,8-thioctic acid). In the structural formula of FIG. 5, point $X_3$ is noted as a site for covalent binding with molecule of carnosine (b-alanyl-hystidine). In the structural formula of FIG. 6, point $X_2$ is noted as site for covalent binding with molecule of adenosine (9-β-D-ribofuranosyladenine). In the structural formula of FIG. 7, points $X_5$ as shown or $X_5$, and $X_6$ are noted as sites for covalent binding with molecules of methionine (2-amino-4-[methylthio]butanoic acid).

In accordance with the present invention, it is expedient to use such GSSG or its derivative drug forms and/or pharmaceutical compositions that either prolong oxidized glutathione half-life in tissues and biological fluids, or augment, or beneficially modulate the revealed biological and therapeutic properties of GSSG.

In accordance with the present invention, with the purpose of augmenting, beneficial modulating, and/or prolonging the therapeutic effect of GSSG, its drug form (injectable solution) is suggested to contain GSSG and/or its derivatives as described above (see FIGS. 3–7) together with pharmaceutically acceptable component (extender, enhancer/modulator), capable of extending the half-life of GSSG and/or its derivatives or enhancing/modulating their biological and therapeutical effects. GSSG and/or its salts, and/or its derivatives can either be present in a single drug form together with the above mentioned extenders, enhancers/modulators (single injectable solution prepared beforehand or ex tempore), or be delivered into the body using separate drug forms: injectable solutions for GSSG and/or its salts, and/or its derivatives and/or derivatives salts; and any pharmaceutically acceptable drug forms, dosage regimens, and administration routes for the above mentioned extenders, enhancers/beneficial modulators.

As a pharmaceutically acceptable GSSG derivative, one of the compounds, or of their pharmaceutically acceptable salts, where GSSG is covalently bound to: either cysteamine (S-thioethylarnine-glutathione disulfide, see FIG. 3 for structural formula), or lipoic acid (bis-[6,8-thiooktanil]•glutathione disulfide, see FIG. 4), or carnosine ([b-alanyl-hystidil]•glutathione disulfide, see FIG. 5), or adenosine ([9-β-D-ribofuranosyladenyl]•glutathione disulfide, see FIG. 6), or methionine (bis-[2-amino-4-[methylthio] butanoyl]•glutathione disulfide, see FIG. 7), can be offered for application.

This is because the presence of one of the aforementioned molecules (cysteamine, lipoic acid, carnosine, adenosine, or methionine) as a constituent part of a modified GSSG molecule, stabilizes structure of the corresponding derivative making it more resistant against proteolysis and/or reduction to GSH. As another way of stabilizing molecule of GSSG, its salts, or its derivatives/derivative salts, and protecting them against proteolysis and/or reduction, a replacement of one or more of L-amino-acids constituting the molecule of both GSSG and the aforementioned derivatives with their D-forms, can be implemented.

All of pharmaceutically acceptable GSSG or derivatives most preferably can be used as the medicinal agents in the injectable form of 1.0% solution with dosage range of from 0.01 to 0.5 mg of GSSG base per kg of body weight for GSSG base and its salts, and from 0.01 to 1.0 mg for GSSG derivatives, with preferable concentration range of from 0.5% to 5.0% one or more times a day, by one or more day pulses or continuously until a desired therapeutic effect has been achieved.

As a pharmaceutical acceptable component or extender to prolong glutathione permanence in oxidized form, 0.003% hydrogen peroxide and/or 5.0% ascorbic acid can be offered for application. This is because in the presence of hydrogen peroxide or ascorbic acid, a donor of reactive oxygen intermediates (that is an oxidant), GSSG is reduced by glutathione reductase to GSH at a lesser speed, thereby conditioning a slower reduction of GSSG introduced exogenously into biological media.

Hydrogen peroxide preferably can be used in amounts of from 0.03 to 0.0003% by weight of solutions used (from 1.0 to 5.0 ml of solutions, regardless whether they contain or do not contain GSSG and/or its salts, and/or its derivatives/derivative salts). Ascorbic acid preferably can be used in amounts of from 0.1 to 10% by weight of solutions used (from 1.0 to 10.0 ml of solutions, regardless whether they contain or do not contain GSSG and/or its salts, and/or its derivatives/derivative salts).

Usage of an acceptable concentration of hydrogen peroxide ($H_2O_2$) and/or ascorbic acid in formulation of the drug form for parenteral administration, as well as usage of any other prooxidant compounds (donors of active oxygen form), makes it possible to realize only one of possible methods of the prolongation of oxidized glutathione and/or its derivative half-life in the biological fluids and tissues and, thereby, to enhance and prolong the pharmaceutical effect of GSSG and/or its derivatives.

We have also found some other pharmaceutically acceptable components or extenders capable of mediating the slowdown of the reduction of exogenous GSSG and/or its derivatives into GSH in biological media. Such, in particular, are: the compounds capable of forming weak ionic and/or coordinating links which stabilize molecules of GSSG, for example, dimethyl sulfoxide; the factors capable of setting up competitive relations with a reduced form of the nicotinamide adenine dinucleotide phosphate or NADP-H, for example, inosine (and other derivatives of hypoxanthine); as well as the agents reversibly inhibiting the processes of reduction of the oxidized form of NADP+ into NADP•H, for example, cystamine (2,2'-Dithio-bis [ethylamine]) and other inhibitors of glucose-6-phosphate-dehydrogenase.

Besides hydrogen peroxide and ascorbic acid, one of other pharmacologically accepted components capable to prolong the oxidized glutathione half-life can be dimethyl sulfoxide, which stabilize GSSG or its derivative molecules by forming both weak ionic and coordinating links with atoms of GSSG. Dimethyl sulfoxide is used most preferably as 7.0% (v/v) solution and preferably as a solution of from 0.1% to 30% by volume (from 1.0 to 30.0 ml of solutions or more when applied epicutaneously/through instillations, regardless whether they contain or do not contain GSSG/GSSG salts and/or its derivatives/derivative salts.

Since reduced NADP-H is the key cofactor of glutathione reductase system catalyzing the reduction of GSSG into GSH, any pharmaceutically acceptable compounds or biophysical influence retarding the reduction of GSSG or blocking biological oxidation of NADP-H by glutathione reductase will facilitate preservation of GSSG/GSSG salts and/or its derivatives/derivative salts from reduction in biological media and, therefore, will enhance and prolong its curative effect.

Due to conducted research we were the first to discover that GSSG pharmaceutical and medicinal effect will reinforce, when GSSG used in combination with agents capable of competition with NADP-H, as well as with compounds reversibly inhibiting the enzymatic reaction, catalyzed by glucose-6-phosphate-dehydrogenase which mediates the reduction of the oxidized form of NADP+. Reversible inhibitors or pentose phosphate pathway of glucose oxidation can be used.

Thus, besides hydrogen peroxide, ascorbic acid and dimethyl sulfide one of other pharmacologically accepted components capable to prolong the oxidized glutathione half-life can be inosine (hypoxanthine-9-D-ribofuranoside) used most preferably as 0.1% solution and preferably as a solution of from 0.1% to 5% by weight (from 1.0 to 5.0 ml of solutions, regardless whether they contain GSSG/GSSG salts and/or its derivatives/derivative salts.

The investigations carried out showed inosine to facilitate biological and therapeutical effects of GSSG. It was demonstrated that this property of inosine is based on its ability to compete with NADP-H, and thereby, to retard GSSG reduction into GSH. Moreover, we have also found that other hypoxanthine derivatives (including inosine, nucleoside ones, hypoxanthine riboside and other nucleoside derivatives of inosine) possess this property as well.

Also, besides hydrogen peroxide, ascorbic acid, dimethyl sulfoxide and inosine, cystamine (2,2'-Dithio-bis [ethylamine]) is another pharmaceutically acceptable agent conditioning a slower reduction of GSSG, if used most preferably as 0.1% solution and preferably as a solution of from 0.1% to 3% by weight (for example 1.0 to 5.0 ml of solutions, regardless of whether they contain GSSG/GSSG salts and/or its derivatives/derivative salts).

Our research showed cystamine to facilitate biological and therapeutical effects of GSSG. The effect is due to the cystamine ability to act as a reversible inhibitor of key enzyme of the pentose phosphate pathway, glucose-6-phosphate-dehydrogenase, mediating reduction of NADP+ into NADP-H.

As pharmaceutically acceptable components capable of enhancing or beneficially modulating biological and therapeutic effects of GSSG and/or its derivatives, several groups of chemical compounds have been shown to augment, diversify or beneficially alter effects of GSSG and/or its derivatives. Therefore several enhancers/beneficial modulators of effects of GSSG/GSSG salts and/or its derivatives/derivative salts can be assigned to the following groups of chemicals.

Donators of methyl groups, such as choline-chloride and S-adenosyl-methionine used in combination with GSSG (and/or its salts/derivatives) have appeared to be more effective compared with GSSG alone (and/or its salts/derivatives) when these agents are used for treating animals with experimental pathologic conditions of immunologic and infectious nature. At that, it has been shown that choline-chloride can be used in patients most preferably as 10% solution and preferably as a solution of from 1.0% to 20% by weight (from 1.0 to 5.0 ml or solutions, regardless whether they contain GSSG or its derivatives). S-adenosyl-methionine can be used in patients most preferably as 5.0% solution and preferably as a solution of from 1.0% to 10% by weight (from 1.0 to 5.0 ml of solutions, regardless whether they contain either GSSG and/or its derivatives).

Compounds, which are capable of formation intracellular redox-oxidative pairs (lipoic, folic and ascorbic acids) have also been found to augment GSSG/derivative effects in inmmunologic, infectious, or other diseases (diabetes mellitus). Lipoic acid can be used in patients most preferably as 0.5% solution and preferably as a solution of from 0.1% to 1.0% by weight (from 1.0 to 5.0 ml of solutions, regardless whether they contain either GSSG and/or its derivatives). Folic acid can be used in patients most preferably as 0.5% solution and preferably as a solution of from 0.1% to 1.0% by weight (from 2.0 to 5.0 ml of solutions, regardless whether they contain either GSSG and/or its derivatives).

Thus, the present invention also suggests the method to enhance or beneficially modulate the ability of GSSG to stimulate endogenous production of cytokines and hemopoietic factor which presupposes the usage a pharmaceutical composition including GSSG and/or its derivatives and an additional component or components able to prolong the oxidized glutathione half-life (extenders) or to enhance/modulate beneficially biological and therapeutical effects of GSSG and/or its derivatives (enhancers/beneficial modulators). GSSG and/or its salts, and/or its derivatives can either be administered combined in a single dosage form with both extenders and enhancers/modulators, or can be delivered into a body separately from both extenders and enhancers/modulators, using different pharmaceutically acceptable administration routes for each constituent of any combination used. This can be achieved for example by the administration of pharmaceutically acceptable compositions including drug forms of GSSG/GSSG salts and/or GSSG derivatives/derivative salts; and pharmaceutically acceptable compositions including drug forms of other products, able to prolong the oxidized glutathione half-life (extenders), and/or able to enhance/modulate beneficially therapeutical effects of GSSG/GSSG salts and/or GSSG derivatives/derivative salts.

As used herein, the term "GSSG derivatives" means either S-thioethylamine-glutathione disulfide, or bis-[6,8-thiooktanyl]•glutathione disulfide, or [b-alanyl-hystidyl]• glutathione disulfide, or [9-β-D-ribofuranosyladenyl]• glutathione disulfide, or bis-[2-amino-4-[methylthio]butanoyl] •glutathione disulfide, with one or more of L-amino-acids constituting the molecule GSSG being replaced with its D-form and given at the same dosage range (of from 0.01 to 1.0 mg/kg).

As used herein, the term "extenders" means hydrogen peroxide preferably 0.003%, ascorbic acid preferably 5.0% or other compounds with oxidant activity; dimethyl sulfoxide preferably 7.0%, or other compounds capable of forming weak ionic and/or coordinating links which stabilize molecule of GSSG; inosine (hypoxanthine-9-D-ribofuranoside) preferably 0.1%, or its derivatives including inosine nucleosides; and also cystamine (2,2'-Ditio-bis[ethylamine] preferably 0.1%, or other compounds, capable to produce reversible inhibition of glucose-6-phosphate-dehydrogenase, the key enzyme of the pentose phosphate pathway.

As used herein, the term "enhancers/beneficial modulators" or "enhancers/modulators" means choline-chloride preferably 10%, S-adenosyl-methione preferably 5.0% or other pharmaceutically acceptable donators of methyl groups; lipoic acid preferably 0.5%; folic acid preferably 0.5% or other compounds, which are capable of formation intracellular redox-oxidative pairs. Any other chemical compound or physical influence, which is capable of enhancing and/or modulating beneficially any biological or therapeutical effects of GSSG/derivatives mentioned in this application should also be considered as "enhancers/modulators."

As used herein, the term "epicutaneously/through instillations" means any physiologically and/or medically acceptable administration route when there is a remedy/medicine application on skin surface or superficial mucous membrane (epicutaneous, or cutaneous, or topical, or local use), or when there is an imtracavitary remedy/medicine use through its introduction into a natural and/or artificial cavity of (or space within) a body, such as stomach, urinary bladder, vagina, rectum, abdominal or pleural cavities, intraarticular space, airways, maxillary sinus, and the like, or any pathological, and/or wound cavity.

It is found that the parenteral (intravenous, intraperitoneal, intramuscular, etc.) administration of GSSG and/or its salts, and/or its derivatives in combination with an extender or enhancer/modulator stimulates endogenous production or TNF-α, IFN-α and IFN-γ, IFN-B, IL-IB, IL-1, IL-2, IL-6, IL-10, G-CSF, colony stimulating factors, erythropoietin, and GM-CSF in organism of experimental animals in a larger degree than with the application of GSSG alone and/or its salts, and/or its derivatives. GSSG and/or its derivatives and any extender or enhancer/modulator can be administered with the use of both the single dosage form or different pharmaceutically acceptable dosage forms (as well as dosage regimens and administration routes) for each constituent of any combination used.

The studies carried out prove the ability of the above mentioned compounds to enhance and/or beneficially alter the biological and therapeutical effects of GSSG and/or salts and/or derivatives, which makes evident the expediency of their use in combination with GSSG and/or salts and/or derivatives, to treat neoplastic, infectious, hematological and other diseases in which stimulation of the endogenous cytokine and hemopoietic factor production is considered beneficial by those skilled in the art.

Thus, in accordance with the present invention, for the purpose of enhancing and prolonging the GSSG therapeutical effect, it is preferred that a final drug formulation of GSSG or its salts or derivatives/derivative salts (1–5 ml of solution for injections) should contain additional pharmaceutically acceptable components able to either prolong the GSSG, salt or derivative half-life in the biological media or to enhance/modulate beneficially their biological or therapeutical effects. Any of proposed pharmaceutically acceptable components can also be administered separately from GSSG and/or its derivatives, with the use of any other pharmaceutically acceptable dosage form, as well as dosage regimen, and route of administration.

These pharmaceutically acceptable components, which are other than GSSG and its derivatives, and their most preferable concentrations and dosages for treating human beings can be the following:

a) 0.003% hydrogen peroxide with the acceptable concentration range of from 0.03 to 0.0003% by weight and dosage range of from 1.0 to 5.0 ml and more when administered epicutaneously or through instillations; 5.0% ascorbic acid with the acceptable concentration range of from 0.1 to 10% by weight and dosage range of from 1.0 to 10.0 ml and more when administered epicutaneously or through instillations; or any other pharmaceutically acceptable pro-oxidant compounds with activity of the donors of reactive oxygen intermediates;

b) 7.0% (v/v) dimethyl sulfoxide with the acceptable concentration range of from 0.1% to 30% by volume and dosage range of from 1.0 to 30.0 ml and more when administered epicutaneously or through instillations; any other pharmaceutically acceptable compounds capable to stabilize GSSG or its derivative molecule by forming both weak ionic and coordinating links with atoms of GSSG;

c) 0.1% inosine (hypoxanthine-9-ribofuranoside) with the acceptable concentration range of from 0.1% to 5.0% by weight and dosage range of from 1.0 to 5.0 ml and more when administered epicutaneously or through instillations; any other pharmaceutically acceptable competitors of NADP-H-dependent reduction of GSSG into GSH catalyzed by glutathione reductase;

d) 0.1% cystamine (2,2'-Dithio-bis[ethylamine]) with the acceptable concentration range of from 0.1% to 3.0% by weight and dosage range of from 1.0 to 5.0 ml and more when administered epicutaneously or through instillations; any other pharmaceutically acceptable compounds able to produce reversible inhibition or reductio of NADP+ into NADP-H catalyzed by glucose-6-phosphate-dehydrogenase or by other NADP-dependent enzymes.

e) 10% choline-chloride with the acceptable concentration range of from 1.0% to 20% by weight and dosage range of from 1.0 to 5.0 ml and more when administered epicutaneously or though instillations; 5.0% S-adenosyl-methionine with the acceptable concentration range of from 1.0% to 10% by weight and dosage range of from 1.0 to 5.0 ml and more when administered epicutaneously or through instillations; any other pharmaceutically acceptable compounds able to serve as donator of methyl groups;

f) 0.5% lipoic acid with the acceptable concentration range of from 0.1% to 1.0% by weight and dosage range of from 1.0 to 5.0 ml and more when administered epicutaneously or through instillations; any other pharmaceutically acceptable compounds able to form intracellular redox-oxidative pairs.

At the same time, the data were obtained to testify the direct antitumor effect of GSSG, GSSG salts or GSSG derivatives administered alone or in combination with the pharmaceutically acceptable compounds prolonging oxidized glutathione half-life in biological media or enhancing/modulating the effects thereof. Moreover, the GSSG or GSSG derivative effect was proved to be different for normal and tumor cells. Our in vitro research with the use of normal and tumor cells revealed that the GSSG or its derivatives alone, or their pharmaceutically acceptable compositions containing extenders and/or enhancers/modulators initiated tumor cell death in apoptosis like manner. In case of normal cells, they did not undergo destruction.

It is an object of the present invention to provide a method for treating neoplastic, infectious, hematologic and other diseases in which stimulation of the endogenous cytokine and hemopoietic factor production is advantageous. The method comprises parenteral administration of GSSG and/or its derivatives as the medicinal agent in the injectable drug form at 0.01 to 0.5 mg of GSSG base per kg body weight or 0.01 to 1.0 mg/kg for GSSG derivatives, one or more times a day, by one or more day pulses or continuously until a desired therapeutic effect has been achieved. It is essential that either GSSG as medicinal agent or its drug forms and/or pharmaceutical compositions be administered strictly parenterally so that to prevent or minimize its deregulation or reduction (to GSH) taking place in the gastrointestinal tract upon oral administration. However, any of proposed pharmaceutically acceptable components such as extenders, enhancers/modulators can also be administered separately from GSSG and/or its derivatives, with the use of any other pharmaceutically acceptable dosage form, as well as a dosage regimen, and a route of administration. At that, the GSSG and/or its derivatives with or without extenders and/or enhancers/modulators can also be applied topically or epicutaneously to the body at a dose consistent with the parenteral and intercavity dose as for example 0.01 to 0.5 mg of GSSG base per square meter of skin or topical areas of the body being treated (with 0.01 to 1.0 mg per square meter for GSSG derivatives).

Provided the GSSG or its derivative molecule is protected from proteolysis and/or reduction to GSH, it would be advantageous to administer the agent orally and/or intralesionally (in situ) (wound, tumor, etc.).

The examples given below confirm that the parenteral (intraperitoneal, intravenous, intramuscular, subcutaneous, etc.) use of GSSG and/or its derivative results in inducing the endogenous production of inter alia TNF-$\alpha$, IFN-$\alpha$ and IFN-$\gamma$, IL-1, IL-2, IL-6, IL-10, erythropoietin, and GM-CSF in mammals, which elicits a significant therapeutic effect in animals and humans suffering from neoplastic or infectious disease, hemopoiesis and immunity suppression of different origin, and other diseases in which stimulation of the endogenous cytokine and hemopoietic factor production would be considered beneficial by those skilled in the art.

From the experimental findings (see Examples) it follows that the previously unknown GSSG capability of inducing the endogenous cytokine and hemopoietic factor production and exerting beneficial effects in various diseases, is not associated with an increase in GSH levels, because GSH testing in a wide range of doses and concentrations has revealed neither stimulation of the endogenous cytokine and hemopoietic factor production nor the therapeutic effect observed with the use of GSSG and/or its derivatives.

GSSG can be used along with other medicaments without causing unwanted interaction in the body. For example, patients treated with known drugs such as lithium, ibuprofen, aminophylline, antibiotics, AZT, calcium antagonists, tamoxifen, hormones, interferon, and others can be treated simultaneously with GSSG, its salts and/or derivatives.

As used herein, the term "therapeutic effect" means any improvement in the condition of a patient or animal treated according to the subject method, including obtaining a preventative or prophylactic effect, or any alleviation of the severity of signs and symptoms of a disease and its sequelae, including those caused by other treatment methods (e.g., chemo- and X-ray therapy), which can be detected by means of physical examination, laboratory or instrumental methods and considered statistically and/or clinically significant by those skilled in the art.

As used herein, the term "prophylactic effect" means prevention of any worsening in the condition of a subject treated according to the method of the invention, as well as prevention of any exacerbation of the severity of signs and symptoms of a disease or its sequelae, including those caused by other treatment methods (e.g. chemo- and X-ray therapy), which can be detected by means of physical examination, laboratory or instrumental methods and considered statistically and/or clinically significant by those skilled in the art.

As used herein, the terms "neoplastic and infectious disease", "hemopoiesis and immunity depression of various origin", and "other diseases" mean any neoplastic and infectious disease, any condition caused or accompanied by the erythroid or myeloid suppression, or a reduction in quantitative or functional immunity parameters, as well as any other disease or pathological condition in which stimulation of the endogenous cytokine and/or hemopoietic factors including but not limited to TNF-α, IFN-α, and INF-γ, IL-1, IL-2, IL-6, IL-10, erythropoietin, and GM-CSF, production would be considered advantageous by those skilled in the art.

The non-limiting examples given below demonstrate feasibility of the invention.

The active principle, the GSSG peptide capable of inducing the endogenous cytokine and hemopoietic factor production, may be obtained by conventional peptide synthesis techniques[41].

Thereby obtained peptide (GSSG) is subsequently used in animals and humans (in vivo) as the GSSG base, or as a pharmaceutically acceptable GSSG salt, or as a pharmaceutically acceptable GSSG derivative in an injectable drug form prepared by dissolving the bulk substance in injectable water, or in any pharmaceutically acceptable solvent, with the resultant concentration of the active compound being 0.01–2.0% by weight of GSSG base for GSSG and its salts (with 0.01 to 4.0% by weight for GSSG derivatives).

For an in vitro use in experimental settings, GSSG or its derivatives may be dissolved in biologically acceptable solvents such as culture media, isotonic saline solutions, glucose solutions and the like. Preferably an aqueous carrier or solvent is used, although and physiological and other solvents or carrier can be used. For topical application, organic solvents or carriers may be used in the form of ointments, pastes, creams or suppositories for body orifice applications.

The drug form for human and animal use should be prepared under sterile and pyrogen-free conditions while exerting every effort to prevent chemical or bacterial contamination, thereby providing a sterile, pyrogen free treating agent or drug form.

The GSSG or its derivatives injectable drug form has been tested in both animal studies and pilot human trials.

The use of the maximum achievable concentration of the GSSG sodium salt solution (10.0%, 100 mg/mL) in injectable water (or in normal saline, or in 0.003% hydrogen peroxide, or in 0.1% cystamine), and the maximum tolerable volumes administered to mice intra-peritoneally (IP<2.0 mL), intravenously (IV, 0.5 mL), and intramuscularly (IM, 0.05 mL), have made it feasible to reach GSSG dosage levels 5000 mg/kg (IP), 1350 mg/kg (IV), and 135 mg/kg (IM), i.e. 1000, 270, and 27 times, respectively, the maximum recommended human dose of 0.5 mg/kg. In none of the cases either animals' deaths or any toxic signs were observed, showing GSSG in injectable drug form to be essentially non-toxic.

The results of nonclinical evaluation of biological, pharmacological, and therapeutical properties of GSSG, we well as its drug forms with or without 0.003% hydrogen peroxide, or 0. 1% inosine, or 0.1% cystamine, are presented in Examples ##1–5.

EXAMPLE #1

Effect of GSSG and its Drug Forms on Cytokine Production by Human Peripheral Blood Mononuclear Leukocytes in vitro Oxidized glutathione (GSSG), as well as its drug forms containing 0.003% hydrogen peroxide, or 0.1% inosine, or 0.1% cystamine, were evaluated for their effect on cytokine production by human peripheral blood mononuclear leukocytes in vitro.

The leukocytic cytokine production was triggered by adding a mitogen, concanavalin A (ConA) to the cell culture immediately after introducing the test substances. In 24 hours of the cellular exposure to ConA and the test articles, the culture supernatants were sampled and stored until cytokine determination at −70° C.

With the aim of evaluating the functional status of the cells and their capacity of responding to the mitogen in the presence of the test articles at each concentration level, the control cell cultures, containing the test articles in identical concentrations, were incubated for 72 hours following the initial concomitant introduction of ConA and the test substances. 16 hours prior to the incubation completion, $^3$H-thymidine was added, and the label rate of incorporation into DNA was interpreted as the criterion of the cellular test system functional state.

Venous blood from male healthy volunteers was collected into plastic heparinized tubes (endotoxin tested). PMNL fraction was isolated by centrifugation in density gradient of Ficoll and sodium diatrizoate (Histopaque-1077; Sigma).

Cell concentration was adjusted to $2\times10^6$ per ml of "complete" culture medium (RPMI 1640, Sigma) containing: HEPES (20 mM); L-glutarine (2mM); Gentamicin (50 μg/mL); fetal calf serum (10%). All the reagents used were of "cell culture tested" grade, Sigma. Cell viability was estimated by the Trypan blue exclusion method and 100 μL of cell suspension (200,000 cells) was placed into each well of flat bottom 96-well sterile micro titer plates for tissue cultures. Cells from each subject were placed into no less than 39 wells.

The five following final concentrations of the test articles (GSSG, as well as its drug forms containing 0.003% $H^2O^2$, or 0.1% inosine, or 0.1% cystamine) were evaluated: 5000 µg/mL; 500 µ/mL; 50 µg/mL; 5 µg/mL; and 0.5 µg/mL. Each concentration was established in no less than 6 wells by adding 50 µL of "complete" medium containing the appropriate quantity of the previously dissolved test articles. Another 6 wells were used for control cultures and contained no GSSG: 50 µL of "complete" medium, or correspondingly, "complete" medium containing 0.003% $H_2O_2$, or 0.1% inosine, or 0.1% cystamine, were added.

Immediately after the test articles had been entered into the cultures, 50 µL of "complete" medium containing ConA (Sigma, cell culture tested) in a quantity required for a final concentration of 4.0 µg/mL, was added to all the wells excepting 3 additional ones which served for evaluation of spontaneous $^3$H-thymidine uptake (without ConA).

After a twenty four hour incubation at 37° C. and 5% of $CO_2$, contents of 3 wells (from each sextuplet of identical wells) were taken out, centrifuged, and the supernatants were frozen and kept at −70° C. until the cytokine assay. Cultures in the other 3 wells (of each sextuplet were incubated further under the conditions described above.

Fifty six hours after the incubation had begun, 1.0 µCi of $^3$H-thymidine was added into all the remaining cultures, the plates were incubated for another 16 hours, and then the contents of the wells were harvested and transferred onto glass-fiber filters which were consequently treated with 5% trichloroacetic acid and ethanol. The filters were dried and their radioactivity (counts per minute, cpm) was determined using liquid scintillation counter, Betaplate 1205 (LKB).

Mean radioactivity values for triplicates of identical cultures were used to calculate the index of mitogenic stimulation: the ratio of averaged cpm values of ConA stimulated cultures to averaged cpm values of unstimulated ones (3 wells without ConA). This stimulation index for wells, where the test articles were present in various concentrations, served as a criterion of cellular functional status, and ability of the cells to respond to mitogenic stimulation.

Supernatants of 24-hour culture triplicates were subsequently assayed for cytokine content only if their 72-hour matched control culture triplicates developed mitogenic response to ConA with value of the stimulation index in the range from 15 to 50. Concentrations of interleukin-1b), interleukin-6 (IL-6), tumor necrosis factor α (TNFα), and interferon α (IFNα) were determined by ELISA using commercial reagent kits (Medgenix, Belgium) and were expressed in pg/mL of culture supernatants.

The salient findings given in Tables 1–4. As can be seen from Tables 1 and 2, the adding of GSSG into the culture media resulted in statistically significant and dose-dependent stimulation of the cytokine production by human mononuclear leukocytes. In addition, the presence of hydrogen peroxide leads to increase control (no GSSG) levels of IL-6 and TNF-α. Besides that, being used in combination with hydrogen peroxide GSSG exerts a more pronounced (1.5–2 fold) stimulatory effect on the production of the cytokines on study: for IL-1β—at 5.0–5000 µg/mn concentration levels; for IL-6 and TNF-α—in the entire concentration range; and for IFN-α—at 500 and 5000 µg/mL.

The application of GSSG in 0.1% inosine solution and 0.1% cystamine solution results in a significant and dose-dependent increase of cytokine production, particularly with respect to IL-6 and TNFα (Tables 3 and 4).

Thus, the GSSG effect on the human peripheral blood mononuclear leukocytes in vitro manifests in considerable stimulation of the cytokine release into culture media, thereby confirming the stimulatory effect of GSSG on the natural cytokine-producing capacity of the human blood cells. The use of GSSG in combination with hydrogen peroxide, inosine, as well as cystamine results in a more prominent effect of GSSG in respect of induction of endogenous cytokine production.

TABLE 1

GSSG effect on in vitro cytokine production by human mononuclear leukocytes. (M ± m)

| GSSG (µg/mL) | Cytokine production (pg/mL) | | | |
| --- | --- | --- | --- | --- |
| | IL-1β | IL-6 | TNFa | IFNa |
| 5000 | 259 ± 36.8* | 2518 ± 264* | 1900 ± 206* | 511 ± 64.1* |
| 500 | 275 ± 39.3* | 2113 ± 132* | 1525 ± 163* | 514 ± 56.2* |
| 50 | 202 ± 24.9* | 1910 ± 205* | 813 ± 90.8* | 407 ± 51.4* |
| 5.0 | 88.5 ± 13.5* | 550 ± 61.3* | 314 ± 44.7* | 109 ± 12.1 |
| 0.5 | 56.0 ± 9.1 | 430 ± 55.6 | 99.1 ± 11.6 | 130 ± 14.9 |
| Control (RPMI) | 46.0 ± 6.8 | 129 ± 12.4 | 88.7 ± 9.3 | 98.3 ± 14.0 |

*differences are statistically significant (p < 0.01) as compared to the control.

TABLE 2

Effect of GSSG in combination with 0.003% hydrogen peroxide on in vitro cytokine production by human mononuclear leukocytes. (M ± m)

| GSSG (µg/mL) | Cytokine production (pg/mL) | | | |
| --- | --- | --- | --- | --- |
| | 1L-1β | 1L-6 | TNFα | IFNα |
| 5000 | 720 ± 81.3* | 4035 ± 518* | 2640 ± 355* | 849 ± 102* |
| 500 | 650 ± 67.1* | 4007 ± 419* | 2100 ± 294* | 905 ± 141* |
| 50 | 511 ± 55.1* | 3859 ± 425* | 1308 ± 164* | 468 ± 69.3* |
| 5.0 | 212 ± 31.7* | 1680 ± 207* | 502 ± 86.4 | 160 ± 37.0 |
| 0.5 | 63.0 ± 7.8 | 851 ± 111 | 318 ± 47.8 | 98.3 ± 18.7 |
| Control (RPMI + 0.003% $H_2O_2$) | 51.0 ± 7.4 | 970 ± 140 | 410 ± 57.0 | 125 ± 20.8 |

*—differences are statistically significant (p < 0.01) as compared to the control.

TABLE 3

Effect of GSSG in combination with 0.1% inosine on in vitro cytokine production by human mononuclear leukocytes. (M ± m)

| GSSG (μg/mL) | Cytokine production (pg/mL) | | | |
|---|---|---|---|---|
| | 1L-1β | 1L-6 | TNFα | IFNα |
| 5000 | 665 ± 73.5* | 5720 ± 498* | 5900 ± 317* | 1010* ± 160.5* |
| 500 | 790 ± 68.85* | 3840 ± 352* | 4520 ± *366 | 1318 ± 152* |
| 50 | 416 ± 44.0* | 4910 ± 205* | 1869 ± 90.8* | 311 ± 51.4* |
| 5.0 | 205.8 ± 18.3* | 2680 ± 196* | 765 ± 67.1* | 117 ± 10.4* |
| 0.5 | 183 ± 20.0* | 1505 ± 138* | 597 ± 48.6* | 66.3 ± 7.8* |
| Control (RPMI + 0.003% $H_2O_2$) | 60.9 ± 5.59* | 131 ± 11.7* | 83.5 ± 9.6* | 89.5 ± 10.0* |

TABLE 4

Effect of GSSG in combination with 0.1% cystamine on in vitro cytokine production by human mononuclear leukocytes. (M ± m)

| GSSG (μg/mL) | Cytokine production (pg/mL) | | | |
|---|---|---|---|---|
| | 1L-1β | 1L-6 | TNFα | IFNα |
| 5000 | 810 ± 75.36* | 4910 ± 503* | 5140 ± 466* | 1060 ± 799* |
| 500 | 540 ± 60.03* | 4000 ± 307* | 3800 ± 307* | 780 ± 180.3* |
| 50 | 490 ± 45.5* | 3800 ± 3183* | 2600 ± 183 | 460 ± 39* |
| 5.0 | 316 ± 30.5* | 2610 ± 207* | 1408 ± 101* | 100 ± 17.7* |
| 0.5 | 155 ± 9.7* | 10 ± 110* | 709 ± 67.3* | 107 6 ± 8.13* |
| Control (RPMI + 0.1% cystamine) | 60.8 ± 6.55* | 65.4 ± 77.0* | 377 ± 28.9* | 114 ± 10.01* |

*—differences are statistically significant ($p < 0.01$) as compared to the control.

EXAMPLE #2

Effect of GSSG and its Drug Forms on Cytokine and Hemopoietic Factor Production as Well as on Hemopoiesis and Immunity Parameters in Cyclophosphamide-induced Hemo- and Immunodepression Both oxidized (GSSG) and reduced (OSH) glutathione, as well as GSSG drug forms containing 0.003% hydrogen peroxide, or 0.3% inosine, or 0.1% cystamine, were evaluated in a murine model of hemo- and immunodepression induced by a single administration of cytostatic cyclophosphamide (CP).

The study was designed to evaluate the effect of a 5-day long administration of the test articles on the capability of the CP-treated murine splenocytes to produce IL-2 and GM-CSF in vitro. In addition, the number of blood leukocytes and lymphocytes and the bone marrow cellularity (number of karyocytes) were determined at 8 days after CP administration. Some animals receiving CP were then challenged with sheep red blood cells (SRBC), and the humoral immune response to the antigen was evaluated.

Male CBA mice (18 to 20 g body weight) were given a single intraperitoneal injection of CP in a dose of 50 mg/kg. Five groups of animals (with no less than 15 mice in each) were formed. Group description is represented below.

Control groups:
1—intact animals receiving a single injection of normal saline (NS) instead of CP injection, which further were treated with test article vehicle (normal saline);
2—control animals receiving a single CP injection, which further were treated with test article vehicle (normal saline);
3—animals receiving a single CP injection, which further were treated with s reference article (GSH dissolved in normal saline) in a dose of 5 mg/kg;

Test groups:
4—animals receiving a single CP injection, which further were treated with the test article (GSSG dissolved in normal saline) in a dose of 5 mg/kg;
5—animals receiving a single CP injection, which further were treated with a variant of the test article drug form (GSSG dissolved in normal saline containing 0.003% $H_2O_2$) with a GSSG dose of 5 mg/kg;
6—animals receiving a single CP injection, which further were treated with a variant of the test article drug form (GSSG dissolved in normal saline containing 0.1% inosine) with a GSSG dose of 5 mg/kg;
7—animals receiving a single CP injection, which further were treated with a variant of the test article drug form (GSSG dissolved in normal saline containing 0.1% cystamine) with a GSSG dose of 5 mg/kg;

Twenty four hours after the CP injection, 5 animals in each group were immunized with SRBC (107 cells in 0.5 mL of NS, intraperitoneally).

On day 3 after the CP injection (24 hours after the immunization) the intraperitoneal injections of the test or reference articles were started (as it has been described above). Injections were performed during 5 days: once a day, daily.

Twenty four hours after the completion of 5 day treatment course (on the 8th day after the CP injection), mice were euthanized and splenocyte cultures were aseptically prepared for assessment of spontaneous production of IL-2 and GM-CSF by the spleen lymphocytes in vitro.

Simultaneously, blood and marrow samples were collected for blood leukocyte and lymphocyte, and marrow nucleated cell counted.

Serum samples from immunized animals were tested on level of SRBC agglutinins (the day 8 after the CP injection, and the day 7 after the immunization).

Table #5 shows the parameters of IL-2 and GM-CSF production by splenocytes, bone marrow and blood cellular indices, and the immune response to sheep red blood cells in mice receiving the test articles against the background of cyclophosphamide induced hemo- and immunodepression.

As is seen from the data, the use of both GSSG and GSSG solution in hydrogen peroxide brings IL-2 and GM-CSF splenocytic production almost back to normal whereas GSH shows no such effect. Also, both GSSG and its hydrogen peroxide solution exert a significant restorative effect on the bone marrow and blood parameters as well as immune response to SRBC.

Tables ##6 and 7 give data on effects of pharmacologically active compositions containing GSSG (in combination with 0.1% of inosine, or 0.1% cystamine) on tested parameter variations in mice with CP-induced hemo- and immunodepression. The findings show significant enhancing GSSG effects by inosine and cystamine components with respect of IL-2b and GM-CSF production stimulation and restoration of bone marrow and blood cellularity. As it could be seen, GSH did not exhibit such stimulation. The maximum stimulation was achieved with the combination of GSSG and 0.1% inosine.

Thus, the use of the subject method in CP-induced hemo- and immunocompromised animals results in a prominent stimulation of IL-2 and GM-CSF endogenous production together with restoration of the bone marrow and blood cellular indices as well as immune response development to sheep red blood cells.

TABLE 5

Effect of the test articles on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSGO + $H_2O_2$ |
| IL-2 production by splenocytes, (U/mL) | 10 | 39.7 ± 5.4 | 11.1 ± 3.0* | 17.2 ± 3.5* | 28.1 ± 3.9[#@] | 34.7 ± 5.1[#@] |
| GM-CSF production by splenocytes, (colonies/$10^5$ cells) | 10 | 180.0 ± 14.2 | 34.3 ± 9.1* | 58.2 ± 7.2* | 129.1 ± 13.4[#@] | 170.1 ± 16.9[#@] |
| Blood leukocyte count, $10^9$/L | 10 | 11.9 ± 1.81 | 4.7 ± 1.25* | 5.2 ± 1.36* | 8.5 ± 0.81[#@] | 9.4 ± 1.40[#@] |
| Blood lymphocyte count, $10^9$/L | 10 | 7.4 ± 0.85 | 3.1 ± 0.56* | 4.3 ± 1.13* | 6.2 ± 1.28[#] | 6.8 ± 1.04[#] |
| Bone marrow nucleated cell number, $10^6$/L | 10 | 53.7 ± 8.7 | 23.8 ± 5.0* | 32.2 ± 4.4* | 45.4 ± 3.9[#@] | 52.3 ± 4.7[#@] |
| SRBC agglutinin titer ($\log_2$) | 5 | 5.33 ± 0.74 | 1.47 ± 0.35* | 1.94 ± 0.34* | 3.68 ± 0.59*[#] | 4.12 ± 0.37*[#] |

Differences are statistically significant (p < 0.05) as compared:
*to the group of intact animals;
[#]to the control group (CP + normal saline);
[@]to the group of animals treated with GSH.

TABLE 6

Effect of GSSG in combination with 0.1% inosine on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSG + 0.1% inosine |
| IL-2 production by splenocytes, (U/mL) | 10 | 34.4 ± 4.2 | 92 ± 1.9* | 15.3 ± 2.7* | 29.8 ± 3.158[#@] | 39.7 ± 4.8[#@] |

TABLE 6-continued

Effect of GSSG in combination with 0.1% inosine on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSG + 0.1% inosine |
| GM-CSF production by splenocytes, (colonies/$10^5$ cells) | 10 | 168.0 ± 14.9 | 25.5 ± 4.2* | 63.4 ± 7.8* | 143 ± 15.06#@ | 196.3 ± 16.6#@ |
| Blood leukocyte count, $10^9$/L | 10 | 123 ± 14 | 5.03 ± 0.85* | 6.3 ± 0.05* | 9.5 ± 1.01#@ | 10.1 ± 1.36#@ |
| Blood lymphocyte count, $10^9$/L | 10 | 8.2 ± 0.09 | 2.8 ± 0.67* | 4.6 ± 0.78* | 6.7 ± 0.81# | 7.18 ± 0.74# |
| Bone marrow nucleated cell number, $10^6$/L | 10 | 61.3 ± 8.05 | 19.7 ± 2.9* | 36.4 ± 4.5* | 48.99 ± 5.14#@ | 69.4 ± 17.7#@ |
| SRBC agglutinin titer ($\log_2$) | 5 | 6.03 ± 0.71 | 1.05 ± 0.28* | 1.62 ± 0.27* | 4.08 ± 0.58*# | 5.13 ± 053*# |

Differences are statistically significant ($p < 0.05$) as compared:
*—to the group of intact animals; #—to the control group (CP + normal saline); @—to the group of animals treated with GSH.

TABLE 7

Effect of GSSG in combination with 0.1% cystamine on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSG + 0.1% cystamine |
| IL-2 production by splenocytes, (U/mL) | 10 | 43.5 ± 4.01 | 14.0 ± 2.7* | 20.3 ± 2.6* | 30.9 ± 3.03#@ | 38.8 ± 4.53#@ |
| GM-CSF production by splenocytes, (colonies/$10^5$ cells) | 10 | 190.5 ± 18.4 | 42.0 ± 5.7* | 66.7 ± 7.8* | 137.0 ± 13.09#@ | 183.7 ± 17.8#@ |
| Blood leukocyte count, $10^9$/L | 10 | 12.3 ± 1.28 | 4.95 ± 0.88* | 6.2 ± 1.06* | 7.8 ± 0.84#@ | 10.5 ± 1.56#@ |
| Blood lymphocyte count, $10^9$/L | 10 | 8.2 ± 0.72 | 3.6 ± 0.63* | 5.31 ± 0.77* | 7.2 ± 0.96# | 7.8 ± 0.84# |
| Bone marrow nucleated cell number, $10^6$/L | 10 | 61.3 ± 5.9 | 28.5 ± 4.2* | 36.4 ± 4.5* | 48.9 ± 5.14#@ | 56.7 ± 4.91#@ |
| SRBC agglutinin titer ($\log_2$) | 5 | 6.03 ± 0.60 | 1.78 ± 0.36* | 2.09 ± 0.37* | 4.08 ± 0.57*# | 4.29 ± 0.41*# |

Differences are statistically significant ($p < 0.05$) as compared:
*—to the group of intact animals; #—to the control group (CP + normal saline); @—to the group of animals treated with GSH.

EXAMPLE #3

Effect of GSSG and its Drug Forms on Cytokine and Hemopoietic Factor Production as Well as on Hemopoiesis and Immunity Parameters in Radiation-Induced Hemo- and Immunodepression Both oxidized (GSSG) and reduced (GSH) glutathione, as well as GSSG drug forms containing 0.003% hydrogen peroxide, or 0.1% inosine, or 0.1% cystamine, were evaluated in a murine model of hemo- and immunodepression induced by a single irradiation in a total dose of 1 Gy.

The study was designed to evaluate efficacy of 7-day daily administration of the test articles (with the dosing started 2 hours post-exposure) on the capability of the splenocytes from mice exposed to radiation to produce IL-2 and GM-CSF in vitro. In addition, the number of blood leukocytes and lymphocytes and the spleen and bone marrow cellularity (number of karyocytes), as well as splenic and medullary colony-stimulating capacity, were determined at 8 days post-exposure.

Male CBA mice (18 to 20 g body weight) were irradiated with single dose of 180 kV X-rays filtered with 0.5 mm Cu (at 15 mA, distance—70 cm, duration 2 min. and 28 sec.). The total absorbed dose comprised approximately 1 Gy.

Five groups of animals (with no less than 12 mice in each) were formed. Group description is represented below.
Control groups:
  #1—intact animals receiving a sham irradiation procedure to reproduce a stress impact, which further were treated with test article vehicle (normal saline);
  #2—control animals irradiated in a dose of 1 Gy, which further were treated with test article vehicle (normal saline);
  #3—animals irradiated in a dose of Gy, which further were treated with s reference article (GSH dissolved in normal saline) in a dose of 5 mg/kg;
Test groups:
  #4—animals irradiated in a dose of Gy, which further were treated with the test article (GSSG dissolved in normal saline) in a dose of 5 mg/kg;

5—animals irradiated in a dose of Gy, which further were treated with a variant of the test article drug form (GSSG dissolved in normal saline containing 0.003% $H_2O_2$) with a GSSG dose of 5 mg/kg;

6—animals irradiated in a dose of Gy, which further were treated with GSSG in normal saline containing 0.1% inosine) with a GSSG dose of 5 mg/kg;

7—animals irradiated in a dose of 1 Gy, which further were treated with GSSG in normal saline containing 0.1% cystamine) with a GSSG dose of 5 mg/kg;

Two hours after the irradiation the intraperitoneal injections of the test or reference articles were started (as it has been described above). Injections were performed during 7 days: once a day, daily.

Twenty four hours after the completion of 7 day treatment course (on the 8th day after the irradiation), mice were euthanized and splenocyte cultures were aseptically prepared for assessment of spontaneous production of IL-2 and GM-CSF by the spleen lymphocytes in vitro.

Simultaneously, blood, spleen and marrow samples were collected for blood leukocyte and lymphocyte, and spleen and marrow nucleated cell counting.

Additionally, hemopoietic colony formation ability of spleen and bone marrow cells was assessed by the method of direct count of colony forming units (CFU) in the spleens of irradiated CBA mice receiving intravenously spleen or bone marrow cells obtained from animals of control or test groups.

Splenocytic IL-2 and GM-CSF levels, blood, bone marrow, and spleen cellular indices as well as colony-stimulating capacity numbers (colony-forming units, CFU) in the bone marrow and spleen of the irradiated animals at 8 days post-exposure, are summarized in Tables 8, 9, 10.

TABLE 8

Effect of the test articles on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals | | | |
|---|---|---|---|---|---|---|
| | | | Normal saline | GSH | GSSG | GSSGO + $H_2O_2$ |
| IL-2 production by splenocytes, (U/mL) | 12 | 41.2 ± 4.4 | 5.0 ± 0.5* | 8.6 ± 1.3* | 25.1 ± 4.9*#@ | 37.1 ± 3.4#@ |
| GM-CSF production by splenocytes, (colonies/$10^5$ cells) | 12 | 120.2 ± 12.4 | 20.7 ± 8.6* | 31.8 ± 3.9* | 93.1 ± 11.5#@ | 106.4 ± 5.2#@ |
| Blood leukocyte count, $10^9$/L | 12 | 12.7 ± 1.3 | 3.4 ± 0.9* | 4.8 ± 0.8* | 8.7 ± 1.3*#@ | 10.7 ± 2.0#@ |
| Blood lymphocyte count, $10^9$/L | 12 | 7.9 ± 0.7 | 2.2 ± 1.3* | 3.4 ± 0.6* | 5.9 ± 0.8#@ | 6.9 ± 0.8#@ |
| Spleen nucleated cell number, $10^7$/L | 12 | 9.8 ± 1.5 | 4.8 ± 1.3* | 4.3 ± 1.5* | 7.7 ± 1.2#@ | 8.2 ± 2.0#@ |
| Bone marrow nucleated cell number, $10^6$/L | 12 | 45.1 ± 3.2 | 14.0 ± 1.0 | 17.2 ± 3.5* | 33.3 ± 5.2*#@ | 37.0 ± 4.0#@ |
| Bone marrow CFU | 12 | 59.4 ± 3.2 | 11.6 ± 2.2* | 22.1 ± 3.6* | 44.3 ± 3.9*#@ | 49.3 ± 3.9#@ |
| Spleen CFU | 12 | 93.2 ± 4.1 | 40.0 ± 5.4* | 56.3 ± 6.8* | 88.3 ± 6.8#@ | 87.6 ± 4.7#@ |

Differences are statistically significant ($p < 0.05$) as compared:
*to the group of intact animals;
to the control group (CP + normal saline);
@to the group of animals treated with GSH.

TABLE 9

Effect of GSSG in combination with 0.1% cystamine on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals | | | |
|---|---|---|---|---|---|---|
| | | | Normal saline | GSH | GSSG | GSSG + 0.1% cystamine |
| IL-2 production by splenocytes, (U/mL) | 12 | 45.4 ± 4.2 | 5.6 ± 0.71* | 9.3 ± 1.44* | 29.3 ± 3.18*#@ | 40.1 ± 4.10#@ |
| GM-CSF production by splenocytes, (colonies/$10^5$ cells) | 12 | 132 ± 11.8 | 28.6 ± 4.5* | 34.3 ± 3.99* | 103 ± 11.6#@ | 113 ± 9.07#@ |

TABLE 9-continued

Effect of GSSG in combination with 0.1% cystamine on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals Normal saline | GSH | GSSG | GSSG + 0.1% cystamine |
|---|---|---|---|---|---|---|
| Blood leukocyte count, $10^9$/L | 12 | 13.3 ± 1.08 | 3.1 ± 0.9* | 5.7 ± 0.9* | 9.3 ± 4.5*#@ | 11.2 ± 1.83#@ |
| Blood lymphocyte count, $10^9$/L | 12 | 8.6 ± 0.74 | 3.38 ± 0.61* | 4.6 ± 0.70* | 6.79 ± 0.82#@ | 7.12 ± 0.899#@ |
| Spleen nucleated cell number, $10^7$/L | 12 | 10.5 ± 0.97 | 5.8 ± 0.9* | 6.93 ± 0.85* | 8.9 ± 1.07#@ | 10.7 ± 1.13#@ |
| Bone marrow nucleated cell number, $10^6$/L | 12 | 48.3 ± 3.8 | 15.1 ± 1.69* | 24.7 ± 3.0* | 39.5 ± 4.17*#@ | 51.0 ± 4.81#@ |
| Bone marrow CFU | 12 | 61.3 ± 5.2 | 16.0 ± 2.5* | 25.6 ± 3.99* | 50.3 ± 5.14*#@ | 55.7 ± 5.31#@ |
| Spleen CFU | 12 | 104 ± 9.2 | 43.5 ± 5.8* | 66.3 ± 7.07* | 94.0 ± 8.81#@ | 107 ± 11.7#@ |

Differences are statistically significant (p < 0.05) as compared:
*—to the group of intact animals; #—to the control group (CP + normal saline); @—to the group of animals treated with GSH.

TABLE 10

Effect of GSSG in combination with 0.1% inosine on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals Normal saline | GSH | GSSG | GSSG + 0.1% inosine |
|---|---|---|---|---|---|---|
| IL-2 production by splenocytes, (U/mL) | 12 | 45.1 ± 4.3 | 4.6 ± 0.53* | 9.9 ± 1.08* | 26.9 ± 3.4*#@ | 44.3 ± 4.71#@ |
| GM-CSF production by splenocytes, (colonies/$10^6$ cells) | 12 | 132 ± 11.9 | 21.8 ± 3.7* | 35.9 ± 4.15* | 116 ± 11.7#@ | 163 ± 22.1#@ |
| Blood leukocyte count, $10^9$/L | 12 | 12.0 ± 1.4 | 3.04 ± 0.81* | 4.95 ± 0.62* | 7.93 ± 0.96*#@ | 10.9 ± 2.04#@ |
| Blood lymphocyte count, $10^9$/L | 12 | 8.15 ± 0.76 | 1.94 ± 0.51* | 4.0 ± 0.58* | 6.7 ± 0.83#@ | 7.8 ± 0.86#@ |
| Spleen nucleated cell number, $10^7$/L | 12 | 9.91 ± 1.3 | 3.5 ± 0.66* | 5.5 ± 0.70* | 9.0 ± 1.13#@ | 10.2 ± 1.5#@ |
| Bone marrow nucleated cell number, $10^6$/L | 12 | 47.3 ± 3.18 | 13.0 ± 1.8* | 22.5 ± 3.08* | 39.9 ± 4.5*#@ | 51.7 ± 4.98#@ |
| Bone marrow CFU | 12 | 56.2 ± 4.4 | 9.7 ± 1.3* | 25.3 ± 3.7* | 48.9 ± 5.13*#@ | 69.0 ± 7.03#@ |
| Spleen CFU | 12 | 154 ± 9.45 | 35.0 ± 5.14* | 59.8 ± 6.18* | 99.3 ± 10.11#@ | 167.0 ± 17.3#@ |

Differences are statistically significant (p < 0.05) as compared:
*—to the group of intact animals; #—to the control group (CP + normal saline); @—to the group of animals treated with GSH.

As is evident from the data of the tables, administration of GSSG, or its drug forms containing 0.003% hydrogen peroxide, or 0.1% inosine, or 0.1% cystamine, results in statistically significant recovery of IL-2 and GM-CSF production by splenocytes, whereas GSH produces no significant effect.

Furthermore, both GSSG alone and its pharmacologically active compositions exerted a significant normalizing effect on the blood, spleen, and bone marrow cellularity. In several instances the effect of GSSG dissolved in hydrogen peroxide has been found to be more prominent. For example, while GSSG per se exhibited no statistically significant effect (as compared to controls) on IL-2 splenocytic production, blood leukocytes, bone marrow cellularity, and bone marrow colonies, GSSG in hydrogen peroxide did produce a statistically meaningful effect. If compared with hydrogen peroxide, both inosine and cystamine were found to exert more prominent effect of enhancing the GSSG action, with the maximal effect being achieved in case of active composition of GSSG with inosine.

Thus, the use of the subject method in animals developed radiation-induced hemo- and immunodepression results in pronounced stimulation of the endogenous IL-2 and GM-CSF production, and also leads to an accelerated recovery of the cellular compositions of the blood, lymphoid and hemopoietic organs as well as colony-forming activity of the bone marrow and spleen.

EXAMPLE #4

Effect of GSSG and its Drug Forms on the Process of Proliferation and Apoptosis of Normal and Tumor Cells The ability of oxidized glutathione (GSSG), as well as its drug forms containing 0.003% hydrogen peroxide, or 0.1% inosine or 0.1% cystamine, to influence processes of a cellular proliferation and/or death was evaluated using normal or tumor cells. To this end, GSSG, or its drug forms had been incubated for 24 hours with cells of myeloid line HL-60 and normal human lymphocytes isolated form peripheral blood of healthy volunteers. Subsequent evaluation of the cell cycle parameters was carried out by the flow cytofluorometry technique.

Venous blood of a healthy volunteer was collected into heparinized test-tubes which had been tested for endotoxin. A mononuclear fraction of blood leukocytes were obtained by centrifugation in gradient of fikoll-metrizoat (Histopaque, Sigma). Cell concentration was adjusted to $2\times10^6$ cells per 1 ml of "complete" cell culture medium (RPMI 1640), containing 20 mM HEPES, 2 mM glutamine, 50 µg/mL gentamicin and 10% fetal calf serum. Cell viability was estimated by the Trypan blue exclusion method, then the cell suspension was placed into wells of 96-well microtiter plates—200,000 cells per well. Cells of HL-60 line were grown in RPMI-1640 medium with the addition of 10% fetal calf serum. Cultivation was carried out in closed flasks, the medium volume was 12 mL, it was changed every four days by centrifugation. The nature of the cells growth was suspensive. Evaluation of the test solution of GSSG (5000 µg/mL), as well as GSSG solutions containing 0.003% hydrogen peroxide, or 0.1% cystamine, was carried out using 6 cellular samples of normal lymphocytes and HL-60 cells for each test solution. 50 µL of each test solution were added to one or the other cell culture and thereafter cells were cultivated for 24–96 hours. Then, they were tested by the flow cytofluorometry to estimate DNA content in the cell nuclei. In case of apoptosis-like cellular death, the portion of cell nuclei with normal content of DNA became reduced, while the portion of cell nuclei containing abnormally small DNA quantity became larger.

The analysis procedure was the following: after incubation completion, cells were centrifuged and transferred to a standard phosphate isotonic buffer pH 7.4, containing RNA-ase A (20 µg/mL), ethidium bromide (fluorometric indicator for double stranded nucleic acid, 10 µg/mL) and $MgCl_2$ (5 mM). After the cells were disintegrated by nonionic detergent Triton X-100 (final concentration 0.1%). The suspension of cell nuclei thus obtained was analyzed by flow cytofluorometry with an argon laser as a source of light (wave length 488 nm). The red fluorescence due to DNA bound ethidium bromide was taken to be the measure of DNA content in the cell nuclei. In addition, corresponding samples were studied microscopically for revealing concomitant changes in cell morphology.

The study results are presented in Tables 11, 12 and FIG. 1). The table 11 shows the presence of GSSG or its drug forms promoted proliferation of normal lymphocytes of healthy volunteers, which resulted in increase in their number, while flow cytofluorometry analysis did not reveal any changes characteristic for apoptosis-like cell death (FIGS. 1c–d).

Figure 1A:
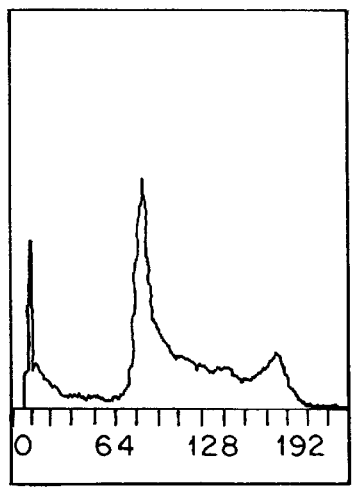
FIGS. 1a, 1b, 1c and 1d are charts showing cytofluorometric analysis of cells HL-60, cytofluorometric analysis of cells HL-60 in tee presence of the preparation of this invention, cytofluorometric analysis of human lymphocytes, and cytofluorometric analysis of lymphocytes in the presence of the preparation of this invention, respectively, as will be described in the discussion of Example 4, relating to research of apoptosis-induced preparation activity in cultivated mammalian cells.
Figure 1B:
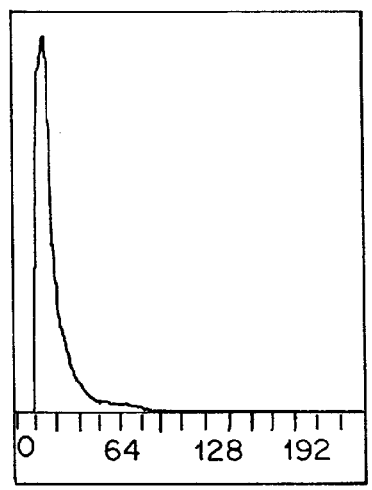
Figure 1C:
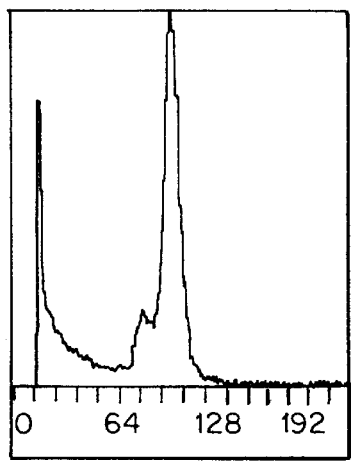
Figure 1D:
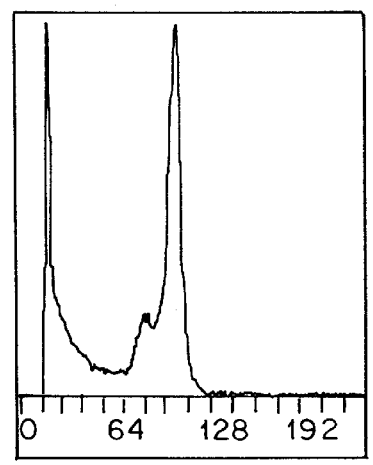

Observation carried out on cell cultures of the tumor cells of myeloid line HL-60 revealed ability of GSSG (as well as its drug forms) to slowdown the proliferation of transformed cells. Table 12 shows that GSSG compositions with hydrogen peroxide, inosine and cystamine inhibit cell HL-60 proliferation better than GSSG alone. The flow cytofluorometry analysis demonstrates the slowdown of cell growth of the HL-60 line cells was associated with characteristic morphological indications of apoptosis-like death: sphere-like cells became multi-fragmented with plural interceptions, the number of cell nuclei with normal content of DNA fell down, while there was an increase in portion of nuclei with abnormally low DNA content (FIGS. 1a–1b).

TABLE 11

Effect of the test articles on number of normal lymphocytes per well ($\times 10^4$ cells) throughout the 96-hr incubation. (M ± m)

| Test articles (solutions) | 24 hours | 48 hours | 72 hours | 96 hours |
| --- | --- | --- | --- | --- |
| GSSG in normal saline | 27 ± 2 | 98 ± 6* | 176 ± 12 | 386 ± 18* |
| GSSG + 0,003% $H_2O_2$ | 25 ± 4 | 108 ± 8* | 231 ± 14* | 419 ± 21* |
| GSSG + 0.1% inosine | 28 ± 3 | 107 ± 5* | 212 ± 16* | 306 ± 12* |
| GSSG + 0.1% cystamine | 26 ± 3 | 93 ± 5* | 186 ± 10* | 263 ± 14* |
| 0,003% $H_2O_2$ | 28 ± 2 | 73 ± 5 | 123 ± 8 | 206 ± 8 |
| 0.1% inosine | 26 ± 4 | 78 ± 7 | 141 ± 12 | 216 ± 16 |
| 0.1% cystamine | 30 ± 2 | 72 ± 4 | 122 ± 9 | 196 ± 11 |
| 10% fetal calf serum | 29 ± 4 | 74 ± 7 | 133 ± 18 | 263 ± 13 |

*Differences are statistically significant ($p < 0.05$) as compared to 10% fetal calf serum.

TABLE 12

Effect of the test articles on number of HL-60 cells per well ($\times 10^4$ cells) throughout the 96-hr incubation. (M ± m)

| Test articles (solutions) | 24 hours | 48 hours | 72 hours | 96 hours |
| --- | --- | --- | --- | --- |
| GSSG in normal saline | 102 ± 4 | 156 ± 6* | 386 ± 21* | 390 ± 11* |
| GSSG + 0,003% $H_2O_2$ | 96 ± 6* | 132 ± 4* | 286 ± 18* | 306 ± 18* |
| GSSG + 0.1% inosine | 49 ± 3* | 76 ± 6* | 138 ± 11* | 165 ± 9* |
| GSSG + 0.1% cystamine | 68 ± 8* | 102 ± 11* | 242 ± 19* | 256 ± 14* |
| 0,003% $H_2O_2$ | 122 ± 6 | 186 ± 12 | 488 ± 24 | 712 ± 22 |
| 0.1% inosine | 96 ± 8* | 152 ± 8* | 312 ± 21* | 527 ± 18* |
| 0.1% cystamine | 112 ± 10 | 182 ± 9 | 465 ± 11 | 618 ± 19 |
| 10% fetal calf serum | 119 ± 7 | 181 ± 13 | 471 ± 7 | 752 ± 16 |

*Differences are statistically significant ($p < 0.05$) as compared to 10% fetal calf serum.

Thus, the results obtained enable to declare the dual functional properties of GSSG and its drug forms which selectively induce proliferation slowdown and apoptosis-like death of tumor cells while accelerate proliferation of normal human cells (lymphocytes) without any signs of their apoptosis. The application of GSSG in combination with inosine produces the most prominent effect of GSSG in respect of normal cells.

EXAMPLE #5

Effect of GSSG and its Drug Forms on Progression of Experimental Tumors in Mice

An antitumor activity of GSSG, as well as its drug forms containing 0.003% hydrogen peroxide or 0.1% inosine, or 0.1% cystamine, was evaluated in the two mouse models of the tumor process induced by the intraperitoneal inoculation of leukemia P388 and leukemia L1210 cells. An influence of 7 day course of test article daily administration was studied in respect of variations of serum cytokine levels (IL-1, IL-2, IL-6, IFNα, TNF). In parallel, the tumor progression was estimated using the two integral indices: pace of mouse weight gain due to accumulation of ascitic fluid, and by animal mean survival time after inoculation.

The study was carried out on DBA/2 mice weighing 18–21 g. First, tumor cell passage was performed using 6 animals for each cell line. For this, cells kept at the temperature of the liquid nitrogen were de-frozen and adjusted to the concentration of 5×10⁶ cells/mL by sterile Hanks' solution. Then, 6 mice were intraperitoneally inoculated with 0.2 mL of each line cellular suspension.

Ascitic fluid was collected 6 days after the inoculation with L1210 cells and 8 days after the inoculation with P388 ones. Thus obtained, the samples of passaged tumor cells were used for the main experiments. The fluid liquid was dissolved by sterile Hanks' solution so that cell concentration be $5 \times 10^6$ cells/mL for P388 cells and $5 \times 10^5$ cells/mL for L1210 cells.

Nine groups of animals with no less than 15 mice each were formed for experiments with either tumor cell line. Mice were inoculated with 0.2 mL of resultant cell suspensions per mouse ($10^6$ P388 cells/mouse, and $10^5$ L1210 cells/mouse). 24 hours after the tumor cells inoculation, animals were given the first injections of the test articles or vehicles. The test article injections were made daily till the 14th day of the experiment or until the animal's death. The volume of solutions injected comprised 0.01 mL/g body weight. Description of nine groups of animals formed for experiments with either tumor cell line is given below.

Control groups:
1—intact animals receiving imitation of tumor cell inoculation (injection of normal saline) which further were treated with normal saline throughout the entire experiment;
2—control animals, inoculated with tumor cells, which further were treated with test article vehicle (normal saline);

Control groups:
3—experimental animals, inoculated with tumor cells, which further were treated with test article (GSSG dissolved in normal saline) in a dose of 5 mg/kg;
4—experimental animals, inoculated with tumor cells, which further were treated with a variant of test article drug form (GSSG dissolved in normal saline containing 0.003% of hydrogen peroxide), with a GSSG dose of 5 mg/kg;
5—experimental animals, inoculated with tumor cells, which further were treated with a variant of test article drug form (GSSG dissolved in normal saline containing 0.1% of inosine), with a GSSG dose of 5 mg/kg;
6—experimental animals, inoculated with tumor cells, which further were treated with a variant of test article drug form (GSSG dissolved in normal saline containing 0.1% cystamine), with a GSSG dose of 5 mg/kg;
7—experimental animals, inoculated with tumor cells, which further were treated with a variant of drug form component (normal saline containing 0.03% of hydrogen peroxide), without GSSG;
8—experimental animals, inoculated with tumor cells, which further were treated with a variant of drug form component (normal saline containing 0.1% of inosine), without GSSG;
9—experimental animals, inoculated with tumor cells, which further were treated with a variant of drug form component (normal saline containing 0.1% of cystamine), without GSSG;

Tables 13 and 14 contain results on test article efficacy evaluation as to variations of cytokine endogenous production, as well as data on integral parameters of the tumor process progression. The results obtained show that both GSSG and its drug forms have a substantial cytokine inducing effect, reliably retard (if compared to the control groups) the accumulation of ascitic fluid and increase the mean survival time. GSSG alone and GSSG together with 0.003% of hydrogen peroxide increase more remarkably the IL-1 and IFNα serum levels, whereas GSSG in combination with 0.1% inosine and 0.1% cystamine cause a larger increase in IL-2, IL-6, TNFα serum levels.

The most prominent antitumor effect in respect to slow-down of ascitic fluid accumulation and prolongation of the mean survival time for either tumor models (P388 and L1210 leukemia) were obtained with GSSG in combination with 0.1% cystamine.

TABLE 13

Effect of the test articles on the cytokine serum levels, the accumulation of ascitic fluid and the mean survival time of mice inoculated with leukemia L1210 cells (M ± m)

| Group of animals | The number of injections | Concentration of factors in serum, (pg/mL); | | | | | Accumulation of ascitic fluid (weight gain, %) | Mean survival time |
| | | IL-1 | IL-2 | Il-6 | IFNα | TNFα | | |
| 1 | 2 | 3 | 4 | 5 | 6 | 7 | 8 | 9 |
| Control animals | 0 | 22.0 ± 3.15 | 14.50 ± 2.56 | 93.20 ± 10.58 | 82.2 ± 9.05 | 79.70 ± 8.15 | 0.7 ± 0.1 | 9.02 ± 0.19 |
| | 3 | 28.5 ± 4.01 | 23.18 ± 3.11 | 108.0 ± 14.12 | 100.55 ± 11.34 | 80.3 ± 8.81 | 7.14 ± 0.9 | |
| | 7 | 13.4 ± 2.68 | 17.8 ± 2.51 | 136.70* ± 15.2 | 140.3 ± 16.25 | 196.90 ± 21.30 | 25.4 ± 2.62 | |
| Intact animals | 0 | 20.09 ± 1.95 | 13.14 ± 1.12 | 84.0 ± 9.65 | 108.0 ± 11.33 | 77.90 ± 6.85 | 0.2 ± 0.1 | 35 ± 0 |
| | 3 | 25.10 ± 2.31 | 21.75 ± 1.44 | 85.60 ± 9.01 | 101.0 ± 8.72 | 89.0 ± 7.13 | 1.12 ± 0.3 | |
| | 7 | 21.30 ± 2.98 | 21.15 ± 1.86 | 84.9 ± 7.16 | 90.0 ± 10.11 | 116. ± 10.83 | 4.6 ± 1.23 | |
| GSSG | 0 | 27.5 ± 3.60 | 14.7 ± 3.13 | 124.40 ± 13.7 | 144.80 ± 15.34 | 98.10 ± 11.54 | 0.77 ± 0.16 | 10.74 ± 0.51* |
| | 3 | 57.6 ± 7.14 | 57.7 ± 6.80 | 301.0 ± 32.2 | 508.0* ± 54.3 | 397.0* ± 44.50 | 4.02* ± 0.53 | |
| | 7 | 167.5 ± 18.30 | 144.5 ± 17.03 | 678. ± 74.5 | 1207.0* ± 116.3 | 610.0* ± 71.9 | 15.67* ± 1.70 | |
| GSSG + 0.003% H₂O₂ | 0 | 19.8 ± 2.05 | 14.84 ± 2.13 | 108.0 ± 9.17 | 119.40 ± 9.56 | 78.0 ± 6.15 | 0.44 ± 0.16 | 11.13 ± 0.49* |
| | 3 | 126.0 ± 13.9 | 99.0 ± 11.3 | 298. ± 24.5 | 238.0 ± 18.9 | 406.* ± 35.3 | 3.17* ± 0.41 | |
| | 7 | 123.5 ± 12.7 | 189.0 ± 21.4 | 445. ± 4.14 | 1413* ± 129. | 818* ± 73.5 | 14.04* ± 1.1 | |
| GSSG + 0.1% inosine | 0 | 25.5 ± 2.86 | 17.40 ± 1.92 | 104. ± 8.15 | 122.4 ± 10.43 | 121.9 ± 10.33 | 0.63 ± 0.16 | 12.01 ± 0.49* |
| | 3 | 83.10 ± 9.15 | 40.8 ± 5.0 | 512.* ± 48.7 | 628.* ± 56.4 | 565.* ± 50.03 | 1.75* ± 0.25 | |
| | 7 | 238.0 ± 29.56 | 91.1 ± 11.08 | 106. ± 9.14 | 1650.* ± 148 | 1904.* ± 186.0 | 5.69* ± 0.74 | |
| GSSC + 0.1% | 0 | 23.14 ± 2.86 | 17.0 ± 1.55 | 102. ± 8.04 | 129.0 ± 9.80 | 101.5 ± 8.16 | 0.76 ± 0.19 | 11.96 ± 0.59* |
| | 3 | 118.0 ± 13.42 | 59.16 ± 7.55 | 145. ± 11.8 | 761* ± 59.4 | 357.0* ± 28.30 | 2.47* ± 0.28 | |

TABLE 13-continued

Effect of the test articles on the cytokine serum levels, the accumulation of ascitic fluid and the mean survival time of mice inoculated with leukemia L1210 cells (M ± m)

| Group of animals 1 | The number of injections 2 | IL-1 3 | IL-2 4 | Il-6 5 | IFNα 6 | TNFα 7 | Accumulation of ascitic fluid (weight gain, %) 8 | Mean survival time 9 |
|---|---|---|---|---|---|---|---|---|
| cystamine | 7 | 189.20 ± 21.0 | 249. ± 22.7 | 400.0* ± 32.5 | 1700.* ± 163. | 709.0* ± 59.0 | 6.85* ± 0.91 | |
| 0.003% | 0 | 17.07 ± 1.65 | 16.18 ± 1.68 | 120.9 ± 10.7 | 133.7 ± 10.45 | 110. ± 9.13 | 0.79 ± 0.17 | 9.7 ± |
| H₂O₂ | 3 | 38.15 ± 4.11 | 23.5 ± 3.3 | 140. ± 13.3 | 189. ± 15.45 | 158.0 ± 11.97 | 6.12 ± 0.73 | 0.21 |
| | 7 | 23.6 ± 3.05 | 45.5 ± 5.8 | 103. ± 9.18 | 209. ± 18.30 | 220.0* ± 24.5 | 21.61 ± 2.55 | |
| 0.1% | 0 | 41.0 ± 4.23 | 17.80 ± 1.49 | 108. ± 9.03 | 117.3 ± 10.81 | 104.3 ± 9.17 | 0.61 ± 0.14 | 9.61 ± |
| inosine | 3 | 55.6 ± 6.17 | 22.3 ± 2.14 | 91.0 ± 8.8 | 160.0 ± 12.47 | 130.0 ± 10.85 | 7.02 ± 0.64 | 0.18 |
| | 7 | 36.40 ± 4.81 | 14.6 ± 1.53 | 119. ± 10.5 | 205. ± 21.3 | 157.0 ± 15.80 | 26.30 ± 2.57 | |
| 0.1% | 0 | 36.0 ± 3.12 | 16.9 ± 1.5 | 63.0 ± 5.0 | 115.0 ± 10.52 | 88.6 ± 5.19 | 0.47 ± 0.18 | 9.53 ± |
| cystamine | 3 | 47.50 ± 5.17 | 17.30 ± 1.46 | 70.0 ± 12.6 | 200. ± 18.0 | 185.0 ± 16.70 | 5.93 ± 0.47 | 0.18 |
| | 7 | 28.0 ± 3.0 | 22.8 ± 1.90 | 155.0 ± 13.4 | 137.0 ± 14.5 | 213.0 ± 18.54 | 21.17 ± 2.05 | |

Differences are statistically significant (p < 0.05) as compared as compared to the control group

TABLE 14

Effect of the test articles on the cytokine serum levels, the accumulation of ascitic fluid and the mean survival time of mice inoculated with leukemia P388 cells (M ± m)

| Group of animals 1 | The number of injections 2 | IL-1 3 | IL-2 4 | IL-6 5 | IFNα 6 | TNFα 7 |
|---|---|---|---|---|---|---|
| Control animals | 0 | 19.6 ± 3.85 | 10.5 ± 1.59 | 86.18 ± 7.13 | 90.5 ± 7.76 | 85.0 ± 6.15 |
| | 3 | 34.7 ± 5.42 | 26.7 ± 3.18 | 133.0 ± 15.2 | 113.0 ± 12.0 | 96.17 ± 8.2 |
| | 7 | 10.8 ± 2.34 | 20.3 ± 3.08 | 156.10* ± 20,0 | 158 ± 10.8 | 218* ± 22.03 |
| Intact animals | 0 | 25.12 ± 1.76 | 17.70 ± 1.84 | 104.50 ± 9.94 | 90.50 ± 7.19 | 88.64 ± 7.14 |
| | 3 | 33.0 ± 3.57 | 26.8 ± 3.07 | 92.80 ± 8.03 | 116.0 ± 10.55 | 89.0 ± 7.23 |
| | 7 | 30.83 ± 2.15 | 25.40 ± 2.17 | 102.0 ± 8.89 | 112.31 ± 10.86 | 93.7 ± 7.64 |
| GSSG | 0 | 23.5 ± 4.22 | 12.8 ± 1.95 | 102.0 ± 12.8 | 134. ± 9.8 | 90.03 ± 8.07 |
| | 3 | 62.3 ± 9.15 | 64.6 ± 7.13 | 280.0* ± 31.2 | 460. ± 40.8 | 306. ± 24.4 |
| | 7 | 147.0 ± 17.30 | 128.10 ± 16.55 | 624.0* ± 45.6 | 1024. ± 97.0 | 560. ± 48.8 |
| GSSG + 0,003% H₂O₂ | 0 | 17.4 ± 2.4 | 9.41 ± 2.02 | 90.8 ± 10.10 | 101.0 ± 9.88 | 73.5 ± 5.17 |
| | 3 | 109.6 ± 14.4 | 104.8 ± 15.30 | 314.0 ± 37.2 | 255.0 ± 22.3 | 355.* ± 36.2 |
| | 7 | 142.6 ± 16.3 | 174.0 ± 20.9 | 501.0* ± 48.3 | 1505 ± 131.0 | 890.* ± 78.3 |
| GSSG + 0.1% inosine | 0 | 28.7 ± 3.05 | 7.13 ± 0.98 | 129.8 ± 14.0 | 123.4 ± 10.01 | 109.0 ± 11.2 |
| | 3 | 75.0 ± 8.13 | 36.4 ± 4.8 | 618.0* ± 52.3 | 693.0* ± 61.8 | 517* ± 44.5 |
| | 7 | 210.4 ± 26.8 | 84.0 ± 10.03 | 520.0* ± 51.0 | 1810.* ± 129. | 2120.* ± 193. |
| GSSC + 0.1% cystamine | 0 | 20.8 ± 2.91 | 16.7 ± 1.88 | 118.9 ± 12.3 | 114.6 ± 9.87 | 95.6 ± 9.1 |
| | 3 | 109.2 ± 10.45 | 37.03 ± 4.15 | 156.6 ± 11.8 | 708.0* ± 61.9 | 326* ± 28.7 |
| | 7 | 168.0 ± 21.15 | 211.0 ± 25.6 | 414.0* ± 18.4 | 1950* ± 180.0 | 785.* ± 69.0 |
| 0,003% H₂O₂ | 0 | 15.5 ± 2.04 | 14.95 ± 2.16 | 134.0 ± 15.6 | 129. ± 10.0 | 119. ± 9.13 |
| | 3 | 44.7 ± 6.14 | 22.0 ± 2.81 | 156.0 ± 16.3 | 205.8 ± 18.3 | 144.5 ± 12.8 |
| | 7 | 28.6 ± 4.11 | 40.8 ± 5.12 | 110.9 ± 12.5 | 190. ± 16.7 | 248. ± 20.7 |
| 0.1% inosine | 0 | 36.7 ± 5.12 | 16.50 ± 1.09 | 115.0 ± 12.5 | 81.4 ± 6.13 | 122.0 ± 10.0 |
| | 3 | 48.2 ± 7.13 | 20.19 ± 1.54 | 90.0 ± 7.11 | 105. ± 11.3 | 96.5 ± 8.7 |
| | 7 | 31.0 ± 5.12 | 13.40 ± 1.68 | 129.0 ± 10.4 | 184. ± 16.1 | 144.8 ± 12.9 |
| 0.1% cystamine | 0 | 30.0 ± 4.02 | 14.9 ± 2.05 | 72.7 ± 9.10 | 107 ± 8.06 | 80.5 ± 7.14 |
| | 3 | 41.5 ± 5.81 | 15.25 ± 1.80 | 184.0 ± 15.6 | 216. ± 19.08 | 204. ± 16.1 |
| | 7 | 22.3 ± 3.0 | 20.18 ± 2.50 | 170.6 ± 14.3 | 315. ± 9.80 | 220. ± 19.1 |

| Group of animals 1 | The number of injections 2 | Accumulation of ascitic fluid (weight gain, %) 8 | Mean survival time 9 |
|---|---|---|---|
| Control animals | 0 | 0.5 ± 0.07 | 9,6 ± 0,22 |
| | 3 | 6.9* ± 0.52 | |
| | 7 | 28.2* ± 2.9 | |
| Intact animals | 0 | 0,3 ± 0,2 | 35* ± 0 |
| | 3 | 1.62 ± 0.4 | |
| | 7 | 5.1 ± 1.08 | |
| GSSG | 0 | 0.48 ± 0.032 | 11.0 ± 0.44* |
| | 3 | 3.7* ± 0.32 | |
| | 7 | 15.2* ± 0.16 | |
| GSSG + 0,003% H₂O₂ | 0 | 0.39 ± 0.11 | 11.6 ± 0.53* |
| | 3 | 2.93* ± 0.33 | |

TABLE 14-continued

Effect of the test articles on the cytokine serum levels, the accumulation of ascitic fluid and the mean survival time of mice inoculated with leukemia P388 cells (M ± m)

|  |  |  |  |
|---|---|---:|---:|
|  |  | 7 | 13.6* ± 0.64 |
| GSSG + 0.1% inosine | 0 | 0.56 ± 0.16 | 12.7 ± 0.51* |
|  | 3 | 1.64* ± 0.19 |  |
|  | 7 | 5.15* ± 0.59 |  |
| GSSC + 0.1% cystamine | 0 | 0.61 ± 0.15 | 12.5 ± 0.56* |
|  | 3 | 2.26* ± 0.17 |  |
|  | 7 | 6.08* ± 0.77 |  |
| 0,003% $H_2O_2$ | 0 | 0.63 ± 0.15 | 9.9 ± 0.24 |
|  | 3 | 5.4 ± 0.62 |  |
|  | 7 | 20.3 ± 2.28 |  |
| 0.1% inosine | 0 | 0.58 ± 0.13 | 9,8 ± 0.21 |
|  | 3 | 6.8 ± 0.8 |  |
|  | 7 | 25.0 ± 2.22 |  |
| 0.1% cystamine | 0 | 0.67 ± 0.22 | 9.93 ± 0.27 |
|  | 3 | 6.0 ± 0.49 |  |
|  | 7 | 19.9 ± 1.67 |  |

Differences are statistically significant ($p < 0.05$) as compared as compared to the control group Therefore, animal treatment according to present invention led to: significant increasing in endogenous production of IL-2, IL-6, IFNα and TNFα; and a reliable inhibition of progression of experimental tumors and prolongation of the mean survival time.

New properties of a previously known substance—oxidized glutathione (GSSG), and its pharmacologically active compositions, containing 0.003% hydrogen peroxide, or 0.1% of inosine, or 0.1% cystamine, found in the preclinical studies, are thought to be sufficient to declare that GSSG and its pharmacological formulations possess an obvious biological and pharmacological activity, as well as a therapeutic effect. This justifies the application of the corresponding drug forms of GSSG along and GSSG in combination with pharmaceutically acceptable components capable of extending the oxidized glutathione half life, for preventing and treating the diseases in which stimulation of endogenous production of cytokines and hemopoietic factors is advantageous and considered beneficial by those who are skilled in the art.

The following examples (##6–12) of the GSSG drug forms clinical use support the idea of utilizing GSSG as an inducer of the endogenous cytokine and hemopoietic factor production in man, and provide for the method for disease treatment based on the above GSSG properties.

EXAMPLE #6

Effect of GSSG Drug Form on the Endogenous and Erythropoietin Production in Patients Having Neoplastic Disease Data presented in this example demonstrate the GSSG stimulatory effect on the endogenous cytokine and hemopoietic factor production in cancer patients. GSSG solution (5 mg/mL) was administered intravenously, slowly, every other day a 5 mg per injection. The cytokine endogenous production was determined by their blood levels prior to the first administration (with blood collected 24 hours before dosing) and after the third and the seventh injections. The cytokine levels were assessed by immunoenzyme technique using commercially available kits (Medgenix, Belgium), and expressed as pg/mL of culture medium.

As seen from the data given in Table 15, a pronounced stimulation of the endogenous cytokine (IL-1β, IL-6, TNF-α, IFN-α) and erythropoietin was noted as soon as after three first injections of GSSG. After the seventh administration (14 days of treatment) a manifold increase in the cytokines and erythropoietin blood levels was observed in the majority of cases.

TABLE 15

Effect of GSSG administered intravenously on cytokine and erythropoietin serum levels in cancer patients

| Patients | Number of injections | Serum level, pg/mL | | | | |
|---|---|---|---|---|---|---|
|  |  | IL-1β | IL-6 | TNFα | INFα | erythropoietin |
| Pulmonary | 0 | 18.3 | 138.0 | 57.2 | 83.3 | 143.0 |
| adenocarcinoma with | 3 | 96.7 | 156.0 | 280.0 | 395.6 | 605.0 |
| pleural metastases | 7 | 104.6 | 150.0 | 315.0 | 378.0 | 548.0 |
| Stomach adenocarcinoma | 0 | 12.0 | 93.5 | 27.0 | 4.6 | 21.6 |
| with liver metastases | 3 | 28.1 | 228.0 | 215.0 | 33.6 | 53.5 |
|  | 7 | 31.7 | 204.0 | 147.0 | 34.0 | 47.1 |
| Suprarenal corticocytoma | 0 | 8.4 | 61.9 | 39.8 | 41.3 | 8.3 |
| with liver, pulmonary and | 3 | 12.9 | 105.0 | 113.0 | 56.0 | 32.4 |
| peritoneal metastases | 7 | 17.3 | 167.0 | 103.9 | 61.5 | 28.6 |

EXAMPLE #7

Stimulation of the Endogenous and Erythropoietin Production in a Patient Suffering from Colorectal Cancer Complicated with Chemotherapy-Induced Hemodepression A 44-year old female patient was operated on for colorectal mass grown through the ovary and metastases in the mesenteric and omental lymph nodes ($T_4N_3M_1$). Postoperatively, 5-fluorouracil chemotherapy was conducted (total course dose 5.5 g) with resultant severe hemotoxicity.

One month after the chemotherapy the patient was reexamined, and ultrasonography of the peritoneum and computed tomography of the liver revealed an oval-shaped 13×10 mm solitary metastasis in the left liver lobe. Repeat blood counts showed incomplete recovery of the blood indices (leukopenia, lymphopenia, anemia, and thrombocytopenia of various severity were noted) rendering further chemotherapy impossible.

Laboratory parameters prior to the use of the oxidized glutathione drug form (5 mg of GSSG in 1 mL of 0.003% hydrogen peroxide) are listed in Table 6. The treatment according to the subject method was commenced with GSSG given intravenously for seven days, 5 mg once daily. After a 3-day interval, the treatment was resumed with 15 mg daily dose, IV, 10 days. This course was followed by a 7-day recess after which the therapy was continued with GSSG being given every other day IM, 15 mg daily (a total of 20 injections).

50 days following commencement of the treatment the patient was reevaluated, and ultrasonography of the peritoneum and computed tomography of the liver showed a considerable shrinkage (more than 50% of the pretreatment size) of the solitary hepatic metastasis. The post-treatment immunological indices are given in Table 6.

As seen from the data, both red and white blood cell counts have significantly improved, platelets almost completely recovered, ESR reduced, CD4+, CD8+, NK cell numbers increased. A considerable stimulation of the endogenous cytokine and erythropoietin production, with TNF (together with increased natural killers) being probably responsible for the regression of the hepatic metastasis. These changes were accompanied by an improved general condition of the patient.

This clinical case indicates apparent therapeutic efficacy of the subject method. The administered therapy resulted in significant stimulation of the endogenous cytokine and hemopoietic factor production, reduction in hepatic metastasis size, normalization of immunity parameters, and overall improvement in the patient's wellness.

TABLE 16

Effect of GSSG on blood indices, cytokine and erythropoietin serum levels, and immunological parameters in patient with colorectal cancer and chemotherapy induced hemodepression

| Parameter | Prior to the treatment | After the treatment completion |
|---|---|---|
| Erythrocytes | $2.9 \times 10^{12}$/L | $4.1 \times 10^{12}$/L |
| Hemoglobin | 79 g/L | 108 g/L |
| Leukocytes | $3.6 \times 10^9$/L | $5.4 \times 10^9$/L |
| Lymphocytes | $0.67 \times 10^9$/L | $1.57 \times 10^9$/L |
| Platelets | $92 \times 10^9$/L | $208 \times 10^9$/L |
| ESR | 44 mm/hr | 19 mm/hr |
| CD4+ | $204 \times 10^6$/L | $609 \times 10^6$/L |

TABLE 16-continued

Effect of GSSG on blood indices, cytokine and erythropoietin serum levels, and immunological parameters in patient with colorectal cancer and chemotherapy induced hemodepression

| Parameter | Prior to the treatment | After the treatment completion |
|---|---|---|
| CD8+ | $255 \times 10^6$/L | $661 \times 10^6$/L |
| NK-cells | $39 \times 10^6$/L | $109 \times 10^6$/L |
| IL-1β | 203 pg/mL | 815 pg/mL |
| IL-6 | 318 pg/mL | 1014 pg/mL |
| TNFα- | 117 pg/mL | 937 pg/mL |
| IFNγ | 84 pg/mL | 506 pg/mL |
| Erythropoietin | 162 pg/mL | 618 pg/mL |

EXAMPLE #8

Stimulation of the Endogenous Cytokine Production in an AIDS Patient with Cryptococcal Meningitis A 28-year old male was admitted with a previously confirmed diagnosis of AIDS, stage 3/4C (WHO staging system) in moderately grave condition. The patient presented with paroxysmal headache, dizziness, and vomiting. Weight 47 kg, Karnofsky score 60, torpid, fevers up to 39° C., dyspnea at rest.

Neurological examination revealed nuchal rigidity and diminished knee, ankle, biceps and triceps reflexes. Cerebrospinal fluid culture was positive for *Cryptococcus neoformans* which served the basis for making the diagnosis of cryptococcus meningoencephalitis, and the AIDS stage was refined as 4C.

A vigorous infusion therapy was started. In addition to palliative therapy the patient received a course of Fungizone (Amphotericin B) with no positive outcome. The neurologic symptomatology and the patient's general state continued to deteriorate. A low to moderate grade fever (37.5–38.5° C.) persisted.

By the time oxidized glutathione was started (5 mg/mL), the patient had a significant drop in CD4+ and CD8+ peripheral blood counts as well as anemia and overall lymphopenia (see Table 17).

The patient received the treatment to the subject method for 3 months (1 mL of the GSSG solution per administration). During the first month of treatment the patient was dosed every other day (first 10 days intravenously, the rest of the month—intramuscularly); during the second month the patient received the drug every three days (first 10 days IV, the rest of the month—subcutaneously).

By the middle of the first month therapy, the patient's condition improved significantly with the neurologic sign alleviated and low-grade fever not exceeding 37.5° C. In the course of treatment, the patient's cerebrospinal fluid was mycologically examined twice (cytology, cultures, latex-agglutination test for cryptococcal antigen). Towards the end of the first month therapy the number of viable *Cryptococcal neoformans* organisms was found to be considerably reduced. By the end of the second month the cytological, culture, and immunologic tests showed cerebrospinal fluid to be free of the pathogen. Because of the drastic improvement in the patient's state, during the third month the drug was given once weekly IM.

The hematology/immunology findings upon the therapy completion are given in Table 7. As evident from the table, the anemia signs have reduced and a significant increase in the number of lymphocytes and their subsets has taken place. These findings constitute AIDS restaging from 4C to 4B.

Noteworthy is the sizable elevation of the cytokine blood levels, with IL-2, IL-6, and IFN-γ playing the key role in the host defense against pathogenic fungi.

At discharge, the patient's condition was found satisfactory with body weight being 60 kg (weight gain made up 21.7% of the admission), normal body temperature, Karnofsky score of 90, and no neurological signs.

TABLE 17

Effect of GSSG on blood indices, cytokine and erythropoietin serum levels, and immunological parameters in patient with AIDS and cryptococcal meningitis

| Parameter | Pre-treatment | Post-treatment |
|---|---|---|
| Erythrocytes | $3.1 \times 10^{12}/L$; | $3.9 \times 10^{12}/L$; |
| Hemoglobin | 84 g/L; | 126 g/L; |
| Leukocytes | $6.3 \times 10^9/L$; | $5.1 \times 10^9/L$; |
| Lymphocytes | $0.8 \times 10^9/L$; | $1.45 \times 10^9/L$; |
| CD4+ | $55 \times 10^6/L$; | $338.3 \times 10^6/L$; |
| CD8+ | $135 \times 10^6/L$; | $883 \times 10^6/L$: |
| IL-1β | 18.9 pg/mL; | 123.4 pg/mL; |
| IL-2 | 0.32 IU/mL | 3.7 IU/mL |
| IL-6 | 16.0 pg/mL; | 272.0 pg/mL; |
| IL-10 | 45.0 pg/mL; | 608.0 pg/mL; |
| IFNα | 27.0 pg/mL. | 314.0 pg/mL. |
| IFNγ | 15.7 pg/mL | 349.8 pg/mL |

EXAMPLE #9

Stimulation of the Endogenous Cytokine Production and Therapeutic Effect in Patients with AIDS Complicated by Isosporiasis A 38-year old male had been observed for 2 years with the diagnosis of AIDS, stage 3C (WHO Staging System). During the preceding year, recurrent episodes of oral and esophageal candidiasis had been recorded as well as chronic intestinal isosporiasis manifested by poor appetite, nausea, frequent vomiting and watery stools containing blood and mucus. Repeatedly used clotrimoxazole (trimethoprim plus sulfamethoxazole, TMP-SMX) had produced unsteady remissions with rapid recurrence of the symptomatology. During the last month prior to admission another relapse of isosporiasis had occurred. The treatment with clotrimoxazole, immodium (loperamide) had brought no relief. The patient's condition had been gradually deteriorating: refractory fever 38° C. and above, 6–7 loose bloody and mucous stools a day, vomiting, advancing weight loss (15% of the premorbid weight in one year). The patient had been admitted with progressive worsening of his condition.

On admission, the patient presented with moderately grave condition, Karnofsky score of 50, fever 38.2° C., emaciation body weight 42 kg), virtually total lack of subcutaneous fat, pallor of skin, the signs of oral and esophageal candidiasis. Stool examination revealed a large number of *Isospora belli* oocysts.

By the time the therapy according to the subject method was started, the patient had lymphopenia, marked decline in CD4+ and CD8+ lymphocytes, hypoproteinemia (see Table 18).

The patient received the oxidized glutathione drug form (5 mg of GSSG in 1 mL 0.003% hydrogen peroxide) for 2 months (1 mL of the GSSG solution per administration). During the first month of treatment the patient was dosed every other day (first 10 days intravenously, the rest of the month—intramuscularly); during the second month the patient received the drug every three days (first 10 days IV, the rest of the month—subcutaneously).

The patient's condition began to noticeably improve after the first two weeks of treatment. By the end of the first month therapy the patient moved bowels no more than 1 or 2 times a day with stools being blood-free; body temperature only occasionally exceeded 37° C. At the end of the second month stool reexamination showed feces to be negative for *Isospora belli*. Because of the drastic improvement in the patient's state, during the third month the drug was given prophylactically once weekly IM. No relapses of the disease were noted.

The findings of hematology/blood chemistry evaluations upon the therapy completion are given in Table 18. As seen from the table, hypoproteinemia has reduced, the number of lymphocytes and their subsets considerably increased with the resultant restaging of AIDS to 3B stage according to the WHO Staging System.

Noteworthy is the marked increase of the cytokine blood levels, with IL-2 and IFN-γ known to play an important part in the host defense against protozoan infections.

As a result of the therapy administered the patient's condition improved drastically, fatigue alleviated, appetite regained. The weight gain comprised 30% of the admission value, Karnofsky score—90. On physical examination the patient's condition was rated as satisfactory. During 1.5 month follow-up no diarrhea relapses were reported.

TABLE 18

Effect of GSSG on blood indices, cytokine and erythropoietin serum levels, and immunological parameters in patient with AIDS and isosporiasis

| Parameter | Pre-treatment | Post-treatment |
|---|---|---|
| Erythrocytes | $4.04 \times 10^{12}/L$ | $4.75 \times 10^{12}/L$ |
| Hemoglobin | 108 g/L | 129 g/L |
| Leukocytes | $5.4 \times 10^9/L$ | $6.0 \times 10^9/L$ |
| Lymphocytes | $0.9 \times 10^9/L$ | $1.8 \times 10^9/L$ |
| CD4+ | $125 \times 10^6/L$ | $436.5 \times 10^6/L$ |
| CD8+ | $270 \times 10^6/L$ | $949.3 \times 10^6/L$ |
| Total protein | 46 g/L | 78 g/L |
| IL-1β | 27.8 pg/mL | 202.4 pg/mL |
| IL-2 | 0.51 IU/ml | 12.9 IU/ml |
| IL-6 | 13.5 pg/mL | 348.0 pg/mL |
| IL-10 | 62.0 pg/mL | 956.0 pg/mL |
| IFNα | 148.3 pg/mL | 860.0 pg/mL |
| IFNγ | 61.2 pg/mL | 698.8 pg/mL |

EXAMPLE #10

Stimulation of the Endogenous Erythropoietin Production and Therapeutic Effect in Patient with Hypoplastic Anemia and Pancytopenia A 37-year old male had been observed for about a year with anemia of unknown origin the severity of which had been gradually building up. For 10 months he had been troubled with fatigability, dizziness, frequent nasal bleedings, unusual susceptibility to respiratory infections, three episodes of pneumonia with one of them being croupous pneumonia. During the year the patient had lost 10% of his usual weight. Repeated outpatient treatment with oral and intravenous iron preparation, folic acid, B vitamins, including $B_{12}$, had produced no effect. One admission the patient presented with moderately grave condition, dyspnea on moderate exertion, bruises, and isolated petechial spots. Successive hematology analyses have revealed moderately severe to severe fairly hypochromic (color index 0.7–0.9) normocytic anemia (1.5–2.5×10$_{12}$/L), anisocytosis and poikilocytosis, moderate leukopenia, and thrombocytopenia within 50–80×10$^9$/L.

An aggressive infusion therapy with iron preparations, folic acid, cyanocobalamin, vitamins, prednisone, and repeated exythrocyte transfusions resulted in only marginal relief.

Bone marrow differential (punch biopsy) revealed marked hypocellularity with medullary cavities populated predominantly with fat cells. Both myeloid and erythroid lineages are significantly suppressed with the erythroidlmyeloid ration noticeably diminished. Megakaryocytes are scant in number with relative increase in nondifferentiated cells, plasma cells, and blasts. Iron stores are enriched. Diagnosis: hypoplastic anemia of unknown origin, pancytopenia.

Complete blood count and erythropoietin levels by the time the oxidized glutathione drug form (5 mg GSSG in 1 mL of 0.003% hydrogen peroxide) was started are given in Table 9. As is evident from the table, the laboratory findings are consistent with those characteristic of hypoplastic anemia with no typical increase of erythropoietin blood level, however. Moreover, the erythropoietin level was found to be considerably below the lower normal limit (9.2 pg/mL with the reference range 30–170 pg/mL corresponding to 3–17 mIU/mL).

The oxidized glutathione formulation therapy was started with intramuscular injections of 1 mg GSSG b.i.d. for three days. Further the dose was escalated up to 5 mg b.i.d. for 7 days. Blood counts have shown less severe anemia. From that point, the drug form was dosed at 10 mg IM once daily for 10 days and then, the RBC counts steadily recovering, the therapy was switched to IV administration of GSSG, once every three days for 30 days. Vitamins and iron preparations were given concomitantly per os.

The hematology findings and erythropoietin levels obtained 50 days following the subject treatment onset are listed in Table #9. As is easy to see from the data, both RBS and WBC counts significantly improved, as did the platelet counts, ESR reduced, erythropoietin levels exceeded the upper normal limit. Clinically, fatigue, dizziness, and dyspnea disappeared. On examination, no petechial spots or bruises could be found with no nasal bleedings observed or reported. The weight gain made up 5.5 kg (8% of the premorbid weight).

Bone marrow reexamination (punch biopsy upon therapy completion) found the myeloid tissue to occupy 60% of the medullary cavities with erythroid/myeloid ratio in the myeloid tissue isles exceeding the norm. There were normoblastoid hyperplasia signs with megaloblastoid cells found in normoblast congregations. Mast cells were encountered, megakaryocytes were present in abundance. Iron stores appeared to be somewhat enriched.

This clinical case indicates a clear therapeutic efficacy of the drug form. Due to the treatment administered the initially suppressed endogenous erythropoietin production received a potent boost. As a result, the hematology parameters virtually recovered and the anemia clinical signs resolved. The patient was discharged in satisfactory condition.

TABLE 19

Effect of GSSG on blood indices, erythropoietin serum level in patient with hypoplastic anemia and pancytopenia

| Parameter | Pre-treatment | Post-treatment |
| --- | --- | --- |
| Erythrocytes | 1.8 × 10$^{12}$/L | 4.3 × 10$^{12}$/L |
| Hemoglobin | 43 g/L | 119 g/L |
| Color index | 0.72 | 0.83 |
| Reticulocytes | 0.22% | 2.85% |
| Leukocytes | 4.2 × 10$^9$/L | 72 × 10$^9$/L |
| Lymphocytes | 1.6 × 10$^9$/L | 3.1 × 10$^9$/L |
| Platelets | 72 × 10$^9$/L | 219 × 10$^9$/L |
| ESR | 46 mm/hr | 15 mm/hr |
| Erythropoietin | 9.2 pg/mL | 201.7 pg/mL |

EXAMPLE #11

Stimulation of Endogenous Cytokine Production and the Therapeutic Effect in a Patient with a Stomach Cancer, Peritoneal Metastases, Ascites, Plenomegaly and Cholestatic Hepatitis A 33-year old patient was diagnosed as having stomach neoplasm for more than 2 years (adenocarcinoma of moderate differentiation degree). In 1993, the patient was operated on for a malignant stomach ulcer; and numerous dense lymph nodes were found in the porte hepatis which were considered to be metastases.

In January 1994 the course of chemotherapy (5FU) was complicated by the severe cholestasis and percutaneous drainage of the left and right liver ducts was undertaken, that 6 month's later was followed by the choledochoejunostomy with changeable transliver drains with Brown's anastomosis.

In November 1995 the state of the patient worsened. According to the examinations the patient experienced an active secondary hepatitis. The liver was enlarged and painful and protruded from the costal arch up to 5–6 sm. Blood chemistry indices proved to be persistently abnormal: bilirubin—40.0 due to indirect (up to 31.0); activity of amino transferases—approximately 6 times higher than upper normal limit, hypoalbunemia was up to 26%; and there was also hypergammaglobulinemia; hypercholesterolemia was up to 10.2 $\mu$mol/l.

During fibrogastrocopy (November, 1995), a tumor of the stomach located in the middle area of the stomach body and extending about 8 cm was confirmed. The tumor was solid-like. Stomach walls were rigid. Histology examination defined the tumor as adenocarcinoma of moderate degree laparotomy. Ascites were found with plural metastases all over the peritoneum, splenomegaly. The patient was identified as inoperable.

A decision was taken to apply (GSSG drug form containing 0.1% inosine. The drug was injected parenterally (intramuscular and intravenous), and additionally, the drug form was used via local injections around the tumor tissue with the help of endoscope. An average dose which was used for intramuscular and intravenous injections—0.1–0.5 mg/kg, and for local injections—up to 50 mg in situ. Parenteral injections of the drug were applied every other day, b.i.d. (intravenous injections at the morning, and intramuscular ones—at the evening), during three weeks, and after that—two times in a week, during four weeks. Two months after the beginning of the treatment with the drug form used fibrogastroduodenoscopy showed that esophagus was passable, mucous membrane was pink, cardia rosette was partly closed. On an empty stomach, a moderate amount of foamy secretion was in the stomach, which was intensively colored with bile. The tumor extent was 5 cm. At the same time, substantial improvement of hematology and blood chemistry indices were found.

Four month's later, the liver protruded 1 cm beyond the rib arch. On palpation the liver was not painful. Supersonic examination showed the appearance of fibrous tissue instead on the place of some areas previously affected with tumor tissue. Fibrogastroduodenoscopy performed in May, 1996, showed that th esophagus was partly closed. There was light turbid liquid in the stomach, which contained saliva. Mucous membrane was pink. The tumor was 3.6 cm in extent with the stomach walls being elastic. Duodenum was passable.

By comparison with results of examination conducted before treatment with the use of the GSSG drug form mentioned (November, 1995) the tumor was shrunk in its extent for 55%. Simultaneously there were significant beneficial changes in hepatic tests, hematology and immunology indices.

Thus, the treatment according to the present invention resulted in partial regress of neoplastic process with simultaneous obvious beneficial changes in hematology, blood chemistry and immunology parameters, and significant improvement of life quality.

EXAMPLE #12

Stimulation of Endogenous Cytokine Production and the Therapeutic Effect in a Patient with Skin Cancer (Merkel's Cell Carcinoma), Local Lymph Node Metastases and Chemotherapy-Hemo- and Induced Immunodepression A male patient, 64 years old, has been under medical supervision since August, 1995, when a hyperemic painless mass appeared in the scapular area, which had progressively grown in size. After a month's time, the mass spread over the axillary space, kept increasing, and became painful. A fever appeared (38.9° C.). Histological and immunological examination in October, 1995 made the diagnosis clear: neuroendocrinal form of skin cancer (Merkel's cell carcinoma) stage III.

In December, 1995 the patient was given a course of CMF chemotherapy (cyclophosphamide+methotrexate+fluorouracil) without appreciable curative effect. At the same time an obvious hemopoiesis depression (leukocytes 2.4× $10^9$/L) developed with simultaneous growth of cervical and superclavicular lymph nodes associated with local skin hyperemia.

In January-February 1996 chemotherapy scheme was changed: cysplatine+cyclophosphamide (CP instead of CMF). The chemotherapy brought about the following complications—cytopenia (leukocytes—1.4×$10^9$/l), cardiotoxicity in the form of ischeria deterioration. After the 2nd course of chemotherapy a substantial tumor progression was observed: necrosis in the left subaxillary area with fistula formation; edema of the left arm; infiltrating growth into soft tissues in the area of the left shoulder and the left subaxillary tissues; intoxication; persistent fever (38.8° C.). Because of inefficacy of chemotherapy and the obvious progression of the process, it was decided to administer a course of GSSG drug form in combination with 0.1% cystamine, together with chemotherapy (CMF).

After 10 daily injections of the GSSG drug form used (intravenously and intramuscularly, the dose 0.1–0.5 mg/kg per an injection), it was noticed: the following changes in the patient's status was revealed: improved quality of life (good appetite, mobility); ulceration drying out, abolition of suppurative discharge; fistula scarring, 30% tumor shrinkage; normal body temperature; limitation of hyperemic areas, the improvement of hematology indices.

The 3rd and 4th courses of chemotherapy (CMF) were carried out together with GSSG drug form (intravenous and intramuscular injections, b.i.d, intravenous dose 0.5 mg/kg; and intramuscular dose 0.2 mg/kg). Parenteral administration of the preparation was 3 times in a week, with local injections in the two spots around the tumor through the endoscope once a week (up to 25 mg for each spot). The following results were obtained: tumor process regression; good endurance of chemotherapy, the disappearance of pain syndrome, constant improvement of life quality, restoration of immunity and hemopoiesis, increasing level of cytokines and hemopoietic factors (see table 21).

In two months the treatment with the use of the present invention there was a stable level of endogenous production of cytokines and hemopoietic factors; the diminution of the left cervical and supraclavicular lymph nodes; the 70% shrinkage of tumor size in two dimensions; positive shifts in immunology indices; lack of chemotherapy hemodepression.

The clinical observation proves the clear curative effect of the treatment according to the present invention: together with the obvious stimulation of endogenous production of cytokines and hemopoietic factors there were a substantial decrease in tumor size, improvement of life quality, and beneficial changes in hematology, blood chemistry and immunology parameters.

TABLE 21

Effect of GSSG on blood and immunology indices and cytokine levels in patient with skin cancer (Merkel's cell carcinoma), local lymph node metastases and chemotherapy-induced hemo- and immunodepression.

| Parameter | Prior to the treatment | 3 months after the treatment beginning |
|---|---|---|
| Erythrocytes, $10^{12}$/L | 3.9 | 4.1 |
| Hemoglobin, g/L | 112 | 114 |
| Platelets, $10^9$/L | 210 | 262 |
| Leukocytes, $10^9$/L | 2.4 | 7.2 |
| Neutrophils (stab), % | 6 | 8 |
| Neutrophils (segm.), % | 79 | 60 |
| Lymphocytes, % | 8 | 24 |
| Monocytes, % | 4 | 7 |
| Eosinophils, % | 3 | 1 |
| ESR, mm/hr | 43 | 13 |
| Total protein, g/L | 61 | 78 |
| α1-globulin, % | 9.20 | 2.3 |
| α2-globulin, % | 12.32 | 8.2 |
| β-globulin, % | 13.08 | 14.0 |
| γ-globulin, % | 21.69 | 18.8 |
| A/G ratio | 0.78 | 0.94 |
| Urea, mmol/L | 8.54 | 4.3 |
| Creatinin, mmol/L | 0.123 | 0.095 |
| Bilirubin, mcmol/L | 4.6 | 4.1 |
| Prothrombin index, % | 82 | 100 |
| Glucose, mmol/L | 5.5 | 4.3 |
| SGOT, mmol/hr/L | 0.48 | 0.32 |
| SGPT, mmol/hr/L | 0.43 | 0.21 |
| Lymphocytes, $10^6$/L | 192 | 1728 |
| B-lymphocytes (CD20*) $10^6$/L | 60 | 234 |
| CD4*-lymphocytes, $10^6$/L | 84 | 604 |
| CD8*-lymphocytes, $10^6$/L | 13 | 329 |
| CD4*/CD8* | 6.5 | 1.8 |
| IL2-receptor bearing cells (CD25*), $10^6$/L | 64 | 881 |
| HLA11-receptor bearing cells, $10^6$/L | 36 | 498 |

TABLE 21-continued

Effect of GSSG on blood and immunology indices and cytokine levels in patient with skin cancer (Merkel's cell carcinoma), local lymph node metastases and chemotherapy-induced hemo- and immunodepression.

| Parameter | Prior to the treatment | 3 months after the treatment beginning |
|---|---|---|
| NK-cells (CD16+), $10^6$/L | 24 | 624 |
| IgA, g/L | 4.9 | 5.2 |
| IgM, g/L | 0.99 | 1.24 |
| IgG, g/L | 2.43 | 15.6 |
| Immune Complexes, OD units | 264 | 111 |
| IL-1β, pg./mL | 156 | 637 |
| IL-2, IU/mL | 1.12 | 36.5 |
| IL-6, pg./mL | 244 | 1029 |
| IFNα, pg./mL | 79 | 513 |
| IFNγ, pg./mL | 58 | 234 |
| TNF, pg./mL | 202 | 855 |

In Examples 13–15, the following designations for chemically modified GSSG derivatives will be used:

| | |
|---|---|
| S-thioethylamine-glutathione disulfide | S-thioethylamine-GSSG |
| bis-[DL-6,8,thiooctanil]•glutathione disulfide | bis-lipoil-GSSG |
| [b-alanyl-L-hystidil]•glutathione disulfide | carnosil-GSSG |
| [9-β-D-ribofuranosyladenil]•glutathione disulfide | adenosil-GSSG |
| bis-[L-2-amino-4-[methylthio]butanoil]•glutathione disulfide | bis-methionil-GSSG |

EXAMPLE 13

Effect of Lithium Salt of GSSG, S-thioethylamine-GSSG and Their Drug Forms on the Process of Apoptosis of Normal and Tumor Cells The ability of S-thioethylamine-GSSG and lithium salt of oxidized glutathione (GSSG), as well as their drug forms containing 0.003% hydrogen peroxide, or 0.1% inosine or 0.1% cystamine, or 7% dimethyl sulfoxide (DMSO) to influence processes cell death and apoptosis regulation was evaluated using normal or tumor cells (in all cases where lithium salts and sodium salts are used in the Examples of the application, 2 atoms are present attached to sites $X_1$ and $X_4$ of the GSSG). To this end, these substances had been incubated for 72 hours with cells of rat embrional fibroblasts (REF) and the same cells, transformed with adenoviral E1A gene in complementation with ras-oncogene (e-ras cell line). Subsequent evaluation of the cellularity of experimental samples was carried out by counting the quantity of cell per milliliter (for REF cell line) or clones in dish (for e-ras cell line).

Cells were cultivated on DMEM medium supplemented with 10% fetal calf serum and 50 mg/mL gentamicin. Cultivation was carried out in Petri dishes.

REF cells was cultivated with initial density of 800,000 cell per mL, evaluation of the cellularity was performed at 0, 24, 48 and 72 hours of incubation with the test articles.

E-ras cells were seeded at a cell density of 300 cells per 5 cm dish. 7 days after growth of e-ras cells had been started the quantity of clones was evaluated and the test articles were added into the dishes.

Evaluation of the test solution of lithium GSSG salt and S-thioethylamine-GSSG (5000 mg/mL), as well as lithium GSSG salt and S-thioethylamine-GSSG solutions containing 0.003% hydrogen peroxide, or, 0.1% inosine or 0.1% cystamine, or 7% DMSO, was carried out using 6 cellular samples for each test solution.

50 mcL of each test solution were added to one or the other cell culture and thereafter cells were cultivated for 24–72 hours. For the test-system for estimation of apoptosis regulation UV-induced cell death was triggered in a dose of 4 Dj. Test articles were added immediately after irradiation. Then, the quantity of cell per milliliter (for REF cell line) or clones in dish (for e-ras cell line) were monitored every 24 hours. For determination of DNA-fragmentation the electrophoresis in agarose gel was used at standard settings.

The study results are presented in Tables 22–25. The table 22 and 23 show that the presence of lithium salt of GSSG or S-thioethylamine-GSSG or their drug forms didn't promote apoptosis of normal cells (REF line). Observation carried out on cell cultures of the e-ras cells revealed ability of lithium salt of GSSG or S-thioethylamine-GSSG (as well as of their drug forms) to induce a transformed cell death.

TABLE 22

Effect of the test articles on number of REF cells (×$10^3$ cells) throughout the 72-hr incubation (M ± m).

| Tests article (solution) | 0 hours | 24 hours | 48 hours | 72 hours |
|---|---|---|---|---|
| Li-GSSG in normal saline | 860 ± 25 | 1496 ± 42 | 2606 ± 46 | 5180 ± 124 |
| Li-GSSG + 0.003% H2O2 | 830 ± 17 | 1326 ± 34 | 2695 ± 72 | 5360 ± 186 |
| Li-GSSG + 0.1% inosine | 826 ± 12 | 1340 ± 64 | 2641 ± 77 | 5063 ± 134 |
| Li-GSSG + 0.1% cystamine | 831 ± 24 | 1329 ± 41 | 2831 ± 53 | 5302 ± 221 |
| Li-GSSG + 7% DMSO | 800 ± 22 | 1463 ± 26 | 2820 ± 48 | 5206 ± 210 |
| S-thioethylamine-GSSG in normal saline | 789 ± 21 | 1422 ± 14 | 2602 ± 43 | 5112 ± 168 |
| | 782 ± 14 | 1426 ± 24 | 2645 ± 32 | 5160 ± 134 |
| S-thioethylamine-GSSG + 0.003% H2O2 | 824 ± 22 | 1398 ± 17 | 2684 ± 28 | 5210 ± 156 |
| | 841 ± 18 | 1386 ± 14 | 2478 ± 31 | 5089 ± 123 |
| S-thioethylamine-GSSG + 0.1% inosine | 821 ± 13 | 1462 ± 15 | 2671 ± 32 | 5121 ± 68 |
| S-thioethylamine-GSSG + 0.1% cystamine | 822 ± 11 | 1365 ± 14 | 2598 ± 63 | 5059 ± 34 |
| | 811 ± 10 | 1426 ± 24 | 2642 ± 25 | 5034 ± 128 |
| S-thioethylamine-GSSG + 7% DMSO | 822 ± 14 | 1523 ± 11 | 2486 ± 34 | 5048 ± 126 |
| | 801 ± 12 | 1420 ± 17 | 2651 ± 36 | 5298 ± 39 |
| 0.003% H2O2 | 824 ± 21 | 1486 ± 46 | 2645 ± 128 | 5125 ± 246 |
| 0.1% inosine | | | | |
| 0.1% cystamine | | | | |
| 7% DMSO | | | | |
| 10% fetal calf serum | | | | |

TABLE 23

Effect of the test articles on number of clones of e-ras cells throughout the 72-hr incubation (M ± m).

| Tests article (solution) | 0 hours | 24 hours | 48 hours | 72 hours |
|---|---|---|---|---|
| Li-GSSG in normal saline | 260 ± 25 | 196 ± 22 | 146 ± 16 | 108 ± 12 |
| Li-GSSG + 0.003% H2O2 | 250 ± 17 | 186 ± 14 | 125 ± 12 | 106 ± 16 |
| Li-GSSG + 0.1% inosine | 248 ± 11 | 201 ± 11 | 134 ± 12 | 98 ± 14 |
| Li-GSSG + 0.1% cystamine | 254 ± 15 | 182 ± 10 | 121 ± 14 | 102 ± 11 |

TABLE 23-continued

Effect of the test articles on number of clones of e-ras cells throughout the 72-hr incubation (M ± m).

| Tests article (solution) | 0 hours | 24 hours | 48 hours | 72 hours |
|---|---|---|---|---|
| Li-GSSG + 7% DMSO | 261 ± 12 | 184 ± 8 | 102 ± 16 | 76 ± 8 |
| S-thioethylamine-GSSG in normal saline | 286 ± 14 | 202 ± 14 | 156 ± 10 | 112 ± 12 |
| | 271 ± 16 | 208 ± 12 | 152 ± 11 | 121 ± 10 |
| S-thioethylamine-GSSG + 0.003% H2O2 | 292 ± 13 | 212 ± 14 | 151 ± 14 | 118 ± 14 |
| | 288 ± 11 | 210 ± 12 | 146 ± 8 | 124 ± 8 |
| S-thioethylamine-GSSG + 0.1% inosine | 278 ± 14 | 221 ± 8 | 132 ± 10 | 102 ± 8 |
| S-thioethylamine-GSSG + 0.1% cystamine | 288 ± 4 | 286 ± 4 | 264 ± 3 | 234 ± 6 |
| | 292 ± 11 | 290 ± 8 | 269 ± 8 | 243 ± 8 |
| S-thioethylamine-GSSG + 7% DMSO | 276 ± 4 | 281 ± 4 | 271 ± 6 | 258 ± 3 |
| | 268 ± 11 | 271 ± 2 | 268 ± 8 | 243 ± 6 |
| 0.003% H2O2 0.1% inosine 0.1% cystamine 7% DMSO 10% fetal calf serum | 272 ± 8 | 275 ± 3 | 258 ± 4 | 232 ± 4 |

The tables 24 and 25 show that the presence of lithium salt of GSSG or S-thioethylamine-GSSG or their drug forms do not promote the apoptosis of normal cells (REF line) induced by UV-irradiation. Observations carried out on e-ras cell cultures revealed ability of lithium salt of GSSG or S-thioethylamine- GSSG (as well as their drug forms) to potentiate death of the transformed cells.

TABLE 24

Effect of the test articles on number of REF cells (×10$^3$ cells) throughout the 72-hr incubation (M ± m) after UV-irradiation.

| Tests article (solution) | 0 hours | 24 hours | 48 hours | 72 hours |
|---|---|---|---|---|
| Li-GSSG in normal saline | 860 ± 25 | 496 ± 42 | 260 ± 46 | 190 ± 24 |
| Li-GSSG + 0.003% H2O2 | 830 ± 17 | 326 ± 34 | 269 ± 22 | 193 ± 18 |
| Li-GSSG + 0.1% inosine | 826 ± 12 | 340 ± 64 | 241 ± 17 | 163 ± 13 |
| Li-GSSG + 0.1% cystamine | 831 ± 24 | 329 ± 41 | 281 ± 33 | 192 ± 21 |
| Li-GSSG + 7% DMSO | 800 ± 22 | 463 ± 26 | 282 ± 18 | 186 ± 10 |
| S-thioethylamine-GSSG in normal saline | 789 ± 21 | 422 ± 14 | 260 ± 23 | 212 ± 16 |
| | 782 ± 14 | 426 ± 24 | 245 ± 22 | 2160 ± 34 |
| S-thioethylamine-GSSG + 0.003% H2O2 | 824 ± 22 | 398 ± 17 | 264 ± 22 | 210 ± 16 |
| | 841 ± 18 | 386 ± 14 | 248 ± 11 | 189 ± 23 |
| S-thioethylamine-GSSG + 0.1% inosine | 821 ± 13 | 462 ± 15 | 271 ± 22 | 212 ± 16 |
| S-thioethylamine-GSSG + 0.1% cystamine | 822 ± 11 | 365 ± 14 | 258 ± 33 | 159 ± 24 |
| | 811 ± 10 | 426 ± 24 | 262 ± 22 | 234 ± 28 |
| S-thioethylamine-GSSG + 7% | 822 ± 14 | 523 ± 11 | 246 ± 34 | 208 ± 26 |
| | 801 ± 12 | 420 ± 17 | 251 ± 36 | 208 ± 39 |
| DMSO 0.003% H2O2 0.1% inosine 0.1% cystamine 7% DMSO 10% fetal calf serum | 824 ± 21 | 486 ± 46 | 265 ± 28 | 195 ± 46 |

TABLE 25

Effect of the test articles on number of clones of e-ras cells throughout the 72-hr incubation (M ± m) after UV-irradiation.

| Tests article (solution) | 0 hours | 24 hours | 48 hours | 72 hours |
|---|---|---|---|---|
| Li-GSSG in normal saline | 261 ± 20 | 166 ± 12 | 116 ± 6 | 78 ± 4 |
| Li-GSSG + 0.003% H2O2 | 250 ± 12 | 146 ± 14 | 115 ± 5 | 76 ± 6 |
| Li-GSSG + 0.1% inosine | 248 ± 11 | 141 ± 11 | 124 ± 8 | 68 ± 4 |
| Li-GSSG + 0.1% cystamine | 254 ± 15 | 142 ± 10 | 101 ± 4 | 70 ± 11 |
| Li-GSSG + 7% DMSO | 261 ± 12 | 124 ± 8 | 86 ± 6 | 56 ± 8 |
| S-thioethylamine-GSSG in normal saline | 286 ± 14 | 182 ± 14 | 116 ± 8 | 82 ± 4 |
| | 271 ± 16 | 168 ± 12 | 102 ± 7 | 71 ± 10 |
| S-thioethylamine-GSSG + 0.003% H2O2 | 292 ± 13 | 162 ± 7 | 111 ± 4 | 76 ± 4 |
| | 288 ± 11 | 152 ± 8 | 116 ± 8 | 72 ± 8 |
| S-thioethylamine-GSSG + 0.1% inosine | 278 ± 14 | 134 ± 8 | 82 ± 10 | 50 ± 6 |
| S-thioethylamine-GSSG + 0.1% cystamine | 288 ± 4 | 186 ± 4 | 124 ± 3 | 84 ± 6 |
| | 292 ± 11 | 190 ± 8 | 129 ± 8 | 93 ± 8 |
| S-thioethylamine-GSSG + 7% | 276 ± 4 | 181 ± 4 | 111 ± 6 | 108 ± 3 |
| | 268 ± 11 | 171 ± 2 | 108 ± 8 | 103 ± 6 |
| DMSO 0.003% H2O2 0.1% inosine 0.1% cystamine 7% DMSO 10% fetal calf serum | 272 ± 8 | 175 ± 3 | 125 ± 4 | 93 ± 4 |

Thus, the results obtained enable to postulate the duality of functional properties of lithium salt of GSSG or S-thioethylamine-GSSG and their drug forms which selectively induce apoptosis-like death of tumor cells without any signs of apoptosis in normal cells. Besides, all the test articles were able to decrease the apoptosis processes of normal cells induced by UV-irradiation and, were able to potentiate these processes in transformed cells. The application of S-thioethylamine-GSSG in combination with DMSO produced a more prominent effect than that of lithium salt of GSSG in respect of transformed cells.

EXAMPLE 14

Effect of Lithium Salt of GSSG and S-thioethylamine-GSSG and Their Drug Forms on Progression of Experimental Tumors in Mice An antitumor activity of lithium salt of GSSG and S-thioethylamine-GSSG, as well as their drug forms containing 0.003% hydrogen peroxide, 0.1% inosine, 0.1% cystamine, or 7% dimethyl sulfoxide (DMSO) was evaluated in the three mouse models of the tumor process induced by the intraperitoneal inoculation of leukemia P388, leukemia L1210 cells and Erlich adenocarcinoma cells. An influence of 7 day course of test article daily administration was studied in respect of tumor progression, which was estimated using the two integral indices:

The study was carried out on DBA/2 mice weighing 18–21 g. First, tumor cell passage was performed using 6 animals for each cell line. For this, cells kept at the temperature of the liquid nitrogen were de-frozen and adjusted to the concentration of 5×10$^6$ cells/mL by sterile Hanks' solution. Then, 6 mice were intra peritoneally inoculated with 0.2 mL of each line cellular suspension.

Ascitic fluid was collected 6 days after the inoculation with L1210 cells, 8 days after the inoculation with P388 ones and 18 days after inoculation with Erlich adenocarcinoma cells. Thus obtained, the samples of passaged tumor cells were used for the main experiments. The fluid liquid was dissolved by sterile Hanks' solution so that cell concentration be $5\times10^6$ cells/mL for P388 cells and Erlich adenocarcinoma cells, $5\times10^5$ cells/mL for L1210 cells.

Eleven groups of animals with no less than 15 mice each were formed for experiments with either tumor cell line. Mice were inoculated with 0.2 mL of resultant cell suspensions per mouse ($10^6$ P388 and Erlich adenocarcinoma cells/mouse, and $10^5$ L1210 cells/mouse). 24 hours after the tumor cells inoculation, animals were given the first injections of the test articles or vehicles. The test article injections were made daily till the 14th day of the experiment or till the animal death. The volume of solutions injected comprised 0.01 mL/g body weight. Description of nine groups of animals formed for experiments with either tumor cell line is given below.

Control groups:
  #1—intact animals receiving imitation of tumor cell inoculation (injection of normal saline) which further were treated with normal saline throughout the entire experiment;
  #2—control animals, inoculated with tumor cells, which further were treated with test article vehicle (normal saline);

Experimental groups:
  #3—experimental animals, inoculated with tumor cells, which further were treated with test article (S-thioethylamine-GSSG dissolved in normal saline) in a dose of 5 mg/kg;
  #4—experimental animals, inoculated with tumor cells, which further were treated with a variant of test article drug form (S-thioethylamine-GSSG dissolved in normal saline containing 0.003% of hydrogen peroxide), with a dose of 5 mg/kg;
  #5—experimental animals, inoculated with tumor cells, which further were treated with a variant of test article drug form (S-thioethylamine-GSSG dissolved in normal saline containing 0.1% of inosine), with a dose of 5 mg/kg;
  #6—experimental animals, inoculated with tumor cells, which further were treated with a variant of test article drug form (S-thioethylamine-GSSG dissolved in normal saline containing 0.1% cystamine), with a dose of 5 mg/kg;
  #7—experimental animals, inoculated with tumor cells, which further were treated with a variant of test article drug form (S-thioethylamine-GSSG dissolved in normal saline containing 7% DMSO), with a dose of 5 mg/kg;
  #8—experimental animals, inoculated with tumor cells, which further were treated with test article (Li salt of GSSG dissolved in normal saline) in a dose of 5 mg/kg;
  #9—experimental animals, inoculated with tumor cells, which further were treated with a variant of test article drug form (Li salt of GSSG dissolved in normal saline containing 0.003% of hydrogen peroxide), with a dose of 5 mg/kg;
  #10—experimental animals, inoculated with tumor cells, which further were treated with a variant of test article drug form (Li salt of GSSG dissolved in normal saline containing 0.1% of inosine), with a dose of 5 mg/kg;
  #11—experimental animals, inoculated with tumor cells, which further were treated with a variant of test article drug form (Li salt of GSSG dissolved in normal saline containing 0.1% cystamine), with a dose of 5 mg/kg;
  #12—experimental animals, inoculated with tumor cells, which further were treated with a variant of test article drug form (Li salt of GSSG dissolved in normal saline containing 7% DMSO), with a dose of 5 mg/kg;
  #13—experimental animals, inoculated with tumor cells, which further were treated with a variant of drug form component (normal saline containing 0.003% of hydrogen peroxide), without GSSG;
  #14—experimental animals, inoculated with tumor cells, which further were treated with a variant of drug form component (normal saline containing 0.1% of inosine), without GSSG;
  #15—experimental animals, inoculated with tumor cells, which further were treated with a variety of drug form component (normal saline containing 0.1% of cystamine), without GSSG;
  #16—experimental animals, inoculated with tumor cells, which further were treated with a variant of drug form component (normal saline containing 7% of DMSO), without GSSG;

Tables 26–28 contain results on test article efficacy evaluation on integral parameters of the tumor process progression.

TABLE 26

Effect of the test articles on the accumulation of ascitic fluid and the mean survival time of mice inoculated with leukemia L1210 cells (M ± m)

| Group of animals | The number of injection | Accumulation of ascitic fluid (weight gain, %) | Mean survival time |
|---|---|---|---|
| Control animals | 0 | 0.7 ± 0.1 | 9.02 ± 0.19 |
|  | 3 | 7.14 ± 0.9 |  |
|  | 7 | 25.4 ± 2.6 |  |
| Intact animals | 0 | 0.2 ± 0.1 | 35 ± 0 |
|  | 3 | 1.12 ± 0.3 |  |
|  | 7 | 4.6 ± 1.2 |  |
| S-thioethylamine-GSSG + normal saline | 0 | 0.77 ± 0.2 | 19.2 ± 0.8 |
|  | 3 | 3.1 ± 0.4 |  |
|  | 7 | 9.2 ± 1.2 |  |
| S-thioethylamine-GSSG + 0.003% $H_2O_2$ | 0 | 0.56 ± 0.2 | 19.8 ± 0.6 |
|  | 3 | 2.9 ± 0.4 |  |
|  | 7 | 8.6 ± 1.4 |  |
| S-thioethylamine-GSSG + 0.1% inosine | 0 | 0.42 ± 0.3 | 21.2 ± 0.8 |
|  | 3 | 2.2 ± 0.6 |  |
|  | 7 | 7.8 ± 1.4 |  |
| S-thioethylamine-GSSG + 0.1% cystamine | 0 | 0.51 ± 0.1 | 19.8 ± 1.8 |
|  | 3 | 3.4 ± 0.4 |  |
|  | 7 | 8.6 ± 2.1 |  |
| S-thioethylamine-GSSG + 7% DMSO | 0 | 0.42 ± 0.3 | 22.2 ± 1.2 |
|  | 3 | 2.8 ± 1.0 |  |
|  | 7 | 6.6 ± 2.1 |  |
| Li salt of GSSG + normal saline | 0 | 1.27 ± 0.2 | 12.2 ± 0.1 |
|  | 3 | 4.1 ± 0.4 |  |
|  | 7 | 12.2 ± 1.2 |  |
| Li salt of GSSG + 0.003% $H_2O_2$ | 0 | 1.56 ± 0.2 | 14.8 ± 0.6 |
|  | 3 | 4.9 ± 0.4 |  |
|  | 7 | 10.6 ± 1.7 |  |
| Li salt of GSSG + 0.1% inosine | 0 | 1.42 ± 0.3 | 12.2 ± 1.2 |
|  | 3 | 4.2 ± 0.6 |  |
|  | 7 | 9.8 ± 1.0 |  |
| Li salt of GSSG + 0.1% cystamine | 0 | 1.51 ± 0.1 | 13.8 ± 1.6 |
|  | 3 | 3.4 ± 0.4 |  |
|  | 7 | 10.6 ± 1.7 |  |
| Li salt of GSSG + 7% DMSO | 0 | 2.42 ± 0.3 | 15.2 ± 1.4 |
|  | 3 | 5.8 ± 1.0 |  |
|  | 7 | 12.6 ± 1.7 |  |

TABLE 26-continued

Effect of the test articles on the accumulation of ascitic fluid and the mean survival time of mice inoculated with leukemia L1210 cells (M ± m)

| Group of animals | The number of injection | Accumulation of ascitic fluid (weight gain, %) | Mean survival time |
|---|---|---|---|
| 0.003% H$_2$O$_2$ | 0 | 0.77 ± 0.2 | 9.2 ± 0.8 |
| | 3 | 6.1 ± 0.4 | |
| | 7 | 19.2 ± 2.2 | |
| 0.1% inosine | 0 | 0.56 ± 0.2 | 9.8 ± 0.6 |
| | 3 | 7.9 ± 0.4 | |
| | 7 | 26.6 ± 2.4 | |
| 0.1% cystamine | 0 | 0.42 ± 0.3 | 10.2 ± 0.8 |
| | 3 | 8.2 ± 0.6 | |
| | 7 | 24.8 ± 2.1 | |
| 7% DMSO | 0 | 0.51 ± 0.1 | 10.8 ± 1.8 |
| | 3 | 6.4 ± 1.4 | |
| | 7 | 23.6 ± 2.6 | |

TABLE 27

Effect of the test articles on the accumulation of ascitic fluid and the mean survival time of mice inoculated with Erlich adenocarcinoma cells (M ± m)

| Group of animals | The number of injection | Accumulation of ascitic fluid (weight gain, %) | Mean survival time |
|---|---|---|---|
| Control animals | 0 | 0.7 ± 0.1 | 9.6 ± 0.3 |
| | 3 | 9.2 ± 1.2 | |
| | 7 | 28.4 ± 1.6 | |
| Intact animals | 0 | 0.2 ± 0.1 | 35 ± 0 |
| | 3 | 2.2 ± 0.3 | |
| | 7 | 5.1 ± 1.2 | |
| S-thioethylamine-GSSG + normal saline | 0 | 0.8 ± 0.1 | 16.2 ± 1.2 |
| | 3 | 3.2 ± 0.6 | |
| | 7 | 10.2 ± 2.2 | |
| S-thioethylamine-GSSG + 0.003% H$_2$O$_2$ | 0 | 0.6 ± 0.1 | 15.2 ± 1.1 |
| | 3 | 3.9 ± 0.6 | |
| | 7 | 9.2 ± 0.8 | |
| S-thioethylamine-GSSG + 0.1% inosine | 0 | 0.4 ± 0.2 | 17.2 ± 0.9 |
| | 3 | 3.2 ± 0.5 | |
| | 7 | 8.8 ± 1.1 | |
| S-thioethylamine-GSSG + 0.1% cystamine | 0 | 0.5 ± 0.2 | 16.8 ± 1.2 |
| | 3 | 3.7 ± 0.3 | |
| | 7 | 9.6 ± 1.7 | |
| S-thioethylamine-GSSG + 7% DMSO | 0 | 0.4 ± 0.1 | 17.2 ± 1.4 |
| | 3 | 4.8 ± 1.1 | |
| | 7 | 8.6 ± 1.4 | |
| Li salt of GSSG + normal saline | 0 | 1.2 ± 0.3 | 12.2 ± 0.1 |
| | 3 | 8.1 ± 0.4 | |
| | 7 | 17.2 ± 1.4 | |
| Li salt of GSSG + 0.003% H$_2$O$_2$ | 0 | 1.5 ± 0.2 | 14.8 ± 0.6 |
| | 3 | 6.9 ± 0.6 | |
| | 7 | 15.6 ± 1.6 | |
| Li salt of GSSG + 0.1% inosine | 0 | 1.4 ± 0.2 | 12.4 ± 1.4 |
| | 3 | 9.1 ± 0.5 | |
| | 7 | 15.2 ± 1.3 | |
| Li salt of GSSG + 0.1% cystamine | 0 | 1.7 ± 0.3 | 13.2 ± 1.2 |
| | 3 | 9.4 ± 0.2 | |
| | 7 | 16.6 ± 1.4 | |
| Li salt of GSSG + 7% DMSO | 0 | 2.4 ± 0.2 | 13.2 ± 1.6 |
| | 3 | 9.8 ± 1.0 | |
| | 7 | 17.6 ± 2.7 | |
| 0.003% H$_2$O$_2$ | 0 | 0.9 ± 0.2 | 9.8 ± 0.8 |
| | 3 | 14.1 ± 0.6 | |
| | 7 | 27.2 ± 1.2 | |
| 0.1% inosine | 0 | 0.8 ± 0.2 | 10.1 ± 0.6 |
| | 3 | 11.9 ± 0.2 | |
| | 7 | 26.8 ± 2.1 | |
| 0.1% cystamine | 0 | 0.6 ± 0.2 | 10.2 ± 0.8 |
| | 3 | 9.2 ± 0.8 | |
| | 7 | 25.8 ± 1.7 | |
| 7% DMSO | 0 | 0.5 ± 0.2 | 10.3 ± 1.8 |
| | 3 | 11.4 ± 1.1 | |
| | 7 | 24.6 ± 2.2 | |

TABLE 28

Effect of the test articles on the accumulation of ascitic fluid and the mean survival time of mice inoculated with leukemia P388 cells (M ± m)

| Group of animals | The number of injection | Accumulation of ascitic fluid (weight gain, %) | Mean survival time |
|---|---|---|---|
| Control animals | 0 | 0.7 ± 0.1 | 21.2 ± 0.3 |
| | 3 | 4.14 ± 0.9 | |
| | 7 | 18.2 ± 1.6 | |
| Intact animals | 0 | 0.2 ± 0.1 | 35 ± 0 |
| | 3 | 1.2 ± 0.3 | |
| | 7 | 4.8 ± 1.2 | |
| S-thioethylamine-GSSG + normal saline | 0 | 0.7 ± 0.2 | 28.2 ± 0.8 |
| | 3 | 2.1 ± 0.4 | |
| | 7 | 8.2 ± 1.2 | |
| S-thioethylamine-GSSG + 0.003% H$_2$O$_2$ | 0 | 0.6 ± 0.2 | 29.8 ± 0.6 |
| | 3 | 2.9 ± 0.4 | |
| | 7 | 6.6 ± 1.2 | |
| S-thioethylamine-GSSG + 0.1% inosine | 0 | 0.4 ± 0.3 | 31.2 ± 0.8 |
| | 3 | 2.6 ± 0.6 | |
| | 7 | 6.8 ± 1.1 | |
| S-thioethylamine-GSSG + 0.1% cystamine | 0 | 0.5 ± 0.1 | 29.8 ± 2.8 |
| | 3 | 2.4 ± 0.4 | |
| | 7 | 6.6 ± 2.0 | |
| S-thioethylamine-GSSG + 7% DMSO | 0 | 0.4 ± 0.1 | 22.2 ± 1.2 |
| | 3 | 2.6 ± 1.0 | |
| | 7 | 6.2 ± 1.4 | |
| Li salt of GSSG + normal saline | 0 | 1.2 ± 0.2 | 32.2 ± 0.1 |
| | 3 | 4.1 ± 0.4 | |
| | 7 | 11.2 ± 1.2 | |
| Li salt of GSSG + 0.003% H$_2$O$_2$ | 0 | 1.5 ± 0.2 | 24.6 ± 0.6 |
| | 3 | 4.9 ± 0.4 | |
| | 7 | 11.6 ± 1.7 | |
| Li salt of GSSG + 0.1% inosine | 0 | 1.4 ± 0.3 | 28.2 ± 1.2 |
| | 3 | 4.2 ± 0.6 | |
| | 7 | 8.8 ± 1.0 | |
| Li salt of GSSG + 0.1% cystamine | 0 | 1.5 ± 0.1 | 26.8 ± 1.6 |
| | 3 | 3.4 ± 0.4 | |
| | 7 | 10.6 ± 1.7 | |
| Li salt of GSSG + 7% DMSO | 0 | 2.4 ± 0.3 | 27.2 ± 1.4 |
| | 3 | 5.8 ± 1.0 | |
| | 7 | 8.6 ± 1.2 | |
| 0.003% H$_2$O$_2$ | 0 | 0.7 ± 0.2 | 21.2 ± 0.8 |
| | 3 | 4.1 ± 0.4 | |
| | 7 | 19.0 ± 2.1 | |
| 0.1% inosine | 0 | 0.5 ± 0.2 | 21.8 ± 0.6 |
| | 3 | 3.9 ± 0.4 | |
| | 7 | 16.6 ± 2.6 | |
| 0.1% cystamine | 0 | 0.4 ± 0.3 | 20.2 ± 0.8 |
| | 3 | 5.2 ± 0.6 | |
| | 7 | 18.8 ± 1.1 | |
| 7% DMSO | 0 | 0.5 ± 0.1 | 20.6 ± 1.8 |
| | 3 | 5.4 ± 1.4 | |
| | 7 | 19.6 ± 1.6 | |

The most prominent antitumor effect in respect to slow-down of ascitic fluid accumulation and prolongation of the mean survival time for either tumor models (P388, L1210 leukemia and Erlich adenocarcinoma) were obtained with S-thioethylamine-GSSG in combination with 0.1% inosine and 7% DMSO.

EXAMPLE 15

Effect of Zinc Salt of GSSG and S-thioethylamine-GSSG and Their Drug Forms on the Course of Experimental Allergic Encephalomyelitis (EAE), the Experimental Model of Multiple Sclerosis The action of the zinc salt of GSSG in the combination with S-thioethylamine-GSSG in 0.003% solution of $H_2O_2$ (10 mg GSSG and 100 mg S-adenosyl-methyonine in 1 ml) and S-thioethylamine-GSSG in 5% solution of ascorbinic acid were assessed in the model of EAE.

Within the frames of this study the influence of 10 day course of the named combinations on the cellular contents of blood (leukocyte, lymphocyte, monocyte, neutrophil count) was assessed. To assess cellular hypersensitivity to myelin basic protein and antigen of neuronal membranes, in vitro migration activity of leukocytes in the peripheral blood was investigated in the presence of these antigens. We also used capillary method of reaction of inhibition of leukocyte migration (RILM). Neurological evaluation was carried out as well.

The study was done on male quinea-pigs with body weight 400–500 g.

Encephalitis—inducing substance—myelin basic protein (MBP) was obtained from the bull spinal cord with the use of the method of column chromatography and emulsified on complete Freund adjuvant. Immunization of the animals was performed via inoculation of encephalitis-inducing mixture subcutaneously to the front paws (MBP+complete Freund adjuvant). Latency period of clinically expressed EAE averaged about 14–15 days, with minimun of 12 days.

Control groups:
1—Intact animals in which physiological solution was used;
2—animals exposed to with encephalitis-inducing mixture who then received physiological solution.

Experimental groups:
3—animals exposed to encephalitis-inducing mixture who then received zinc salt of glutation (GSSG-Zn) in the combination with S-adenosyl-methyonine in 0.003% solution of $H_2O_2$, 5 mg of GSSG base per kg of body weight.
4—animals exposed to encephalitis-inducing mixture who then received S-thioethylamine-GSSG in 5% solution of ascorbinic acid, 5 mg of GSSG base per kg of body weight Neurological evaluation (scoring):
1 muscle weakness, discoordination of movements;
2 paresis of paws, urinary bladder atonia, urination disorders;
3 motor and functional palsies (pelvic organs);
4 blood circulation and thermoregulation disorders;
5 agony, Cheyne-Stocks breathing.

Methods for cellular immunity evaluation
1. Reaction of Inhibition of Leukocyte Migration (RILM)—is a variant of Delayed Hypersensitivity reaction in vitro. Basics of the method: changes in migration activity of peripheral blood leukocytes during contact with MB in glass capillaries. Migration zones are measured with ocular micrometer of the microscope. Migration index is calculated as the extent of migration of the cells with antigen to spontaneous migration (without antigen) ratio. Statistically significant is the change of the index by more than 0.2, ie migration index less than 0.8 is considered suppression.
2. Spontaneous adhesion of blood leukocyte and its changes during contact with MBP. Migration of blood cells via vessel endothelium is a key moment in the development of inflammatory lesions in EAE. This process is determined by the combined action of adhesive molecules, expressed on leukocytes and endothelium. Suppression of adhesive properties of leukocytes by antigen indicates specific sensitization of immunized animals; changes in this parameter during inhibition characterizes immunotropic properties of the drug towards cellular immunity.
3. Adhesive activity of the cells is studied by the test of adhesion to micropanels Falkon Plastic 3034 with fluorescent assessment of the results and is expressed as the number of cells that adhere to the panels spontaneously or after antigen exposure.
Calculation of the adhesion index:
(1—adhesion with antigenispontaneous)×100 adhesion
Index>30 shows the reaction of suppression of spontaneous adhesion.

24 hours after the completion of the treatment with test articles survived animals were killed and the number of spleen cells was counted in sterile conditions. In the same time blood samples were taken to assess cellular counts.

Data reflecting the effects of the test articles on animal survival and neurological status are represented in tables 29 and 30. According to these data, the use of GSSG-Zn and methyonil preparations helps increase survival of the animals and significantly decrease neurological symptoms of EAE (see tables 29 and 30).

In tables 31 and 32 the results indicating the influence of the test articles on immunological EAE parameters are shown. The data demonstrate a significant effect of the test articles on the parameters of sensitization of blood lymphocytes to brain antigens. In the same time there is a significant decrease in sensitization of lymphocytes in RILA (Table 31) and RILM (Table 32).

TABLE 29

Animal mortality during the experiment

| Animal groups | Total number of animals | Died before the first injection of the test articles | Died during the treatment with the test articles | Total number of animals died |
|---|---|---|---|---|
| [1]1 | 20 | — | — | — |
| [1]2 | 20 | 4 | 7 | 11 |
| [1]3 | 20 | 5 | — | 5 |
| [1]4 | 20 | 3 | 1 | 4 |

TABLE 30

Extent of neurological symptoms (score)

| Animal groups | Number | Before the treatment with the test articles | Number | During the treatment with the test articles |
|---|---|---|---|---|
| $1_1$ | 20 | — | 20 | — |
| $1_2$ | 16 | 3.06 | 9 | 3.22 |
| $1_3$ | 15 | 3.00 | 15 | 2.06 |
| $1_4$ | 17 | 3.10 | 16 | 2.50 |

TABLE 31

Parameters of sensitization of blood lymphocytes of quinea-pigs with EAE to brain antigens in RILA (%, before/after the treatment with the test articles)

| | Animal groups | | | |
|---|---|---|---|---|
| Antigen | $1_1$ | $1_2$ | $1_3$ | $1_4$ |
| Myelin Basic Protein | — | 64.20 / 78.08 | 68.40 / 34.86 | 70.22 / 42.12 |
| Neuronal membrane antigen | — | 50.10 / 62.48 | 48.14 / 26.10 | 54.76 / 38.26 |

TABLE 32

Parameters of sensitization of blood lymphocytes of quinea-pigs with EAE to brain antigens in RILM (migration index, before/after the treatment with the test articles)

| | Animal groups | | | |
|---|---|---|---|---|
| Antigen | $1_1$ | $1_2$ | $1_3$ | $1_4$ |
| Myelin Basic Protein | 1.11(±0.08) | 0.52(±0.10) / 0.38(±0.09) | 0.46(±0.08) / 0.88(±0.11) | 0.54(±0.12) / 0.74(±0.06) |
| Neuronal membrane antigen | 1.20(±0.14) | 0.68(±0.06) / 0.42(±0.12) | 0.60(±0.04) / 0.92(±0.06) | 0.58(±0.06) / 0.82(±0.10) |

In new Examples 16–26, the following truncated designations for chemically modified GSSG derivatives are used:

| | |
|---|---|
| S-thioethylamine-glutathione disulfide | S-thioethylamine-GSSG |
| bis-[6,8-thioctanil]•eglutathione disulfide | bis-lipoil-GSSG |
| [b-alanyl-hystidil]•glutathione disulfide | carnosil-GSSG |
| [9-β-D-ribofuranosyladenil]•glutathione disulfide | adenosil-GSSG |
| bis-[2-amino-[methylthio]butanoil]•glutathione disulfide | bis-methionil-GSSG |

EXAMPLE 16

Therapeutical Effect of GSSG Series Preparations in Patient with Severe Form of Acute Virus Hepatitis A 32-year old male was hospitalized into infectious clinic with symptoms of pigment metabolism disorder: icterus of skin and mucous membranes; dark urine; light-colored faeces, high level of urobilinogen. The physical status of the patient was quite severe: body temperature—38.8° C., influenza-like and arthralgic syndromes. The patient's liver was enlarged more than on 4–5 cm. Acute virus hepatitis was diagnosed. The specified diagnosis was acute virus hepatitis "B". Severe form of the disease with acute hepatic insufficiency.

The first course of the treatment with the use of GSSG series preparations comprised intravenous injections of GSSG-Na$_2$ in 0.1% solution of folic acid, once a day during 7 days at a dose of 0.1–0.5 mg/kg of body weight.

The second course of the treatment comprised intravenous injections of GSSG-Zn in 0.1% solution of inosine once a day during 7 days at a dose of 0.1 mg/kg of body weight.

The third course comprised intravenous injections of GSSG-Na$_2$ in 5% solution of ascorbic acid every other day during 7 days at a dose of 0.1–0.5 mg/kg of body weight. Simultaneously the same formulation was injected intramuscularly at the same dose one time a day.

The data in Table 33 show the beneficial changes hematology/immunology parameters, decrease in (or/and normalization of) hepatitis laboratory markers. Thus, elimination of pathologic process and the patient's recovery occurred to be 1.5–2 months earlier than ordinary period of recovery in acute virus hepatitis.

TABLE 33

Changes in hematological, immunological, serological and biochemical parameters during 24 days after beginning the treatment with the use of GSSG series preparations

| Parameter | Prior to the treatment | 24 days after the treatment beginning |
|---|---|---|
| Hematology/Immunology | | |
| Erythrocytes | $3.65 \times 10^{12}$/L | $\times 10^{12}$/L |
| Hemoglobin | 96 g/L | 128 g/L |
| Leukocytes | $12.6 \times 10^9$/L | $7.8 \times 10^9$/L |
| Lymphocytes | $1.1 \times 10^9$/L | $2.9 \times 10^9$/L |
| Platelets | $180 \times 10^9$/L | $240 \times 10^9$/L |
| ESR | 28 mm/hour | 12 mm/hour |
| CD3$^+$ | $711 \times 10^6$/L | $1319 \times 10^6$/L |
| CD4$^+$ | $410 \times 10^6$/L | $655 \times 10^6$/L |
| CD8$^+$ | $305 \times 10^6$/L | $662 \times 10^6$/L |
| Circulate Immune Complexes | 142 units | 108 units |
| IFNα | 368.0 pg/mL | 906.0 pg/mL |
| IFNγ | 102.0 pg/mL | 608.0 pg/mL |
| IL-6 | 245.9 pg/mL | 653.0 pg/mL |
| Serology | | |
| Hbs Ag | + | − |
| Hbe Ag | + | − |
| IgM Anti Hbs | + | + |
| Anti Hbe | − | + |
| Anti Hbs Ag | − | + |
| Blood Chemistry | | |
| Bilirubin | | |
| -total | 180 μmol/L | 28.5 μmol/L |
| -direct reacting | 31 μmol/L | 6.1 μmol/L |
| ALT | 910 U/L | 90.8 U/L |
| AST | 206 U/L | 22 U/L |
| Alkaline phosphatase | 1316 U/L | 206 U/L |
| Serum cholinesterase | 24 μmol/L | 268 μmol/L |
| γ-Glutamyl transpeptidase | 205 IE/L | 39 IE/L |
| Prothrombin Index of p | 38% | 87% |
| Acid-base balance | metabolic alkalosis | normal |

EXAMPLE 17

Therapeutical Effect of GSSG Series Preparations in Patient with Chronic Virus Hepatitis in Stage of Exacerbation A 56-year old female was hospitalized into infectious clinic with complaint of physical status worsening, weakness, fatigue and irritability, anorexia, nausea. She also had some GIT symptoms, pain in right sub-costal area and body temperature up to 38.5° C.

On examination: The general status of the patient was of middle severity. Palpation revealed splenomegaly and hepatomegaly. Liver protruded 3 cm from under the rib arch. Sclerae and mucous membranes were subicteric.

Ultrasonic examination: Liver was remarkably enlarged, v. portae was 15 mm, the gall-bladder wall was thickened, pancreas had normal structure, spleen was enlarged (578× 168 mm) and thickened. Kidneys were without remarked alterations of structure.

During 2 weeks the patient was receiving desintoxication and antiviral therapy (Roferon-A, a recombinant $\alpha_2$-interferon). Because of a further disease progress and inefficacy of the therapy used, the decision was taken to try the treatment with GSSG series preparations.

Intravenous injections of GSSG-Na$_2$ in 10% solution of choline-chloride were applied during 7 days, (once a day at a dose of 0.1–1.0 mg /kg of body weight).

Intravenous injections of bis-methionil-GSSG in 5% solution of ascorbic acid were applied during the subsequent 10 days (once a day at a dose of 0.1–0.5 mg/kg of body weight). Simultaneously, intramuscular injections of GSSG-Na$_2$ in 0.1% solution of inosine were applied during these 10 days (once a day at a dose of 0.01–0.5 mg/kg of body weight).

One month after the aforementioned treatment with GSSG series preparations the patient's physical condition improved significantly. Only the complaints of weakness and fatigue remained. Diminution in algetic and dyspeptic syndromes was remarkable, body temperature was normal. Some beneficial changes in laboratory indices were observed (see table 2). Ultrasonic examination revealed the same extent of splenomegaly and hepatomegaly.

Due to the certain improvement in the patient's status, but remaining of hepatic lesion signs the decision was taken to apply another course of treatment with the use of GSSG series preparations. After the second course of the completely the same treatment the patient had no complaints. Pain and dyspeptic signs were absent. Ultrasonic examination revealed diminution in spleen and liver dimensions. Palpation revealed liver protruded 1.5 cm from under the rib arch. (For laboratory data see table 34).

Thus, the application of combined therapy with the use of GSSG series preparations conditioned a remarkable curative effect, with improvement in physical status and life quality, stabilization and reversion of the pathologic process, beneficial laboratory changes.

TABLE 34

Changes in hematological, immunological, serological and biochemical parameters after the 1st and 2nd courses of the treatment with the use of GSSG series preparations

| Parameter | Prior to the treatment | After the 1st course of the treatment | After the 2nd course of the treatment |
|---|---|---|---|
| Hematology | | | |
| Erythrocytes $10^{12}$/L | 3.79 | 4.3 | 4.85 |
| Hemoglobin g/L | 128 | 126 | 133 |
| Leukocytes $10^9$/L | 3.6 | 3.9 | 5.6 |
| Lymphocytes $10^9$/L | 900 | 1600 | 2900 |
| Platelets $10^9$/L | 140 | 156 | 220 |
| ESR mm/hour | 23 | 18 | 11 |
| Immunology | | | |
| Â-lymphocytes (ÑD20$^+$)$10^6$/L | 270 | 302 | 389 |
| ÑD4$^+$ $10^6$/L | 374 | 407 | 936 |
| ÑD8$^+$ $10^6$/L | 204 | 612 | 727 |

TABLE 34-continued

Changes in hematological, immunological, serological and biochemical parameters after the 1st and 2nd courses of the treatment with the use of GSSG series preparations

| Parameter | Prior to the treatment | After the 1st course of the treatment | After the 2nd course of the treatment |
|---|---|---|---|
| CD25$^+$ $10^6$/L | 228 | 246 | 680 |
| Circulating Immune Complexes | 190 | 170 | 106 |
| IgÀ, g/L | 5.6 | 5.2 | 1.2 |
| IgM, g/L | 6.9 | 6.0 | 4.8 |
| IgG, g/L | 29.0 | 18.9 | 3.4 |
| IFNα pg/mL | 304.6 | 200.8 | 128.6 |
| IFNγ pg/mL | 215.2 | 110.0 | 78.1 |
| IL-1β, pg/mL | 405.5 | 198.0 | 158.9 |
| IL-6, pg/mL | 603.9 | 430.6 | 190.2 |
| Serology | | | |
| HBs Ag | + | + | − |
| anti-HBS | − | + | + |
| anti-HBs-IgM | − | + | + |
| HBeAg | + | − | − |
| anti-IAe | − | + | + |
| Blood Chemistry | | | |
| Bilirubin | | | |
| -total µmol/L | 46.0 | 28.4 | 20.8 |
| -direct reacting µmol/L | 27.0 | 15.7 | 6.2 |
| ALT U/L | 9.1 | 4.3 | 1.2 |
| AST U/L | 0.8 | 0.7 | 0.5 |
| Alkaline phosphatase U/L | 12.6 | 8.2 | 7.8 |
| γ-Glutamyl transpeptidase IE/L | 208 | 190 | 41 |
| Total protein g/L | 91 | 89 | 78 |
| Albumin, % | 40 | 44 | 60 |
| $\alpha_1$-globulin, % | 6.2 | 6.4 | 5.2 |
| $\alpha_2$-globulin, % | 7.4 | 7.5 | 9.0 |
| β-globulin, % | 16.82 | 16.2 | 12.6 |
| γ-globulin, % | 29.58 | 25.9 | 13.2 |

EXAMPLE 18

Therapeutical Effect of GSSG Series Preparations in Patients with Acute Peritonitis 1. A 78-year old female was hospitalized with diagnosis of incarcerated ventral hernia, acute intestinal obstruction with necrosis of the small intestine and developing toxic phase of acute peritonitis. During the surgical operation approximately 800 ml of feculent effusion with flakes and fibrin clots was found in and removed from the abdominal cavity. Incarcerated part of small intestine was necrotized.

A partial resection of the small intestine with creating anastomose was performed. A probe was conducted into the small intestine through the esophagus and stomach and placed to ileocecal angle. During postoperative period the evacuation of intestine contents was performed once a day. After that 150 ml of 0.1% solution of folic acid in dimethyl sulfoxide (DMSO), comprising 10 ml of 1% GSSG disodium salt solution was instilled into the small intestine. Simultaneously 0.1% solution of folic acid and 1% GSSG disodium salt solution was injected intravenously at a dose from 0.01 to 0.1 mg/kg once a day during the 4 days.

An adequate peristalsis restored on the 2$^{nd}$ day after surgery. The probe was removed on the 8$^{th}$ day. The patient was checked out from the hospital on the 19$^{th}$ day.

2. A 16-year old male was hospitalized with a diagnosis of acute commissure-induced obstruction of small intestine with development of the peritonitis; toxic phase.

During the operation approximately 600 ml of feculent effusion with flakes and fibrin clots was found in and removed from the abdominal cavity. The patient had a prominent commissure process. A commissurotomy was made. A probe was conducted into the small intestine through the esophagus and stomach and placed to ileocecal angle.

During postoperative period the evacuation of bowel contents was performed once a day. After that 150 ml of 0.1% solution of folic acid in dimethyl sulfoxide (DMSO), comprising 10 ml of 1% GSSG disodium salt solution was injected into the small intestine. Simultaneously 0.1% solution of folic acid and 1% GSSG disodium salt solution was injected intravenously at a dose from 0.01 to 0.1 mg/kg once a day during the 4 days.

An adequate peristalsis renewed on the $2^{nd}$ day, and probe was removed on the $8^{th}$ day after surgery. The patient was checked out from the hospital on the $11^{th}$ day.

EXAMPLE 19

Therapeutical Effect of GSSG Series Preparations in Patient with Cancer of the Prostate A 63-year old male was hospitalized in urology department with the suspicion of prostate cancer. Palpation revealed the enlarged, dense prostate. X-ray examination of thorax revealed metastasis in frontal parts of IV–VII ribs, as well as in cranium, vertebrae, pelvic and femoral bones. Cancer of prostate was diagnosed with multiple bone metastasis ($T_2N_2M_1$).

Course of treatment was applied during the 30 days and was conducted by the following scheme:
1. Intravenous injections of GSSG-Zn in 1% solution of inosine were made during 10 days once a day at a dose of 0.01–0.5 mg/kg of body weight. In all cases where Zn salts are used in the Examples of this application, two atoms of Zn are present with one atom between $X_1$ or $X_4$ and one atom between $X_2$ or $X_3$.
2. During the next 10 days injections of S-thioethylamine-GSSG were made endolymfaticaly once a day at a dose of 0.1–1.0 mg/kg of body weight.
3. During the next 10 days intravenous injections of GSSG-Zn in 1% solution of inosine were made every other day at a dose of 0.01–0.5 mg/kg of body weight.

After the treatment course the patient's condition improved significantly, pain in groin area became of less intensity, episodes of frequent urination reduced up to 2–3 times a night, edema of lower extremities decreased. Hematological examination revealed some beneficial changes (table[1] 3).

After checking out the patient received intramuscular injections of GSSG-Zn in 1% solution of inosine twice a week at a dose of 0.01–0.5 mg/kg of body weight.

More than 1 year later the patient was hospitalized again at the same urology department for examination and conducting of the repeated course with GSSG series preparations. The treatment scheme with the use of the GSSG series preparations was identical. The main therapeutical effects 3 months after the end of the second treatment session was considered as the following: Improvement in life quality; absence of lower extremity edema; regression of enlarged lymph nodes; absence of disury manifestations; decrease in size of prostate; beneficial X-ray dynamics (calcification of some particular metastasis in ribs and vertebrae); restoration of hematology and immunology indices.

TABLE 35

Variations of hematology and blood chemistry indices

| Parameter | Prior to the treatment | 1 month after the treatment beginning | 2 months after the treatment beginning |
| --- | --- | --- | --- |
| Erythrocytes, $10^{12}$/L | 3,8 | 3,9 | 4,0 |
| Hemoglobin, g/L | 110 | 114 | 128 |
| Leukocytes, $10^9$/L | 7,9 | 5,4 | 5,0 |
| Stub neutrophils, % | 4 | 4 | 2 |
| Segmented neutrophils, % | 75 | 57 | 38 |
| Lymphocytes, % | 16 | 27 | 41 |
| Monocytes, % | 3 | 12 | 6 |
| ESR, mm/hour | 38 | 28 | 12 |
| Platelets, $10^9$/L | 168 | 225 | 244 |
| ND3+, % | 32,6 | 44,8 | 72,2 |
| ND4+, % | 16,1 | 22,8 | 50,2 |
| ND8+, % | 11,0 | 15,4 | 16,9 |
| "Active" O-lymphocytes (bearing receptors to IL-2, CD25+) | 12,9 | 60, 2 | 62,4 |
| NE-cells (CD16+/ND56+), $\mu L^{-1}$ | 64 | 292 | 404 |
| A-lymphocytes (CD20+), % | 6,4 | 10,2 | 15,4 |
| Circulating Immune Complexes, units | 385 | 212 | 102 |
| Creatinine, mmol/L | 0,06 | 0,08 | 0,07 |
| Acid phosphatase, U/L | 324 | 218 | 164 |
| Alkaline phosphatase, U/L | 10,4 | 8,3 | 6,8 |
| Total bilirubin, mmol/L | 17,8 | 8,5 | 9,0 |
| Glucose, mmol/L | 4,8 | 4,3 | 4,9 |

EXAMPLE 20

Therapeutical Effect of GSSG Series Preparations in Patient with Cancer of the Pancreas In May 1996 56 year old male patient was admitted to the II surgical division of the Hospital N122. On admission the patient's condition was severe. The patient complained on: continuous band-like pain in the upper part of the abdomen, that worsened when the patient was lying on the back, appetite loss, nausea, vomiting, flatulence, diarrhea. Karnofsky index 40. On palpation: pain and tension of the abdominal muscles at the site of projection of the pancreas (Kerte's symptom). Pancreas was solid, with uneven surface, enlarged. The liver was solid, 4 cm below the lower rib.

On ultrasonic examination: pancreas was enlarged (head 7 cm, body 4 cm, tail 2.5 cm) with uneven borders, solid. Virsung duct was enlarged 0.7 cm. Liver was enlarged, right lobe 18 cm, left lobe 10 cm. Lower edge was rounded. Its edges were uneven, the structure was nonhomogeneous with multiple hyperechogeneous foci in the parenchyma (metastases). Diagnosis—cancer of the pancreas with liver metastases (T3N2M1).

Treatment: detoxification, protease inhibitors, narcotic analgesics.

Due to the fatal severity of the patient's condition and absence of any alternative treatment the decision was made to use treatment with GSSG series preparations.

The treatment scheme: zinc salt of GSSG (0.01–0.5 mg/kg) intravenously (every day twice a day for 10 days). For the next 10 days—zinc salt of GSSG (0.01–0.5 mg/kg/day) intravenously, every other day and zinc salt GSSG in 7% dimethyl sulfoxide (0.1–1.0 mg/kg/day) endolymphatically. For the next 10 days (third decade) zinc salt of GSSG (0.01–0.5 mg/kg/day) intravenously, twice a week.

After a month treatment patient's condition was moderately severe; periodical moderate pain in the left subcostal region. Karnofsky index—60. Narcotic analgesics were stopped, appetite increased. There was a tendency to improvement in the blood parameters.

During 3 weeks after the completing intravenous treatment course the patient was receiving zinc salt of GSSG (0.01–0.5 mg/kg) once a week, intramuscularly.

In June 1996: the patient was again admitted to the II surgical division of the hospital 122 for investigation and for conducting a new session of treatment with the use of GSSG series preparations.

On examination: marked improvement of the clinical condition and blood parameters (see Table 4). The patient's condition was almost satisfactory. Complains on a periodic weak pain in the left subcostal region. Karnofsky index—70. On palpation—some tenderness in the site of the projection of the head and body of the pancreas; the organ was less solid with a smoother surface.

On ultrasonic examination: some decrease in the size of pancreas (head 6.3 cm, body 3.2 cm, tail 2.1 cm). Virsung duct 0.4 cm. The liver was enlarged; the right lobe 16.5 cm, the left one–9.5 cm. Contours of the liver were uneven, structure—nonhomogeneous. Fibrosis of the porta hepatis. Multiple hyperechogeneous shadows in the liver parenchyma.

The treatment scheme for the second session of therapy with GSSG series preparations was the following. For the first 10 days, S-thioethylamine-GSSG was infused every day via catheter into the hepatic artery (0.1–1.0 mg/kg/day).

After that the zinc salt of GSSG (0.01–0.5 mg/kg) was given intravenously every day, for 10 days. Being checked out the patient received supportive therapy with the zinc salt of GSSG intravenously (0.01–0.5 mg/kg/day), once a week, for 1 month.

In September 1996 the patient was again admitted to the Hospital N122 for examination and the third session of therapy. Clinical condition did not change by that time. For blood parameter variations see table 36.

On ultrasonic examination: pancreas had the same characteristics as before. Liver was slightly enlarged, the right lobe—15 cm, the left lobe–8 cm, lower edge rounded, edges were definite and smooth, parenchyma was nonhomogeneous due to hypo and hyperechogeneous foci (fibrosis and calcificates).

Thus the following clinical effects were considered as prominent and significant: improvement of the quality of life; stabilization of the neoplastic process; resolution of some metastases; restoration of immunology and hematology indices; improvement in results of ultrasonic examination.

TABLE 36

Laboratory indices in patient with pancreas cancer throughout the observation period

| Parameter | Before treatment | After one month of treatment | After 3 months of treatment | After 6 months of treatment | Normal limits |
|---|---|---|---|---|---|
| Hematology and blood chemistry | | | | | |
| Erythrocytes, $10^{12}/l$ | 3.8 | 4.0 | 4.1 | 4.6 | 4.0–5.0 |
| Hemoglobin, g/l | 128 | 130 | 134 | 141 | 130.0–160.0 |
| Platelets, $10^9/l$ | 216 | 226 | 234 | 268 | 180.0–320.0 |
| Leukocytes, $10^9/l$ | 9.6 | 8.8 | 8.3 | 6.8 | 4.0–9.0 |
| Neutrophils and rods, % | 10 | 4 | 3 | 3 | 1–6 |
| Segmentonuclear neutrophils, % | 70 | 59 | 50 | 54 | 47–72 |
| Lymphocytes, % | 15 | 27 | 39 | 34 | 19–37 |
| Monocytes, % | 4 | 6 | 6 | 7 | 3–11 |
| Eosinophils, % | 6 | 4 | 2 | 2 | 0–11 |
| ESR, mm/h | 64 | 30 | 19 | 15 | 2–10 |
| Total protein, g/l | 74 | 72 | 69 | 71 | 65–85 |
| ALT/mmol/hL | 0.8 | 0.4 | 0.33 | 0.3 | 0.1–0.7 |
| AST/mmol/hL | 0.5 | 0.4 | 0.21 | 0.2 | 0.1–0.5 |
| α-amylase g/hL. | 46 | 30 | 21 | 18 | 12–32 |
| LDH MU/l | 1121 | 542 | 521 | 472 | <450 |

TABLE 36-continued

Laboratory indices in patient with pancreas cancer throughout the observation period

| Parameter | Before treatment | After one month of treatment | After 3 months of treatment | After 6 months of treatment | Normal limits |
|---|---|---|---|---|---|
| Immunology | | | | | |
| Lymphocytes | 1440 | 2376 | 3237 | 2312 | 1200–3000 |
| B-lymphocytes (CD20+) $10^6$/l | 272 | 348 | 554 | 392 | 200–400 |
| T-helpers (CD4+), $10^6$/l | 874 | 1114 | 1242 | 1092 | 700–1100 |
| T-suppressors (CD8+) $10^6$/l | 222 | 384 | 1082 | 721 | 500–900 |
| CD4+/CD8+ ratio | 3.94 | 1.63 | 1.15 | 1.51 | 1.0–1.5 |
| Circulating immune complexes | 362 | 194 | 136 | 108 | 50–100 |

EXAMPLE 21

Therapeutical Effect of GSSG Series Preparations in Patient with Diabetes Mellitus Female patient of 18 year old was admitted to the Division of Endocrinology of the Hospital N16. Diagnosis: insulin dependent diabetes mellitus (type I). Severe form of insulin resistance, diabetic angioretinopathy grade IV, initial symptoms of diabetic polyneuropathy III from the age 14. The disease started with precomatose state, blood glucose varied from 18.4 to 28.0 mmol/l, ketoneuria (acetone), and glucosuria up to 12%. Total Insulin dose at the disease onset: SU-Insulin 68 units, "ICS" 269 units. Previously was hospitalized several times. Dose of Insulin reached 500 units in 1994–1996. At that time blood glucose was 19.6–24.3 mmol/l, glucosuria was 4–6%, positive ketones in urine.

In September 1996 the patient was admitted to consider modification of treatment with the dose of ICS insulin 500 units, ICS-A 100 units, SU-Insulin 5-units. On admission Insulin dose was the following: B-insulin 480 units, SU insulin 22 units

| Blood sugars: | |
|---|---|
| 9 A.M. | 11.4 mmol/l |
| noon | 11.1 mmol/l |
| 2 P.M. | 13.9 mmol/l |
| 5 P.M. | 16.7 mmol/l |
| 6 A.M. | 10.7 mmol/l |
| Glucosuria - up to 670 mmol, ketones +++ | |

Due to the severity of the patients insulin resistance and after the patient's agreement the decision was made to use GSSG series preparations.

Treatment scheme: intravenously for 10 days, once a day GSSG-Na$_2$ in 0.5% solution of lipoic acid (0.01–0.5 mg/kg/day).

For the next 10 days, intravenously, every other day—zinc salt GSSG in 0.5% solution of lipoic acid (0.01–0.5 mg/kg/day).

For the next 10 days (third decade) sodium salt GSSG-Na$_2$ in 5% solution of ascorbic acid, intramuscularly, once a day for 20 days (0.1–0.5 mg/kg/day).

After the treatment session had been completed the insulin treatment was modified. SU insulin was started, several injections per hour, sustained release insulin canceled.

The dose of insulin was gradually decreased, and the patient was discharged with the following insulin regimen:

| 6 A.M. | 4 units SU-insulin |
|---|---|
| 9 P.M. | 50 units |
| 2 P.M. | 36 units |
| 7 P.M. | 36 units |
| 11 P.M. | 8 units (total dose 134 units). |

Blood sugars got to normal and did not exceed 8 mmol/l even after meals. After the patient was discharged she received therapy with GSSG series preparations as an outpatient for a month. Treatment scheme was the following:

During a month—sodium salt of GSSG in 0.5% solution of lipoic acid (0.01–0.5 mg/kg), intramuscularly, every other day.

During the 2 successive months the patient had two episodes of hypoglycemia (1.8–2.2 mmol/l), and that forced to decrease insulin doses. Thus, after the two months of treatment following insulin regimen was implemented:

| 6 A.M. | 4 units SU-insulin |
|---|---|
| 9 P.M. | 36 units |
| 2 P.M. | 12 units |
| 7 P.M. | 12 units |
| 11 P.M. | 4 units (total dose 68 units). |

The patient's condition was satisfactory, no complains. See table 37 for changes in blood parameters. Thus the following clinical effects seem to be substantial: stopped insulin resistance; decreased insulin dose, improvement of the quality of life and laboratory parameters.

TABLE 37

Hematology, blood chemistry and immunology parameters in patient with juvenile diabetes mellitus

| Parameter | Before treatment | After one month of treatment | After 2 months of treatment |
|---|---|---|---|
| Erythrocytes. $10^{12}$/l | 4.1 | 4.3 | 4.4 |
| Hemoglobin, g/l | 129 | 135 | 144 |
| Platelets, $10^9$/l | 205 | 222 | 275 |
| Leukocytes, $10^9$/l | 7.8 | 6.4 | 5.2 |
| Neutrophils and rods, % | 4 | 3 | 3 |
| Segmentonuclear neutrophils, % | 39 | 53 | 58 |
| Lymphocytes, % | 51 | 39 | 34 |
| Monocytes,% | 4 | 3 | 4 |
| Eosinophils, % | 2 | 2 | 1 |
| ESR, mm/h | 13 | 12 | 10 |

TABLE 37-continued

Hematology, blood chemistry and immunology parameters in patient with juvenile diabetes mellitus

| Parameter | Before treatment | After one month of treatment | After 2 months of treatment |
|---|---|---|---|
| ALT/mmol/hL | 0.44 | 0.38 | 0.22 |
| AST/mmol/hL | 0.3 | 0.3 | 0.3 |
| Total protein, g/l | 75 | 72 | 72 |
| Bilirubin, total, mcmol/l | 10.8 | 9.2 | 8.4 |
| Cholesterol, total, mcmol/l | 7.4 | 6.54 | 5.8 |
| Triglycerides, mcmol/l | 4.2 | 3.5 | 2.1 |
| Urea, mmol/l | 4.2 | 4.0 | 3.3 |
| Creatinine, mmol/l | 0.133 | 0.095 | 0.088 |
| B-lymphocytes (CD20+)$10^6$/l | 478 | 395 | 358 |
| T-helpers (CD4+), $10^6$/l | 1412 | 1014 | 874 |
| T-suppressors (CD8+) $10^6$/l | 1044 | 942 | 605 |
| $CD25^+$ | 422 | 512 | 495 |
| Circulating immune complexes | 214 | 123 | 95 |

EXAMPLE 22

Therapeutical Effect of GSSG Series Preparations in Patient with Lung Cancer

Diagnosis: Cancer of the upper lobe of the right lung (T3N2M0) extending into superior caval vein and pulmonary artery. Metastases to mediastinal lymph nodes.

In September 1995 a male patient of 59 was admitted to the surgical division of the Institute of Pulmonology with suggested lung neoplasm. On admission the patient was complaining of periodical fever up to 38.4° C., decreased appetite, 8 kg weight loss, dyspnea after movement.

On several chest CT scans (29.08.96) the size of the right lung was decreased due to hypoventilation of the upper lobe. Pulmonary tree looked different on the right side. Right upper lobe bronchus was narrowed and deformed, with a focal shadow 4.0×5.0×6.0 cm. There probably was an enlargement of paramediastinal lymph nodes. No fluid in pleural cavities.

On bronchoscopy: lymphangiitis of the lateral wall of the lower ⅓ of trachea, lymphangiitis and infiltration of the lateral wall of the right main bronchus, compressive and infiltrative stenosis of the right upper lobe bronchus (lateral wall) of the 1–2 degree.

On diagnostic thoracotomy: (14.09.95) uneven dense formation of the upper lobe of the right lung 4.0×5.0×6.0 cm, growing into upper parietal pleura. On intraoperative examination, after pericardium was opened it became obvious that neoplasm extended into superior caval vein and pulmonary artery. Histologically, neoplasm was identified as low differentiation (small cell) carcinoma. The case was considered inoperable.

The patient's state continued to deteriorate: right supraclavicular node enlarged (3.5×4.0 cm). The patient was transferred to the Institute of Oncology for chemotherapy. After the first treatment course of Cisplatine combined with Etoposide the patients' condition deteriorated significantly: nausea and vomiting, alopecia, increased transaminases, creatinine, leukopenia.

Due to the severity of the patient's disease and absence of any alternative treatment the decision was made to use compassionate treatment with lithium salt of GSSG.

From the first injections of GSSG-Li (0.01–0.5 mg/kg per day, intravenously/intramuscularly alternative days for 14 days), the quality of life improved significantly (Karnofsky index 80 (60), appetite increased, dyspnea decreased.

After 2 weeks' treatment with lithium salt of GSSG in 0.003% solution of $H_2O_2$ blood indices substantially improved (leukocyte count, red cell count, creatinine, transaminases), and that permitted to try another chemotherapy course (Cisplatine combined with Etoposide). Compared with the first course, there were no complications during the second one when the patient was receiving Li-GSSG: there was no nausea, vomiting, there was an increase in appetite (5 kgs weight gain); results of clinical and biochemical blood tests were within normal limits.

After the second chemotherapy course therapy with GSSG series preparations was resumed: lithium salt of GSSG in 3% of dimethyl sulfoxide (0.01–0.5 mg/kg per day intravenously/intramascualarly 3 times a week during 14 days).

Then the patient received another chemotherapy course in the Institute of Oncology. There were no complications during the third chemotherapy course. Result of blood tests were within normal limits. There were a complete resolution of the enlarged right supraclavicular lymph node and X-ray demonstrated improvement of the primary lesion; no signs of atelectasis, additional shadows were neither found in mediastimun, nor paratracheally; trachea had a normal location; there was no residual cavity.

Thus the 2 courses of chemotherapy combined with GSSG series preparations (lithium salt of GSSG) led to satisfactory quality of life, systemic regression of the neoplasm, restoration of laboratory parameters which was associated with a stable increase in endogenous production of cytokines and hematopoietic factors (see Table 38). Later on the patient was receiving GSSG-$Li_2$ at a dose rate 0.01–0.5 mg/kg, every other day for 14 days a month during a year.

TABLE 38

Laboratory parameters in patient with lung cancer throughout the observation period

| Parameter | Before treatment | After two months of treatment | After 4 months of treatment | After one year | Normal limits |
|---|---|---|---|---|---|
| Erythrocytes, $10^{12}$/l | 3.9 | 4.4 | 4.7 | 4.5 | 4.0–5.0 |
| Hemoglobin, g/l | 120 | 132 | 135 | 142 | 130.0–160.0 |
| Platelets, $10^9$/l | 396 | 235 | 282 | 270 | 180.0–320.0 |
| Leukocytes, $10^9$/l | 3.1 | 4.1 | 5.5 | 6.3 | 4.0–9.0 |
| Neutrophils and rods, % | 2 | 3 | 2.5 | 4 | 1–6 |

TABLE 38-continued

Laboratory parameters in patient with lung cancer throughout the observation period

| Parameter | Before treatment | After two months of treatment | After 4 months of treatment | After one year | Normal limits |
|---|---|---|---|---|---|
| Segmentonuclear neutrophils, % | 74 | 41 | 42 | 47 | 47–72 |
| Lymphocytes, % | 16 | 40 | 36 | 35 | 19–37 |
| Monocytes, % | 6 | 9 | 12 | 10 | 3–11 |
| Eosinophils, % | 1 | 5 | 5.5 | 4 | 0–11 |
| ESR, mm/h | 34 | 21 | 12 | 9 | 2–10 |
| Total protein, g/l | 61 | 78.4 | 80.6 | 78 | 65–85 |
| Albumin, % | 35.96 | 49.0 | 61.6 | 56 | 50–66 |
| α1-globulins, % | 10.32 | 4.0 | 2.8 | 4.7 | 2.5–5.0 |
| α2-globulins, % | 15.24 | 12.0 | 7.2 | 9.2 | 6.0–9.5 |
| β-globulins, % | 15.24 | 13.6 | 12.8 | 12.8 | 8.0–13.0 |
| γ-globulins, % | 23.33 | 21.4 | 15.6 | 17.3 | 13.0–17.0 |
| A/G ratio | 0.56 | 0.84 | 1.6 | 1.27 | 1.0–1.9 |
| Urea, mmol/l | 9.0 | 6.2 | 6.3 | 5.9 | 2.5–8.3 |
| Creatinine, mmol/l | 1.21 | 0.98 | 0.89 | 0.88 | 0.044–0.115 |
| Bilirubin, total, mcmol/l | 19.5 | 13.0 | 14.0 | 5.1 | 3.5–20.5 |
| Prothrombin index, % | 88 | 90 | 104 | 100 | 80–105 |
| Glucose, mmol/l | 7.1 | 5.4 | 5.3 | 4.6 | 3.3–6.1 |
| ALT/mmol/hL | 1.32 | 0.21 | 0.19 | 0.19 | 0.1–0.7 |
| AST/mmol/hL | 1.22 | 0.36 | 0.15 | 0.17 | 0.1–0.5 |
| Lymphocytes | 496 | 1640 | 1980 | 2205 | 1200–1300 |
| B-lymphocytes (CD20+) $10^6$/l | 101 | 232 | 392 | 372 | 200–400 |
| T-helpers (CD4+), $10^6$/l | 321 | 824 | 1020 | 1064 | 700–1100 |
| T-suppressors (CD8+) $10^6$/l | 74 | 484 | 654 | 608 | 500–900 |
| C04+/CD8+ ratio | 4.3 | 1.7 | 1.55 | 1.75 | 1.0–1.5 |
| Cells with IL-2 receptors (CD25+)/$10^6$/l | 202 | 472 | 682 | 605 | 208–576 |
| HLA(11) receptor, $10^6$/l | 294 | 392 | 472 | 541 | 304–720 |
| NK-cells (CD16+) $10^6$/l | 180 | 320 | 525 | 394 | 200–400 |
| IgA, g/l | 3.28 | 4.01 | 5.1 | 4.8 | 0.8–5.2 |
| IgM, g/l | 0.5 | 0.71 | 1.4 | 2.1 | 0.6–33.8 |
| IgG, g/l | 13.8 | 15.4 | 17.4 | 16.5 | 6.0–18.0 |
| Circulating immune complexes | 335 | 221 | 112 | 62 | 50–100 |
| IL-1β, pcg/ml | 19.8 | 178.6 | 294.8 | 132 | |
| TNF α, pcg/ml | 34.1 | 121 | 149 | 98 | |

One year later (14.10.96)

On chest CT scan there was a site of fibrous changes in the right upper lobe bronchus 1.5×1.5×2.0 cm. There were no new Infiltrative or fibrous changes in lung tissue. Lumens of the trachea and bronchi in both lungs were neither narrowed nor deformed. There was no mediastinal and lung root lymph node enlargement. No fluid in pleural cavities.

CONCLUSION

Combined treatment with chemotherapeutic regimens and GSSG-Li$_2$ produced remarkable potentiation of the chemotherapeutic effect with its acceptable chemotherapy tolerability. Generally, the effect of the combination led to tumor regression, liquidation of metastases, restoration of immune and hematopoietic systems, a better quality of life.

EXAMPLE 23

Therapeutical Effect of GSSG Series Preparations in Patient with Sigmoid Cancer

Diagnosis: Cancer (undifferentiated adenocarcinoma) of the rectosigmoid region of the colon (T4N0M0), complicated by right-sided adnextumor, right-sided tuboovarial abscess, diffuse phlegmonous-purulent peritonitis.

In June 1996 a female patient of 48 was urgently admitted to the II$^{nd}$ surgical division of the Central Hospital N122 with the above mentioned diagnosis.

Operation: loop sigmostoma, abdominal cavity cleaning and draining. The patient's condition was severe: Karnofsky 30, fever 39–40° C. Despite aggressive therapy clinical condition continued to deteriorate and complicated with bilateral pneumonia. Additional intensive therapy with antibiotics (Cefalosporins and Penicillins-Claforan 6 g/day, Ampicillin/Oxacillin 2 g/day) did not result in desirable effect.

Due to inefficacy of the treatment the decision was made to use compassionate treatment with GSSG-Zn$_2$.

For one week the patient received GSSG-Zn$_2$ in 0.1% solution of cystamine 0.01–0.5 mg/kg per day IV and IM together with the previous complex therapy. After one weeks' treatment the patient's physical status improved substantially, appetite increased, weakness disappeared, sleep normalized, local healing of the wound accelerated. There was a tendency for normalization of blood parameters (see Table 39), there were no XOray signs of pneumonia.

Those positive effects permitted to perform the second stage of the surgical treatment—to repeat laparotomy with resection of proctosigmoid region of colon and right adnexa with ovary. Postoperative period was characterized by right-sided lower lobe pleuropneumonia. Again, GSSG-Zn$_2$ in 0.1% cystamine solution was added to the treatment (0.01–0.5 mg/kg every day intravenously and intramuscularly during a week). Clinical and radiological signs of pneumonia resolved within 3 days.

There were no complications of the postoperative wound. Sutures were removed on the seventh day. Patient was discharged in satisfactory condition to be followed up as an out-patient.

General effects can be summarized as follows: improvement of the quality of life; potentiation of antibacterial therapy; restoration of laboratory indices; acceleration of wound-healing; possibility of radical surgical treatment.

Clinical and laboratory improvement permitted to introduce combined treatment with high-dose chemotherapy (5-Fluoruracil–10 g/course) which was combined with GSSG-$Zn_2$. During 3 days the patient was receiving Fluoruracil endolymphatically (day 1–3 g, day 2–3 g, day 3–4 g) and high doses of GSSG-$Zn_2$ in DMSO (0.1–1.0 mg/kg per day).

TABLE 39

Laboratory parameters in patient with sigmoid cancer throughout the observation period

| Parameter | Before treatment | After one week of treatment | After two weeks of treatment | After one month |
|---|---|---|---|---|
| Erythrocytes, $10^{12}/l$ | 3.2 | 3.8 | 3.8 | 4.1 |
| Hemoglobin, g/l | 112 | 126 | 130 | 132 |
| Platelets, $10^9/l$ | 200 | 220 | 274 | 248 |
| Leukocytes, $10^9/l$ | 24.0 | 9.1 | 8.2 | 7.8 |
| Neutrophils and rods, % | 13 | 6 | 6 | 5 |
| Segmentonuclear neutrophils, % | 66 | 60 | 58 | 50 |
| Lymphocytes, % | 12 | 26 | 28 | 36 |
| Monocytes, % | 3 | 5 | 5 | 7 |
| Eosinophils, % | 6 | 2 | 2 | 2 |
| ESR, mm/h | 62 | 18 | 15 | 12 |
| ALT/mmol/hL | 0.8 | 0.5 | 0.3 | 0.22 |
| AST/mmol/hL | 0.5 | 0.4 | 0.4 | 0.18 |
| IgA, g/l | 3.8 | 3.6 | 3.5 | 3.2 |
| IgM, g/l | 2.8 | 2.5 | 3.0 | 2.8 |
| IgG, g/l | 19.8 | 16.3 |  | 17.4 |
| Circulating immune complexes | 162 | 134 | 94 | 96 |

EXAMPLE 24

Therapeutical Effect of GSSG Series Preparations in Patient with Pancreas/Duodenum Cancer Diagnosis: Cancer of the pancreas extending into the duodenum (T3N2M1).

In January 1996 a male patient of 67 was admitted to the If surgical division of the Hospital N122 with obstructive jaundice. Diagnosis—infiltrative stricture of the main bile duct. Surgery: transcutaneous-transhepatic external-internal drainage.

In February 1996—cholecystectomy, choledocho-duodenoanostomosis (Jurash procedure). Patient was suffering from severe pain in the right subcostal area irradiating to the back, and narcotic analgesics were prescribed. No appetite. Weight loss 13 kg per month. Karnofsky index 40. Periodical nausea, vomiting, steatorrhea. Increased amylase and lipase in blood serum, amylase in urine, anemia. In the projection of the head of the pancreas tumorous object could be palpated. On fibrogastroduodenoscopy: infiltration of duodenal mucosa down to the Fater's papilla.

Due to the severity of the patient's disease, progressive deterioration and absence of any alternative treatment the decision was made to use compassionate treatment with GSSG-$Zn_2$ in dimethyl sulfoxide (DMSO).

After 2 weeks' treatment the patients condition obviously improved. Karnofsky index—80. Continuous pain decreased, though the patient was suffering from periodical moderate pains, narcotics were canceled. No nausea or vomiting; weight gain 4 kg; improvement in blood parameters (see Table 40).

The patient tolerated treatment without hematological and other toxic complications. (for blood parameters see Table 40). During the 3 consecutive months (February–April) the patient received supporting doses of GSSG-$Zn_2$ in DMSO (0.01–0.3 mg/day, intravenously and intramuscularly, 2 times a week). Patient's condition was quite good; Karnofsky index 90. No pains; good appetite; weight gain—8 kg.

3 months later (May, 1996), a 3 day course of high-dose chemotherapy together with GSSG-$Zn_2$ was conducted (total dose of fluoruracil—10 g; GSSG-$Zn_2$ 0 1–1.0 mg/kg, daily) without complications reported. The patient was discharged in satisfactory condition to be followed up as an out-patient. Treatment with GSSG-$Zn_2$ was continued for 3 successive months (0.01–0.5 mg/kg IV and IM 2 times a week).

6 months later (September 1996): the third course of high-dose chemotherapy according to the scheme shown above, with no complications. Patient's condition was satisfactory; Karnofsky index 90. Good appetite; no nausea or vomiting; Weight gain 12 kg from the beginning of the observation. On gastroduodenoscopy—significant decrease in infiltration of duodenal mucosa with signs of stabilizing the neoplastic process.

Thus the following effect of the combination of GSSG-$Zn_2$ and chemotherapy regimen can be stressed: improvement of the quality of life; resolution of pain; beneficial laboratory changes; stabilization of the neoplasm process; good tolerance of chemotherapy.

TABLE 40

Laboratory parameters in patient with pancreas/duodenum cancer throughout the observation period

| Parameter | Before treatment | After two weeks of treatment | After one months of treatment | After 3 months of treatment | After six months of treatment | Normal limits |
|---|---|---|---|---|---|---|
| Erythrocytes, $10^{12}$/l | 2.9 | 4.0 | 4.3 | 4.1 | 4.4 | 4.0–5.0 |
| Hemoglobin, g/l | 118 | 129 | 134 | 130 | 132 | 130.0–160.0 |
| Platelets, $10^9$/l | 178 | 228 | 242 | 204 | 218 | 180.0–320.0 |
| Leukocytes, $10^9$/l | 12.4 | 8.2 | 5.4 | 5.6 | 4.8 | 4.0–9.0 |
| Neutrophils and rods, % | 10 | 5 | 4 | 4 | 3 | 1–6 |
| Segmentonuclear neutrophils, % | 72 | 54 | 47 | 40 | 51 | 47–72 |
| Lymphocytes, % | 8 | 32 | 39 | 45 | 36 | 19–37 |
| Monocytes, % | 3 | 5 | 6 | 8 | 6 | 3–11 |
| Eosinophils, % | 7 | 4 | 4 | 3 | 4 | 0–11 |
| ESR, mm/h | 48 | 18 | 13 | 14 | 15 | 2–10 |
| Total protein, g/l | 54 | 69 | 72 | 68 | 70 | 65–85 |
| ALT/mmol/hL | 0.8 | 0.3 | 0.22 | 0.28 | 0.3 | 0.1–0.7 |
| AST/mmol/hL | 0.4 | 0.3 | 0.2 | 0.22 | 0.2 | 0.1–0.5 |
| α-amylase, g/hL | 112 | 33 | 28 | 26 | 20 | 12–32 |
| LDH MU/l | 1082 | 454 | 352 | 178 | 212 | <450 |
| Lymphocytes | 992 | 2624 | 2106 | 2520 | 1728 | 1200–3000 |
| B-lyphocytes (CD20+) $10^6$/l | 174 | 384 | 304 | 388 | 241 | 200–400 |
| T-helpers (CD4+), $10^6$/l | 514 | 825 | 932 | 926 | 834 | 700–1000 |
| T-suppressors (CD8+) $10^6$/l | 102 | 584 | 784 | 732 | 701 | 500–900 |
| CD4+/CD8+ ratio | 5.0 | 1.41 | 1.19 | 1.27 | 1.19 | 1.0–1.5 |
| CD25+ | 154 | 286 | 356 | 482 | 476 | 208–576 |
| NK-cels (CD16/56+) | 172 | 196 | 383 | 412 | 396 | 200–400 |
| IgA, g/l | 3.4 | 3.6 | 4.8 | 4.6 | 4.1 | 0.8–5.2 |
| IgM, g/l | 2.1 | 2.2 | 3.4 | 3.0 | 2.6 | 0.6–3.8 |
| IgG, g/l | 23.4 | 18.4 | 17.2 | 17.3 | 16.8 | 6.0–18.0 |
| Circulating immune complexes | 476 | 448 | 225 | 214 | 174 | 50–100 |

EXAMPLE 25

Therapeutical Effect of GSSG Series Preparations in Patient with Severe Postoperative Complications Diagnosis: Post-intubation scar stenosis of the trachea, tracheoesophageal fistula, post operative empyema of the right pleural cavity.

A male 22 year old patient was admitted to the surgical division of the State Scientific Center of Pulmonology of the Ministry of Health of Russia Federation in March 1996 after linear stent of the trachea was placed. After it was removed there was a relapse of the tracheal stenosis and the signs of tracheoesophageal fistula appeared. Due to this in April 1996 the operation was performed: circular resection of the trachea, closure of the TE fistula, omentoplastics.

During the postoperative period right-sided pleural empyema developed. Despite massive antibiotic therapy, detoxification and pleural cavity drainage, the patient's state was very severe. The patient was pale, pulse 120/min, rhythmic, BP 90150 mm Hg, breathing rate 28/min, slightest physical exertion caused dyspnea, t 38.8–39.6° C.

On chest X-ray: increased density of the left lung due to diffuse infiltration (edema). Paracostally in the lateral areas along the rib cage and posteriorly in the interlobular fissures there was a lot of fluid. Enlarged median shadow in the upper region.

Significant leukocytosis (30×$0^9$/l), increased neutrophil count, increased ESR (58 mm/h), hypertransaminasemia (see Table 9).

Due to the severity of the patients disease, pulmonary insufficiency and absence of any alternative treatment the decision was made to use compassionate treatment with lithium salt of GSSG (GSSG-Li$_2$) in a complex therapy.

Right after the first injections of GSSG-Li$_2$ (0.01–0.5 mg/kg per day) there was a certain positive effect—decreased intoxication (decrease of temperature to 37.3 C.), pulse 88/min, resolved pulmonary insufficiency. That positive effect due to the use of the treatment became stronger after the following injections (0.01–0.5 mg/kg per day, intravenously for 5 days).

After another week of treatment with GSSG-Li$_2$ (0.01–0.5 mg/kg/day) combined with antibiotics (Claforan 6 g/day, Ampicillin plus Oxacillin, 2 g/day) the patient's state was satisfactory. No complains; pulse 80/min, BP 115/70 mm Hg, breathing slightly decreased on the right, in all regions.

No local inflammation after thoracotomy. Granulating wound in the site of posterior thoracotomy without secretions. Bronchoscopy showed wide anastomosis without granulation. Chest X-ray—normal.

After a month of treatment with GSSG-Li$_2$ (0.01–0.5 mg/kg every other day IV and IM for 3 weeks) the patient's condition was satisfactory. Blood parameters within normal limits (see Table 41).

Summarized effect: quick regression of the purulent process; potentiation of the effect of antibacterial therapy; beneficial blood changes; detoxification; restoration of laboratory parameters.

TABLE 41

Laboratory parameters in patient with severe postoperative complications

| Parameter | Before treatment | After one week of treatment | After one month of treatment |
|---|---|---|---|
| Erythrocytes, $10^{12}/l$ | 3.6 | 4.0 | 4.3 |
| Hemoglobin, g/l | 118 | 128 | 132 |
| Platelets, $10^9/l$ | 200 | 212 | 248 |
| Leukocytes, $10^9/l$ | 30.0 | 8.4 | 7.6 |
| Neutrophils and rods, % | 12 | 5 | 4 |
| Segmentonuclear neutrophils, % | 55 | 55 | 51 |
| Lymphocytes, % | 22 | 31 | 36 |
| Monocytes, % | 4 | 4 | 6 |
| Eosinophils, % | 7 | 5 | 2 |
| ESR, mm/h | 58 | 12 | 10 |
| ALT/mmol/hL | 1.1 | 0.42 | 0.32 |
| AST/mmol/hL | 0.6 | 0.32 | 0.28 |
| Lymphocytes, $10^6/l$ | 6600 | 2604 | 2736 |
| B-lymphocytes (CD20+) $10^6/l$ | 682 | 319 | 324 |
| T-helpers (CD4+), $10^6/l$ | 2188 | 894 | 1112 |
| T-suppressors (CD8+) $10^6/l$ | 2245 | 824 | 879 |
| CD4+/CD8+ ratio | 0.98 | 1.09 | 1.27 |
| IgA, g/l | 4.1 | 4.5 | 3.8 |
| IgM, g/l | 1.8 | 2.7 | 2.4 |
| IgG, g/l | 19.8 | 16.3 | 17.5 |
| Circulating immune complexes | 174 | 95 | 108 |

EXAMPLE 26

Therapeutical Effect of GSSG Series Preparations in Patients with Multiple Sclerosis We examined and treated 19 patients with cerebrospinal form of Multiple sclerosis (MS) aged 23–52 (Table 42). All patients were admitted to the hospital during exacerbation. Diagnosis was verified according to the recommendations of the International association of MS studies (1992). There was a prevalence of patients with progressive MS with relapses. In 5 patients length of relapse was one month; in 7—one to three months, in 7—over three months.

TABLE 42

| The number of patients | Total | 23–40 years | Over 40 | Severe | Moderate | Mild |
|---|---|---|---|---|---|---|
| Male | 4 | 2 | 2 | 4 | — | — |
| Female | 15 | 9 | 6 | 12 | 2 | 1 |

The 90 days' course of treatment was carried out in the following way:

1. GSSG-Na in 10% solution of S-adenosyl-methionine intravenously, once a day for 10 days, daily dose— 0.01–0.5 mg/kg
2. Two weeks' break
3. GSSG-Zn in 10% solution of S-adenosyl-methionine intravenously, every other day for 20 days, daily dose 0.01–0.5 mg/kg
4. Two weeks' break
5. bis-methionil-GSSG in 5% solution of ascorbic acid (vitamin C) intravenously and intramuscularly, alternating routes of administration (one day each), daily dose 0.01–0.5 mg/kg for 30 days.

Patients' investigation was carried out before treatment, one month after the beginning of the treatment, the 3 and 6 months after the beginning of the treatment. CD3+, CD4+, CD8+, CD20+ lymphocyte counts were measured in peripheral blood with immunofluorescent method using monoclonal antibodies; CD4+/CD8+ ratio was counted (Table 11). Cellular immunity was assessed with the Reaction of Suppression of Leukocyte Adhesion in the presence of neuro-specific antigens: S-100 protein, neuronal membrane antigens, myelin basic protein (Table 12). 25 blood donors and patients with radiculopathy were used as the control group.

Initial state of the immune system was characterized by decrease total CD3+ count, significant decrease in CD4+ count, increase in CD8+ count, dysbalance between subpopulations of helpers and suppressors, increase in CD20+ count.

After the treatment there was an improvement in cellular immunity parameters—normalization of CD3+ count, CD4+ count, and CD8+ (T-suppressors) count. In the same time there was a decrease in sensitization of lymphocytes to one or several of the brain tissue antigens. There also was a phenomenon of immunological inversion of S-100 and myelin basic protein levels (Table 12).

Restoration of immune system was accompanied by resolution of neurological symptoms in 84% of patients.

TABLE 43

Changes in mean values of T and B lymphocyte count in MS patients during the treatment with GSSG series preparations.

| Parameter | Donors | Patients before treatment | After one month | After three months | After six months |
|---|---|---|---|---|---|
| CD3+ % | 55.2 ± 1.8 | 45.22 ± 1.80 | 64.08 ± 3.28 | 63.18 ± 2.02 | 70.78 ± 2.86 |
| CD4+ % | 36.0 ± 2.0 | 28.64 ± 1.22 | 33.18 ± 2.86 | 43.64 ± 1.18 | 55.78 ± 2.12 |
| CD8+ % | 19.3 ± 2.2 | 16.76 ± 0.88 | 20.10 ± 3.16 | 24.26 ± 2.56 | 26.34 ± 2.08 |
| CD4/CD8 | 1.90 ± 0.24 | 1.72 ± 0.42 | 1.65 ± 0.24 | 1.79 ± 0.08 | 2.11 ± 0.10 |
| CD20+ % | 12.8 ± 1.8 | 18.78 ± 0.44 | 15.26 ± 0.64 | 15.32 ± 1.44 | 14.44 ± 1.20 |

TABLE 44

Parameters of sensitization of blood lymphocytes of MS patients to brain tissue antigens in Reaction of Suppression of Adhesion of Leukocytes (%)

| Antigen | Patients before treatment | After one month | After three months | After six months |
|---|---|---|---|---|
| S-100 | 54.20 | 72.12 | 66.46 | 42.10 |
| Neuronal membranes antigen | 56.32 | 44.64 | 41.24 | 32.56 |
| Myelin basic protein | 68.34 | 77.30 | 54.323 | 42.20 |

Endogenous level of IFN α and γ and TNF was measured in patients' serum and cerebrospinal fluid (CSF) (Table 45).

An increase in IFN-α during patients' treatment should be stressed. TNF level correlated with neurological disability, measured by Kurtzke score.

TABLE 45

Changes in cytokine level (pcg/ml) after induction by GSSG medications in MS patients

| | Patients before treatment | After one month | After three months | After six months |
| --- | --- | --- | --- | --- |
| IFN-α, pcg/ml | 0 | 202.26 ± 4.38 | 312.14 ± 6.28 | 406.18 ± 4.66 |
| IFN γ, pcg/ml | 36.18 ± 4.42 | 28.6 ± 4.82 | 24.52 ± 3.46 | 12.4 ± 6.22 |
| TNF, pcg/ml | 64.38 ± 8.64 | 52.42 ± 7.62 | 51.86 ± 4.32 | 51.46 ± 3.80 |

Humoral immunity was assessed by the following parameters: B-lymphocytes were counted by measuring superficial immune globulins in immunofluorescent test, IgA, IgM, lgG level were measured by radical immunodiffusion in gel, circulating immune complexes were precipitated in polyethilenglycole (Table 46). Before treatment all patients had significant increase in circulating immune complexes and IgM, and decrease in IgG. IgG level was significantly lower than in the control group.

TABLE 70

Changes in mean levels of immunoglobulins and circulating immune complexes in MS during the treatment course with GSSG medications.

| Parameter | Donors | Patients before treatment | After one month | After three months | After six months |
| --- | --- | --- | --- | --- | --- |
| IgA, mE | 3.2 | 1.3 | 1.4 | 1.6 | 1.4 |
| IgM, mE | 1.8 | 5.4 | 4.6 | 3.5 | 3.8 |
| IgG, mE | 8.4 | 4.2 | 8.4 | 13.4 | 12.3 |
| Circulating immune complexes, units of optical density | 52.1 ± 6.8 | 142.2 ± 8.1 | 124.4 ± 4.4 | 107.4 ± 4.0 | 68.2 ± 5.4 |

Neurological condition of all patients during this course of treatment have more or less improved, there was a decrease in motor index of Hauzer, and improvement in quality of life.

While specific embodiments of the invention have been shown and described, many modifications are possible. For example, other ingredients which do not affect the action of GSSG its derivatives and/or both its extenders, and enhancers/modulators may be intermixed with GSSG alone or in combination with its both extenders, and enhancers/modulators for application to the body. The dosage forms can be packaged in kit form along with syringe or applicator of any type and can be sterilized. Preferably instructions for application to a specific diseases are included in any kit, including the therapeutic agent. We indicate below preferred applications of GSSG or/and its derivatives with or without both extenders, and enhancers/modulators in doses from 0.01 to 0.5 mg of GSSG base per kg of body weight for GSSG and its salts (0.01 to 1.0 mg per kg for the GSSG derivatives) per day for one or more days, or spread over several days, intravenously, intramuscularly, intralymphatically, epicutaneously, or intracavitary for up to 6 months as has been found effective for the diseases noted below.

A prophylactic, therapeutic use of the methods and therapeutic agents of this invention can be made for immunodeficiency states where individuals have been exposed to radioactive and chemical affliction in cases of accidents such as nuclear disasters.

Where the both various extenders and various enhancers/modulators have been noted, other specific extenders which prolong the half life of the oxidized glutathione, or/and other specific enhancers/modulators altering beneficially GSSG/derivative effects may be used. In some cases, one or more of the both different extenders and different enhancers/modulators can be used in combination. Other salts than those specifically noted for GSSG can be used and GSSG derivatives can be the same salt forms as GSSG or other physiologically safe and therapeutically effective forms.

While the drug for parenteral use is preferably in solution form, in some cases colloidal suspensions and the like can be used. Similarly, topical application can include the use of pharmaceutically acceptable ointments, creams and other bases such as petrolatum bases which do not interact with the GSSG/derivatives, as well as with both extenders and enhancers/modulators. Such base materials are known in the art (petrolatum, lanolin, spermaceti; with inter alia addition of acetylsalicilic acid).

Infectious and Immuopathology Diseases

All dosage rates given in the following section below are indicated for GSSG and its salts also referred to as "GSSG base". Because "GSSG base" does not account for the weight of attached derivative chains to the GSSG base the corresponding dosage rates for the GSSG derivatives should be within the interval of from the same as for GSSG base lower level, up to a level which is two-three fold as much as upper one for GSSG and its salts.

AIDS: dosage rate—from 5 to 30 mg per day, entire course is of 6 month duration, with 2 week break after each month;

the administration regimen during the first week—a single injection daily, alternating regimen: one day—intravenous injection, every other day—intramuscular injection;

during the second week—twice a day: one time intravenously (in the morning), other time intramuscularly (in the evening);

the third and the forth weeks—three times a week: $1^{st}$ time—intravenous injection, $2^{nd}$ and $3^{rd}$ time—intramuscular injection;

In case of encephalopathy it is recommended lumbar injections of the medicine once a week during three weeks.

Hepatitis: dosage rate—from 5 to 10 mg per day, entire course is from 1 to 2 months;

during the first three weeks—a single injection daily, alternating regimen: one day—intravenous injection, every other day—intramuscular injection;

afterwards:—two or three injections per a week, $1^{st}$ time—intravenous injection, $2^{nd}$ and $3^{rd}$ time—intramuscular injection;

Herpes: the medicine administration course is the same as in hepatitis

Tuberculosis: Inactive phase: dosage rate—from 5 to 10 mg per day, entire course is of 6 months, with 2 week break after each month and 1 month break after the 3 months of the medicine administration.

during the first three weeks—a single injection daily, alternating regimen: one day—intravenous injection, every other day—intramuscular injection;

during the forth week—two or three injections per a week, $1^{st}$ time—intravenous injection, $2^{nd}$ and $3^{rd}$ time—intramuscular injection;

Active phase: dosage rate—from 5 to 10 mg per day, entire course is of 6 months, the administration regimen in an active phase is the same as in inactive phase.

Meningitis: dosage rate—from 5 to 90 mg per day, entire course is of 2 months;

during the first two weeks—twice a day: one time intravenously (in the morning), other time intramuscularly (in the evening);

afterwards:—two or three injections per a week, $1^{st}$ time—intravenous injection, $2^{nd}$ and $3^{rd}$ time—intramuscular injection;

Lumbar injections of the medicine—a single injection daily is recommended during three days.

Peritonitis: the medicine administration course is the same as in meningitis (except for lumbar injections).

Sepsis: dosage rate—from 5 to 60 mg per day, entire course is no less than 1 months up to full normalization of clinical state and blood data;

during the first two or tree weeks—twice a day: one time intravenously (in the morning), other time intramuscularly (in the evening);

afterwards:—two or three injections per a week, $1^{st}$ time—intravenous injection, $2^{nd}$ and $3^{rd}$ time—intramuscular injection;

Purulent post-operative infectious complications—the medicine administration course is the same as in sepsis.

Immunodepression: dosage rate—from 5 to 20 mg per day, entire course is of 6 months, with 2 week break after each month;

during the first three weeks—a single injection daily, alternating regimen: one day—intravenous injection, every other day—intramuscular injection;

during the forth week—two or three injections per a week, $1^{st}$ time—intravenous injection, $2^{nd}$ and $3^{rd}$ time—intramuscular injection;

Immunodeficiencies of infectious, radiation, or toxic origin: dosage rate is from 5 to 30 mg per day; the medicine administration course is the same as in immunodepression.

Multiple sclerosis: dosage rate is from 5 to 20 mg per day, entire course is of 3 months with 2 week break after each month, and after 6 month break—the repeating of entire course;

the $1^{st}$ month of the entire course: a single injection daily, alternating regimen: one day—intravenous injection, every other day—intramuscular injection;

the $2^{nd}$ month of the entire course: three injections per a week, 1st time—intravenous injection, 2nd and 3rd time—intramuscular injection;

the $3^{rd}$ month of the entire course: two intramuscular injections per a week, with dosage rate from 5 to 10 mg.

Neurodegenerative diseases: the medicine administration course is the same as in multiple sclerosis.

Alzieimer's sclerosis: the medicine administration course is the same as in multiple sclerosis.

Amyotrophic lateral sclerosis: the medicine administration course is the same as in multiple sclerosis.

Glomerulonepbritis: dosage rate is from 5 to 30 mg per day, entire course is from 1 to 3 months with 2 week break after each month;

during the first two weeks—a single injection daily, alternating regimen: one day—intravenous injection, every other day—intramuscular injection;

afterwards:—two or three injections per a week, $1^{st}$ time—intravenous injection, $2^{nd}$ and $3^{rd}$ time—intramuscular injection;

Collagenoses:—the medicine administration course is the same as in glomerulonephritis.

Rheumatoid arthritis:—the medicine administration course is the same as in Glomerulonephritis.

Systemic lupus erythematosus:—the medicine administration course is the same as in Glomerulonephritis.

Allergic diseases:—the medicine administration course is the same as in Glomerulonephritis, along with the topical application of ointment (1–3% containing the active compound)—during 2 weeks, a single application per day, afterwards:—two applications per a week.

Psoriasis:—the medicine administration course is the same as in Glomerulonephritis, along with the topical application of ointment (1–3% containing of the active compound)—during 2 weeks, a single application per day, afterwards:—two applications per a week.

Neoplasms: dosage rate is from 5 to 90 mg per day, entire course is from 1 to 6 months with 2–4 week break after each month;

a single injection daily, alternating regimen: one day—intravenous injection, every other day—intramuscular injection, without or along with endolymphatic application (dosage rate—from 30– 90 mg per day) during 10 days, and local application (regional perfusion) by catheterization (dosage rate—from 30–90 mg per day) during 7 days, three or four applications per week;

the treatment scheme is recommended along with polychemiotherapeutic treatment.

Metastatic processes and hemoblastoses: dosage rate is from 5 to 90 mg per day, entire course is from 1 to 6 months with 2–4 week break after each month;

a single injection daily, alternating regimen: one day—intravenous injection, every other day—intramuscular injection, along with local application (regional perfusion) by catheterization (dosage rate—from 30–90 mg per day) during 7 days, three or four applications per week.

Lympho proliferative diseases (Lymphogranulomatosis and Lymphoma): dosage rate is from 5 to 90 mg per day, entire course is from 1 to 6 months with 2–4 week break after each month;

during the first three weeks—a single injection daily, alternating regimen: one day—intravenous injection, every other day—intramuscular injection, along with endolymphatic application (dosage rate—from 30–90 mg per day) during first 10 days;

afterwards:—the same treatment scheme in combination with glucocorticoides and cytostatics.

FOOTNOTES

1 I Holmlund J. T. Cytokines. Cancer Chemother Biol Response Modif. 1993. 14 P 150–206.
2 Hansson M., Soderstrom T. The colony stimulating factors. Med Oncol Tumor Pharmacother. 1993. 10(1–2). P 5–12.
3 Dillman R. O. The clinical experience with interleukin-2 in cancer therapy. Cancer Biother. 1994 Fal. 9(3). P 183–209.
4 Whittington R., Faulds D. Interleukin-2. A review of its pharmacological properties and therapeutic use in patients with cancer. Drugs. 1993 September 46(3). P 446–514.
5 Hieber U., Heim M E. Tumor necrosis factor for the treatment of malignancies. Oncology. 1994 March–April 51(2). P 142–53.
6 Morstyn G., Sheridan W. P. Hematopoietic growth factors in cancer chemotherapy. Cancer Chemother Biol Response Modif. 1993. 14P353–70.
7 Neidhart J. A. Hematopoietic cytokines. Current use in cancer therapy. Cancer. 1993 December 1. 72(11 Suppl). P 3381–6.
8 Murray H. W. Interferon-gamma and host antimicrobial defense: current and future clinical applications. Am J Med. 1994 November 97(5). P 459–67.
9 Cirelli R. Tyring S. K. Interferons in human papiomavirus infections. Antiviral Res. 1994 July 24(2–3). P 191–204.
10 Sher A. Coffman R. L. Regulation of immunity to parasites by T-cells and T-cell derived cytokines. Annu. Rev. Immunol., 1992, 10. P.385–409.
11 Gillan E., Plunkett M., Cairo M. S. Colony-stimulating factors in the modulation of sepsis. New Horiz. 1993 February 1(1). P 96–109.
12 Nelson S. Role of granulocyte colony-slating factor in the immune response to acute bacterial infection in the non-eutropenic host: an overview. Clin Infect Dis. 1994 February 18 Suppl 2 P S197–204.
13 Offenstadt G., Guidet B., Staikowsky F. Cytokines and severe infections. Pathol Biol (Paris). 1993 October 41(8 Pt 2). P 820–31.
14 Nemunaitis J. Use of hematopoietic growth factors in marrow transplantation. Curr Opin Oncol. 1994 March 6(2). P 139–45.
15 Mittelman M., Lessin L. S. Clinical application of recombinant erythropoietin in myelodysplasia. Hematol Oncol Clin North Am. 1994 October 8(S). P 993–1009.
16 Forman A. D. Neurologic complications of cytokine therapy. Oncology (Huntingt). 1994 April 8(4). P 105–10; discussion 113, 116–7.
17 Hack C. E., Ogilvie A. C., Eisele B., Erenberg A. J., Wagstaff J., Thijs L. G. C1-inhibitor substitution therapy in septic shock and in the vascular leak syndrome induced by high doses of interleukin-2. Intensive Care Med. 1993. 19 Suppl 1 PS19–28.
18 Hieber U., Heim M. E. Thor necrosis factor for the treatment of malignancies. Oncology. 994 March–April 51(2). P 142–53.
19 Saito M. OK-432, a killed streptococcal preparation, in the treatment of animal and human cancer and its mechanisms of action. Form on immunomodulators. Ed. Guenounou M. John Libbey Euotext, Paris, 1995, P 1–11.
20 Barot-Ciorbaru R., Bona C. Immunomodulators from *Nocardia opaca*. Form on immunomodulators. Ed. Guenounou M. John Libbey Eurotext, Paris, 1995, P 1–11.
21 Bloy C. Morales M., Guenounou M. RU 41740 (Biostim), an immunomodulating agent from bacterial orgin Ed. Guenounou M. John Libbey Eurotext, Paris, 1995, P 1–11.
22 Meister A. Anderson M. E. Gluthione. Annu. Rev. Biochem., 1983, 52:711–60.
23 Beutler E. Nutritional and metabolic sects aspects of glutathione. Review. Annu. Rev. Nutr., 1989, 9:287.
24 Textbook of biochemistry: with clinical correlations. Ed. Devlin T. M., 3rd ed. 1992, Wiley-Liss, Inc., NY. P 522–525.
25 Ehrer J. P., Lund L. G. Cellular reducing equivalents and oxidative stress. Free Radio Biol Med. 1994 July 17(1). P 65–75.
26 Michiels C., Raes M., Toussaint O., Remacle J. Importance of Se-glutathione peroxidase, catalase, and Cu/Zn-SOD for cell survival against oxidative stress. Free Radio Biol Med. 1994 September 17(3). P 235–48.
27 Cohen G. Enzymatic/nonenzymatic sources of oxyradicals and regulation of antioxidant defenses. Ann NY Acad Sci. Nov. 17, 1994, 738. P 8–14.
28
Beckett G. J., Hayes J. D. Glutathione S-transferase: biomedical applications. Advan. Clin. Chem. 1993, vol. 30, P 281–380.
29 Composition and method for disease treatment PCT/US/92/04653.
30 Droge W., Schule-Osthoff K., Mihm S., Galter D., Schenk H., Eck H. P., Roth S., Gmunder H. Functions of glutathione and glutathione disulfide in immunology and immunopathology. FASEB J. 1994 November 8(14). P 1131–8.
31 Sardesai V., M. Role of antioxidants in health maintenance. Nutr Clin Pract 1995 February 10(1). P 19–25.
32 Giugliano D., Ceriello A., Paoliso G. Diabetes mellitus, hypertension, and cardiovascular disease: which role for oxidative stress? Metabolism. 1995 March 44(3). P 363–8.
33 Keusch G. T. Anitioxidants in infection. J Nutr Sci Vitaminol (Tokyo). 1993. 39 Suppl P S 23–33.
34 Dipeptide compound having pharmaceutical activity and compositions containing them. U.S. Pat. No. 4,761,399.
35 G-L-Glutamyl-L-cysteine ethyl ester and pharmaceutical compositions containing the same as an effective ingredient. U.S. Pat. No. 4,927,808.
36 Therapeutic agents for ischemic heart diseases. U.S. Pat. No. 4,968,671.
37 Method for insuring adequate intracellular glutathione in tissue. EP 0 502 313 A2.
38 Composition and method for disease treatment. PCT/US/92/04653.
39 Glutathione as hemoprotective agent. PCT/EP/93/01494.
40 Pharmaceutical compositions having antineoplastic activity. U.S. Pat. No. 4,871,528.
41 Sokolovsky M., Wilchek M. Patchornik A. On the synthesis of cystein peptides. J. Amer. Chem. Soc, 1964, March 86(6), P 1202–6.

What is claimed is:

1. A method of stimulating endogenous production of cytokines and hemopoietic factors said method consisting essentially of introducing to a mammalian body in need of stimulation of cytokines or hemopoietic factors or both, an amount effective to stimulate production of said cytokine or hemopoietic factors or both, of an oxidized glutathione form selected from the group consisting of oxidized glutathione, a pharmaceutically acceptable oxidized glutathione salt, a pharmaceutically acceptable glutathione derivative and mixtures thereof, for a period of time to stimulate said endogenous production to obtain a therapeutic effect.

2. A method in accordance with the method of claim 1, wherein said glutathione form is introduced parenterally.

3. A method in accordance with the method of claim 1, wherein said glutathione form is introduced topically.

4. A method in accordance with the method of claim 1, wherein said glutathione form is introduced along with an extender of the half life of said oxidized glutathione and/or its pharmaceutically acceptable salt form, and/or its pharmaceutically acceptable derivative.

5. A method in accordance with the method of claim 1, wherein said glutathione form is introduced along with an enhancer/beneficial modulator of the biological or therapeutical effects of said glutathione form.

6. A method in accordance with the method of claim 4, wherein said extender is selected from the group consisting of pro-oxidant compounds, agents capable of forming weak ionic or coordinating links stabilizing the GSSG molecule, materials which are competitors of NADP-H-dependent reduction of GSSG into GSH catalyzed by glutathione reductase, compounds capable of producing reversible inhibition of reduction of NADP+ into NADP-H catalyzed by glucose-6-phosphate-dehydrogenase or by other NADP-H-dependent enzymes, and mixtures thereof.

7. A method in accordance with the method of claim 6, wherein said extender is a peroxide.

8. A method in accordance with the method of claim 6, wherein said extender is ascorbic acid.

9. A method in accordance with the method of claim 6, wherein said extender is dimethylsulfoxide.

10. A method in accordance with the method of claim 6, wherein said extender is inosine.

11. A method in accordance with the method of claim 6, wherein said extender is cystamine.

12. A method in accordance with the method of claim 5, wherein said enhancer/beneficial modulator is selected from the group consisting of methyl moiety donators, representatives of intracellular redox-oxidative pairs, and mixtures thereof.

13. A method in accordance with the method of claim 12, wherein said enhancer/beneficial modulator is choline-chloride.

14. A method in accordance with the method of claim 12, wherein said enhancer/beneficial modulator is S-adenosyl-methionine.

15. A method in accordance with the method of claim 12, wherein said enhancer/beneficial modulator is lipoic acid.

16. A method in accordance with the method of claim 12, wherein said enhancer/beneficial modulator is folic acid.

17. A method in accordance with the method of claim 2, wherein said glutathione form is introduced at a dose of from 0.01 to 0.5 mg of GSSG base per kilogram of body weight for GSSG base and GSSG salts or from 0.01 to 1.0 mg per kg for GSSG derivatives at least one time each 24 hour period until said therapeutic effect is obtained.

18. A method in accordance with the method of claim 17, wherein said glutathione form is introduced parenterally in a pharmaceutically acceptable solution at a concentration of from 0.01 to 2.0% by weight of oxidized glutathione base for GSSG base and GSSG salts or from 0.01 to 4.0% by weight for GSSG derivatives.

19. A method in accordance with the method of claim 18, wherein said solution further includes, or is administered in a combination with an extender selected from the group consisting of 0.03% to 0.0003% v/v hydrogen peroxide, 0.1% to 10% w/v ascorbic acid, 0.1% to 3% v/v dimethylsulfoxide, 0.1% to 5% w/v inosine, 0.1% to 3% w/v cystamine, and mixtures thereof.

20. A method in accordance with the method of claim 1, wherein said mammalian body is in need of stimulation of cytokine or hemopoietic factor production to treat condition selected from the group consisting of neoplastic, infectious, hematologic and immunologic diseases.

21. A method in accordance with the method of claim 20, wherein said disease is infectious.

22. A method in accordance with the method of claim 20, wherein said disease is hematologic.

23. A method in accordance with the method of claim 20, wherein said disease is immunologic.

24. A method in accordance with the method of claim 20, wherein said disease is neoplastic.

25. A method in accordance with the method of claim 20, wherein said disease is selected from the group consisting of AIDS, hepatitis, herpes, tuberculosis, meningitis, peritonitis, sepsis, and purulent post-operative complications caused by infection.

26. A method in accordance with the method of claim 20, wherein said disease is selected from the group consisting of immunodepression, multiple sclerosis, alzheimer sclerosis, neurogenerative diseases, amyotrophic lateral sclerosis, glomerulonephirits, collagenosis, rheumatoid arthritis, lupus, psoriasis, diabetes mellitus and allergic disease.

27. A method in accordance with the method of claim 20, wherein said disease is selected from the group consisting of metastatic spreading, hemobastosis, malignant tumors, lymphogranulomatous, lymphomas, immunodeficiency caused by radioactive and chemical affliction.

28. A method in accordance with the method of claim 1, 2, 3, 4, or 5 wherein said oxidized glutathione is in a salt form.

29. A method in accordance with the method of claim 1, wherein said salt is the disodium salt.

30. A method in accordance with the method of claim 1, wherein said salt is the dilithium salt.

31. A method in accordance with the method of claim 1, wherein said salt contains one or more atoms of potassium.

32. A method in accordance with the method of claim 1, wherein said salt contains one or more atoms of calcium.

33. A method in accordance with the method of claim 1, wherein said salt contains one or more atoms of zinc.

34. A method in accordance with the method of claim 1, wherein said salt contains one or more atoms of molybdenum.

35. A method in accordance with the method of claim 1, wherein said salt contains one or more atoms of vanadium.

36. A method in accordance with the method of claim 1, wherein said salt contains one or more atoms of fluoride.

37. A method in accordance with the method of claim 1, 2, 3, 4 or 5 wherein a pharmaceutically acceptable derivative of oxidized glutathione is introduced to a mammalian body in need of stimulation of cytokines or hemopoietic factors or both.

38. A method in accordance with the method of claim 1, wherein said oxidized gluthathione form is a derivative which is GSSG covalently bound to cysteamine (S-thioethylamine-glutathione disulfide).

39. A method in accordance with the method of claim 1, wherein said oxidized gluthathione form is a derivative which is GSSG covalently bound to lipoic acid(bis-[6,8-thiooctanyl]•glutathione disulfide).

40. A method in accordance with the method of claim 1, wherein said oxidized gluthathione form is a derivative which is GSSG covalently bound to a member of the group consisting of carnosine ([β-alanyl-histidyl]•glutathione disulfide) and adenosine ([9-β-D-ribofuranosyladenyl]•glutathione disulfide).

41. A method in accordance with the method of claim 1, wherein said oxidized gluthathione form is a derivative which is GSSG covalently bound to methionine (bis-[2-amino-4-[methylthio]butanoyl]•glutathione disulfide).

42. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of oxidized glutathione, and/or a pharmaceutically acceptable salt of oxidized glutathione, and/or a pharmaceutically acceptable derivative of oxidized glutathione, as an active substance, along with a pharmaceutically acceptable excipient in a parenteral treatment form,
wherein said substance is formulated in the form of a sterile injectable solution of oxidized glutathione, and/or a pharmaceutically acceptable salt of oxidized glutathione, and/or a pharmaceutically acceptable derivative of oxidized glutathione, in a pharmaceutically acceptable solvent,
said therapeutic agent being in a combination with a pharmaceutically acceptable extender capable of enhancing and prolonging a therapeutic effect of said agent by increasing the half-life of oxidized glutathione,
wherein said extender is hydrogen peroxide.

43. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of oxidized glutathione, and/or a pharmaceutically acceptable salt of oxidized glutathione, and/or a pharmaceutically acceptable derivative of oxidized glutathione, as an active substance, along with a pharmaceutically acceptable excipient in a parenteral treatment form,
wherein said substance is formulated in the form of a sterile injectable solution of oxidized glutathione, and/or a pharmaceutically acceptable salt of oxidized glutathione, and/or a pharmaceutically acceptable derivative of oxidized glutathione, in a pharmaceutically acceptable solvent,
said therapeutic agent being in a combination with a pharmaceutically acceptable extender capable of enhancing and prolonging a therapeutic effect of said agent by increasing the half-life of oxidized glutathione,
wherein said extender is ascorbic acid.

44. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of oxidized glutathione, and/or a pharmaceutically acceptable salt of oxidized glutathione, and/or a pharmaceutically acceptable derivative of oxidized glutathione, as an active substance, along with a pharmaceutically acceptable excipient in a parenteral treatment form,
wherein said substance is formulated in the form of a sterile injectable solution of oxidized glutathione, and/or a pharmaceutically acceptable salt of oxidized glutathione, and/or a pharmaceutically acceptable derivative of oxidized glutathione, in a pharmaceutically acceptable solvent,
said therapeutic agent being in a combination with a pharmaceutically acceptable extender capable of enhancing and prolonging a therapeutic effect of said agent by increasing of oxidized glutathione,
wherein said extender is dimethyl sulfoxide.

45. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of oxidized glutathione, and for a pharmaceutically acceptable salt oxidized glutathione, and/or a pharmaceutical acceptable derivative of oxidized glutathione, as an active substance, along with a pharmaceutically acceptable excipient in a parenteral treatment form,
wherein said substance is formulated in the form of a sterile injectable solution of oxidized glutathione, and/or a pharmaceutically acceptable salt of oxidized glutathione, and/or a pharmaceutically acceptable derivative of oxidized glutathione, in a pharmaceutically acceptable solvent,
said therapeutic agent being in a combination with a pharmaceutically acceptable extender capable of enhancing and prolonging a therapeutic effect of said agent by increasing the half-life of oxidized glutathione,
wherein said extender is inosine.

46. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of oxidized glutathione, and/or a pharmaceutically acceptable salt of oxidized glutathione, and/or a pharmaceutically acceptable derivative of oxidized glutathione, as an active substance, along with a pharmaceutically acceptable excipient in a parenteral treatment form,
wherein said substance is formulated in the form of a sterile injectable solution of oxidized glutathione, and/or a pharmaceutically acceptable salt of oxidized glutathione, and/or a pharmaceutically acceptable derivative of oxidized glutathione, in a pharmaceutically acceptable solvent,
said therapeutic agent being in a combination with a pharmaceutically acceptable extender capable of enhancing and prolonging a therapeutic effect of said agent by increasing the half-life of oxidized glutathione,
wherein said extender is cystamine.

47. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of oxidized glutathione, and/or a pharmaceutically acceptable salt of oxidized glutathione, and/or a pharmaceutically acceptable derivative of oxidized glutathione, as an active substance, along with a pharmaceutically acceptable excipient in a parenteral treatment form, wherein said substance is formulated in the form of a sterile injectable solution of oxidized glutathione, and/or a pharmaceutically acceptable salt of oxidized glutathione, and/or a pharmaceutically acceptable derivative of oxidized glutathione, in a pharmaceutically acceptable solvent, said therapeutic agent being in a combination with a pharmaceutically acceptable enhancer/beneficial modulator capable of enhancing and/or altering beneficially a therapeutic effect of said agent by mechanisms other than increasing the half-life of oxidized glutathione.

48. A therapeutic agent in accordance with claim 47, wherein said enhancer/beneficial modifier is choline-chloride.

49. A therapeutic agent in accordance with claim 47, wherein said enhancer/beneficial modifier is S-adenosyl-methionine.

50. A therapeutic agent in accordance with claim 47, wherein said enhancer/beneficial modifier is lipoic acid.

51. A therapeutic agent in accordance with claim 47, wherein said enhancer/beneficial modifier is folic acid.

52. A method in accordance with the method of claim 4, wherein said oxidized glutathione form is introduced into said body in a drug form as an injectable solution, wherein said oxidized glutathione and/or a pharmaceutically acceptable salt, and/or a pharmaceutically acceptable derivative is present in such solution at a concentration of from 0.01 to 2.0% of GSSG base by weight for GSSG base and GSSG salts and with a concentration of from 0.01 to 4.0% for GSSG derivatives.

53. A method in accordance with the method of claim 52, wherein said injectable drug comprises an extender selected from the group consisting of hydrogen peroxide, ascorbic acid, dimethyl sulfoxide, inosine, and cystamine; or such an extender is administered separately.

54. A method in accordance with the method of claim 52, wherein said injectable drug solution comprises an enhancer/beneficial modulator selected from the group consisting of choline-chloride, S-adenosilmethionine, lipoic and folic acid; or such an enhancer/beneficial modulator is administered separately.

55. A method in accordance with the method of claim 1, wherein said mammalian body is in need of stimulation of cytokine or hemopoietic factor production to treat a condition selected from the group consisting of ischemic, diastrophic and degenerative diseases.

56. A therapeutic agent for treating neoplastic, infectious, hematologic, or immunologic diseases in which stimulation of the endogenous cytokine and hemopoietic factor production is considered beneficial, said therapeutic agent consisting essentially of an amount stimulate production of said cytokine or hemopoietic factor, of S-thioethylamine•glutathione disulfide substance, along with a pharmaceutically acceptable excipient in a parenteral treatment form.

57. A therapeutic agent for treating neoplastic, infectious, hematologic, or immunologic diseases in which simulation of the endogenous cytokine and hemopoietic factor production is considered beneficial, said therapeutic agent consisting essentially of an amount effective to stimulate production of said cytokine or hemopoietic factor of bis-[DL-6,8, thioctic acid]•glutathione disulfide, along with a pharmaceutically acceptable excipient in a parenteral treatment form.

58. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of [β-alanyl-L-histidyl]•gluthanione disulfide as an active substance, along with a pharmaceutically acceptable excipient in a parenteral treatment form.

59. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of [9-βD-ribofuranosyladenyl]•glutathione disulfide as an active substance, along with a pharmaceutically acceptable excipient in a parenteral treatment form.

60. A therapeutic agent for treating neoplastic, infectious, hematologic, or immunologic diseases in which stimulation of the endogenous cytokine and hemopoietic factor production is considered beneficial, said therapeutic agent consisting essentially of an amount effective to stimulate production of said cytokine or hemopoietic factor, of bis-[L-2-amino-4-[methylthio]butanoic acid]•glutathione disulfide as an active substance, along with a pharmaceutically acceptable excipient in a parenteral treatment form.

* * * * *